(12) United States Patent
Kawaue et al.

(10) Patent No.: US 8,367,299 B2
(45) Date of Patent: Feb. 5, 2013

(54) RESIST COMPOSITION, METHOD OF FORMING RESIST PATTERN, COMPOUND AND ACID GENERATOR

(75) Inventors: Akiya Kawaue, Kawasaki (JP); Yoshiyuki Utsumi, Kawasaki (JP); Takehiro Seshimo, Kawasaki (JP); Tsuyoshi Nakamura, Kawasaki (JP); Naoto Motoike, Kawasaki (JP); Hiroaki Shimizu, Kawasaki (JP); Kensuke Matsuzawa, Kawasaki (JP); Hideo Hada, Kawasaki (JP)

(73) Assignee: Tokyo Ohka Kogyo Co., Ltd., Kawasaki-shi (JP)

( * ) Notice: Subject to any disclaimer, the term of this patent is extended or adjusted under 35 U.S.C. 154(b) by 0 days.

(21) Appl. No.: 13/233,832

(22) Filed: Sep. 15, 2011

(65) Prior Publication Data
US 2012/0009521 A1    Jan. 12, 2012

Related U.S. Application Data

(63) Continuation of application No. 12/499,610, filed on Jul. 8, 2009.

(30) Foreign Application Priority Data

Jul. 15, 2008   (JP) .................................. 2008-184185
Oct. 21, 2008   (JP) .................................. 2008-271120
May 21, 2009   (JP) .................................. 2009-123095

(51) Int. Cl.
    *G03F 7/039*    (2006.01)
(52) U.S. Cl. ......... 430/270.1; 522/15; 522/31; 430/921; 430/925; 430/326; 562/30; 549/31; 546/326; 544/5; 560/150
(58) Field of Classification Search .................. None
    See application file for complete search history.

(56) References Cited

U.S. PATENT DOCUMENTS

| | | | |
|---|---|---|---|
| 4,491,628 A * | 1/1985 | Ito et al. ........................ | 430/176 |
| 5,220,037 A | 6/1993 | Schwalm et al. | |
| 5,609,989 A * | 3/1997 | Bantu et al. ................ | 430/270.1 |
| 5,945,517 A | 8/1999 | Nitta et al. | |
| 6,153,733 A | 11/2000 | Yukawa et al. | |
| 6,303,263 B1 * | 10/2001 | Chen et al. ................ | 430/270.1 |
| 6,818,379 B2 | 11/2004 | Kamabuchi et al. | |
| 2004/0058269 A1 | 3/2004 | Hada et al. | |
| 2004/0191676 A1 * | 9/2004 | Nakao et al. ............... | 430/270.1 |
| 2005/0064329 A1 | 3/2005 | Takahashi | |
| 2008/0063974 A1 * | 3/2008 | Shimizu et al. ............ | 430/270.1 |

FOREIGN PATENT DOCUMENTS

| | | |
|---|---|---|
| EP | 1780198 A1 | 5/2007 |
| JP | H09-208554 | 8/1997 |
| JP | H11-035551 | 2/1999 |
| JP | H11-035552 | 2/1999 |
| JP | H11-035573 | 2/1999 |
| JP | H11-322707 | 11/1999 |
| JP | 2003-167347 | 6/2003 |
| WO | WO 2004/074242 | 9/2004 |

OTHER PUBLICATIONS

Lawrence Ferreira, Sanjay Malik, Thomas R. Sarubbi, Andrew J. Blakeney and Brian Maxwell, "Choice of amines as stabilizers for chemically amplified resist systems", Proc. SPIE 3333, 236 (1998); http://dx.doi.org/10.1117/12.312413.*
Non-Final Office Action issued in U.S. Appl. No. 12/499,610, filed Jun. 23, 2011.
Final Office Action issued in U.S. Appl. No. 12/499,610, filed Dec. 12, 2011.

* cited by examiner

*Primary Examiner* — Cynthia Hamilton
(74) *Attorney, Agent, or Firm* — Knobbe Martens Olson & Bear LLP

(57) ABSTRACT

A resist composition including: a base component (A) which exhibits changed solubility in an alkali developing solution under action of acid; and an acid-generator component (B) which generates acid upon exposure, wherein said acid-generator component (B) comprises an acid generator (B1) including a compound represented by general formula (b1-11) shown below:
wherein $R^{7\prime\prime}$ to $R^{9\prime\prime}$ each independently represent an aryl group or an alkyl group, wherein two of $R^{7\prime\prime}$ to $R^{9\prime\prime}$ may be bonded to each other to form a ring with the sulfur atom, and at least one of $R^{7\prime\prime}$ to $R^{9\prime\prime}$ represents a substituted aryl group having a group represented by general formula (I) shown below as a substituent; $X^-$ represents an anion; and $R^f$ represents a fluorinated alkyl group.

[Chemical Formula 1]

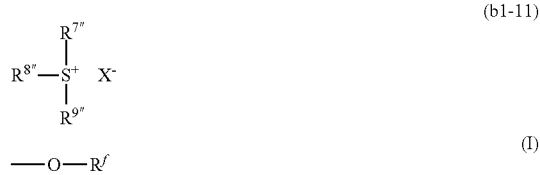

15 Claims, 1 Drawing Sheet

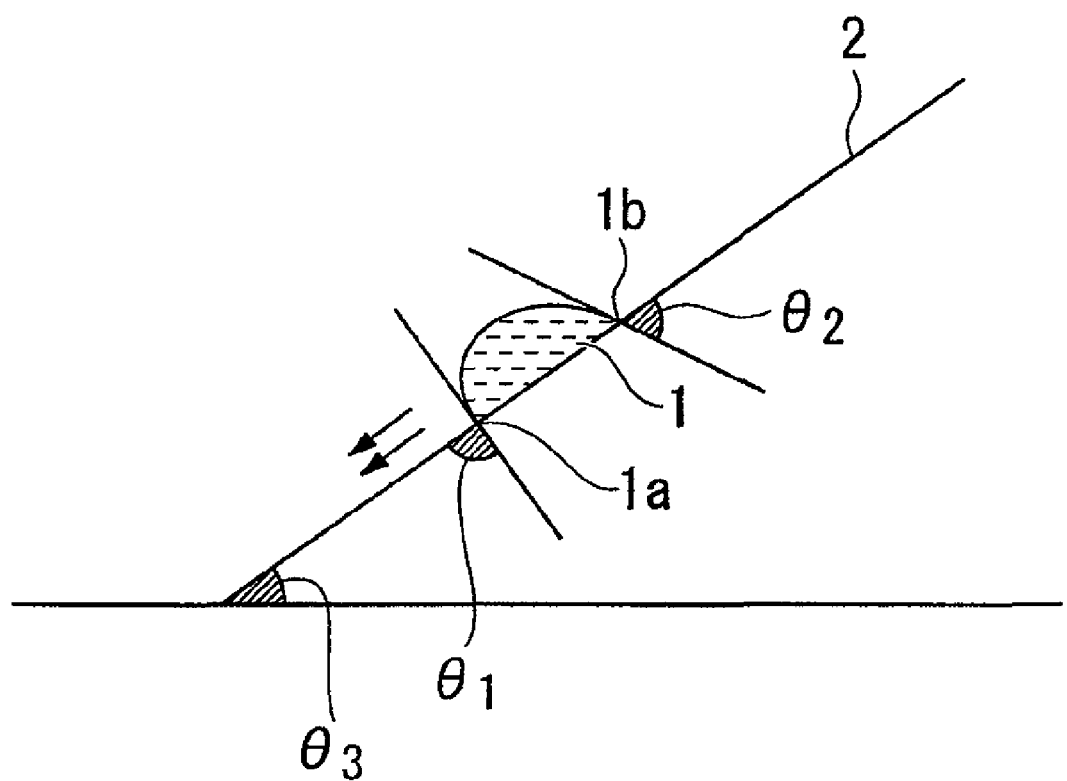

RESIST COMPOSITION, METHOD OF FORMING RESIST PATTERN, COMPOUND AND ACID GENERATOR

RELATED APPLICATIONS

This application is a continuation of U.S. patent application Ser. No. 12/499,610, filed Jul. 8, 2009, which claims priority under 35 U.S.C. §119(a)-(d) to Japanese Patent Application No. 2008-184185, filed Jul. 15, 2008, Japanese Patent Application No. 2008-271120, filed Oct. 21, 2008, and Japanese Patent Application No. 2009-123095, filed May 21, 2009, the contents of which are incorporated herein by reference.

BACKGROUND OF THE INVENTION

1. Field of the Invention

The present invention relates to a resist composition, a method of forming a resist pattern using the resist composition, a compound useful as an acid generator for a resist composition, and an acid generator.

2. Description of Related Art

In lithography techniques, for example, a resist film composed of a resist material is formed on a substrate, and the resist film is subjected to selective exposure to radial rays such as light or electron beams through a mask having a predetermined pattern, followed by development, thereby forming a resist pattern having a predetermined shape on the resist film.

For miniaturization of semiconductor devices, shortening of the wavelength of the exposure light source, and increasing of the numerical aperture (NA) of the projector lens have progressed. Currently, exposure apparatuses in which an ArF excimer laser having a wavelength of 193 nm is used as an exposure light source and having a NA=0.84 have been developed. As shortening the wavelength of the exposure light source progresses, it is required to improve various lithography properties of the resist material, such as the sensitivity to the exposure light source and a resolution capable of reproducing patterns of minute dimensions. As a resist material which satisfies these conditions, a chemically amplified resist is used, which includes a base resin that exhibits a changed solubility in an alkali developing solution under action of acid and an acid generator that generates acid upon exposure (Patent Document 1).

Currently, resins that contain structural units derived from (meth)acrylate esters within the main chain (acrylic resins) are now typically used as base resins for resists that use ArF excimer laser lithography, as they exhibit excellent transparency in the vicinity of 193 nm.

Here, the term "(meth)acrylic acid" is a generic term that includes either or both of acrylic acid having a hydrogen atom bonded to the α-position and methacrylic acid having a methyl group bonded to the α-position. The term "(meth) acrylate ester" is a generic term that includes either or both of the acrylate ester having a hydrogen atom bonded to the α-position and the methacrylate ester having a methyl group bonded to the α-position. The term "(meth)acrylate" is a generic term that includes either or both of the acrylate having a hydrogen atom bonded to the α-position and a methacrylate having a methyl group bonded to the α-position.

[Patent Document 1] Japanese Unexamined Patent Application, First Publication No. 2003-167347

SUMMARY OF THE INVENTION

As the above-mentioned miniaturization of resist patterns has continued to progress, in the formation of a resist pattern, problems have arisen, including formation of T-top shapes in line and space patterns and occurrence of "Not Open" defects in contact hole patterns, in which a portion of, or all of, a hole pattern is not open. In particular, the occurrence of "Not Open" defects in contact hole patterns has become a significant issue. Therefore, development of a novel material which is capable of solving such problems has been demanded.

The present invention takes the above circumstances into consideration, with an object of providing a novel compound useful as an acid generator for a resist composition, an acid generator including the compound, a resist composition containing the acid generator, and a method of forming a resist pattern that uses the resist composition.

For solving the above-mentioned problems, the present invention employs the following aspects.

Specifically, a first aspect of the present invention is a resist composition including a base component (A) which exhibits changed solubility in an alkali developing solution under action of acid and an acid-generator component (B) which generates acid upon exposure, the acid-generator component (B) including an acid generator (B1) including a compound represented by general formula (b1-11) shown below.

[Chemical Formula 1]

wherein $R^{7\prime\prime}$ to $R^{9\prime\prime}$ each independently represents an aryl group or an alkyl group, wherein two of $R^{7\prime\prime}$ to $R^{9\prime\prime}$ may be bonded to each other to form a ring with the sulfur atom, and at least one of $R^{7\prime\prime}$ to $R^{9\prime\prime}$ represents a substituted aryl group having a group represented by general formula (I) shown below as a substituent; and $X^-$ represents an anion.

[Chemical Formula 2]

wherein $R^f$ represents a fluorinated alkyl group.

A second aspect of the present invention is a method of forming a resist pattern, including: applying a resist composition of the first aspect to a substrate to form a resist film on the substrate; subjecting said resist film to exposure; and subjecting said resist film to alkali developing to form a resist pattern.

A third aspect of the present invention is a compound represented by general formula (b1-11) shown below.

[Chemical Formula 3]

wherein $R^{7\prime\prime}$ to $R^{9\prime\prime}$ each independently represent an aryl group or an alkyl group, wherein two of $R^{7\prime\prime}$ to $R^{9\prime\prime}$ may be bonded to each other to form a ring with the sulfur atom, and at least one of $R^{7\prime\prime}$ to $R^{9\prime\prime}$ represents a substituted aryl group having a group represented by general formula (I) shown below as a substituent; and $X^-$ represents an anion.

[Chemical Formula 4]

wherein $R^f$ represents a fluorinated alkyl group.

A fourth aspect of the present invention is an acid generator including the compound of the third aspect.

In the present description and claims, unless specified otherwise, the term "alkyl group" is deemed to include linear, branched and cyclic, monovalent saturated hydrocarbon groups.

The term "alkylene group" includes linear, branched or cyclic divalent saturated hydrocarbon, unless otherwise specified.

A "lower alkyl group" is an alkyl group of 1 to 5 carbon atoms.

A "halogenated lower alkyl group" is an alkyl group in which some or all of the hydrogen atoms have been substituted with halogen atoms, wherein examples of the halogen atoms include a fluorine atom, chlorine atom, bromine atom and iodine atom.

The term "aliphatic" is a relative concept used in relation to the term "aromatic", and defines a group or compound that has no aromaticity.

The term "structural unit" refers to a monomer unit that contributes to the formation of a resin component (a polymer or copolymer).

The term "exposure" is used as a general concept that includes irradiation with any form of radiation.

According to the present invention, there are provided a novel compound useful as an acid generator for a resist composition, an acid generator including the compound, a resist composition containing the acid generator, and a method of forming a resist pattern using the resist composition.

BRIEF DESCRIPTION OF THE DRAWINGS

FIG. 1 is a diagram describing an advancing angle ($\theta 1$), a receding angle ($\theta 2$) and a sliding angle ($\theta 3$).

DESCRIPTION OF REFERENCE NUMERALS AND CHARACTERS

1: Liquid droplet; 1a: Bottom edge; 1b: Top edge; 2: Flat surface; $\theta 1$: Advancing angle; $\theta 2$: Receding angle; $\theta 3$: Sliding angle

DETAILED DESCRIPTION OF THE INVENTION

<<Resist Composition>>

A resist composition of the present invention includes a base component (A) (hereafter, frequently referred to as "component (A)") which exhibits changed solubility in an alkali developing solution under the action of acid and an acid generator component (B) (hereafter, frequently referred to as "component (B)") which generates acid upon exposure.

In the resist composition, when acid is generated from the component (B) upon exposure, the action of the generated acid causes a change in the solubility of the component (A) in an alkali developing solution. As a result, during resist pattern formation, when a resist film formed using the resist composition of the present invention is subjected to selective exposure, the solubility in the alkali developing solution of the exposed portions increases, whereas the solubility in the alkali developing solution of the unexposed portions remains unchanged, meaning alkali developing of the resist film can then be used to form a resist pattern.

<Component (A)>

As the component (A), an organic compound typically used as a base component for a chemically amplified resist composition can be used alone, or two or more of such organic compounds can be mixed together.

Here, the term "base component" refers to an organic compound capable of forming a film, and is preferably an organic compound having a molecular weight of 500 or more. When the organic compound has a molecular weight of 500 or more, the film-forming ability is improved, and a resist pattern of nano level can be easily formed.

The organic compounds having a molecular weight of 500 or more that may be used as the base component are broadly classified into low molecular weight organic compounds having a molecular weight of 500 to less than 2,000 (namely, "low molecular weight materials") and high molecular weight organic compounds having a molecular weight of 2,000 or more (namely, "polymeric materials"). Generally, a non-polymer is used as the low molecular weight material. A resin (a polymer or copolymer) is used as the polymeric material. With respect to the aforementioned resin, the "molecular weight" refers to the polystyrene equivalent weight average molecular weight determined by gel permeation chromatography (GPC). Hereafter, the simplified term "resin" refers to a resin having a molecular weight of 2,000 or more.

As the component (A), a resin which exhibits changed alkali solubility under the action of acid or a low molecular weight material which exhibits changed alkali solubility under the action of acid may be used. Alternatively, a combination of these materials may also be used.

When the resist composition of the present invention is a negative resist composition, for example, as the component (A), a base component that is soluble in an alkali developing solution is used, and a cross-linking agent is blended in the negative resist composition.

In the negative resist composition, when acid is generated from the component (B) upon exposure, the action of the generated acid causes cross-linking between the base component and the cross-linking agent, and the cross-linked portion becomes insoluble in an alkali developing solution. Therefore, in the formation of a resist pattern, by conducting selective exposure of a resist film formed by applying the negative resist composition onto a substrate, the exposed portions become insoluble in an alkali developing solution, whereas the unexposed portions remain soluble in an alkali developing solution, and hence, a resist pattern can be formed by alkali developing.

Generally, as the base component for a negative resist composition, a resin that is soluble in an alkali developing solution (hereafter, referred to as "alkali-soluble resin") is used.

As the alkali-soluble resin, it is preferable to use a resin having a structural unit derived from at least one of α-(hydroxyalkyl)acrylic acid and a lower alkyl ester of α-(hydroxyalkyl)acrylic acid, as it enables formation of a satisfactory resist pattern with minimal swelling. Here, the term "α-(hydroxyalkyl)acrylic acid" refers to one or both of acrylic acid in which a hydrogen atom is bonded to the carbon atom on the α-position having the carboxyl group bonded thereto, and α-hydroxyalkylacrylic acid in which a hydroxyalkyl group (preferably a hydroxyalkyl group of 1 to 5 carbon atoms) is bonded to the carbon atom on the α-position.

As the cross-linking agent, typically, an amino-based cross-linking agent such as a glycoluril having a methylol group or alkoxymethyl group is preferable, as it enables formation of a resist pattern with minimal swelling. The amount of the cross-linking agent added is preferably within the range from 1 to 50 parts by weight, relative to 100 parts by weight of the alkali-soluble resin.

When the resist composition of the present invention is a positive resist composition, as the component (A), a base component that exhibits increased solubility in an alkali developing solution under the action of acid is used. More specifically, the base component is substantially insoluble in an alkali developing solution prior to exposure, but when acid is generated from the component (B) upon exposure, the action of this acid causes an increase in the solubility of the base component in an alkali developing solution. Accordingly, during resist pattern formation, when a resist film formed by applying the positive resist composition to a substrate is selectively exposed, the exposed portions change from being substantially insoluble in an alkali developing solution to being alkali-soluble, whereas the unexposed portions remain alkali-insoluble, meaning a resist pattern can be formed by alkali developing.

The resist composition of the present invention is preferably a positive resist composition. That is, in the resist composition of the present invention, the component (A) is preferably a base component which exhibits increased solubility in an alkali developing solution under action of acid.

The component (A) may be a resin component (A1) which exhibits increased solubility in an alkali developing solution under action of acid (hereafter, referred to as "component (A1)"), a low molecular weight compound which exhibits increased solubility in an alkali developing solution under action of acid (hereafter, referred to as "component (A2)"), or a mixture of the component (A1) and the component (A2).

[Component (A1)]

As the component (A1), a resin component (base resin) typically used as a base component for a chemically amplified resist composition can be used alone, or two or more of such resin components can be mixed together.

In the present invention, it is preferable that the component (A1) include a structural unit derived from an acrylate ester.

In the present descriptions and the claims, the term "structural unit derived from an acrylate ester" refers to a structural unit which is formed by the cleavage of the ethylenic double bond of an acrylate ester.

The term "acrylate ester" is a generic term that includes acrylate esters having a hydrogen atom bonded to the carbon atom on the α-position, and acrylate esters having a substituent (an atom other than a hydrogen atom or a group) bonded to the carbon atom on the α-position. As the substituent, a lower alkyl group or a halogenated lower alkyl group can be mentioned. With respect to the "structural unit derived from an acrylate ester", the "α-position (the carbon atom on the α-position)" refers to the carbon atom having the carbonyl group bonded thereto, unless specified otherwise.

With respect to the acrylate ester, specific examples of the lower alkyl group for the substituent at the α-position include linear or branched alkyl groups such as a methyl group, an ethyl group, a propyl group, an isopropyl group, an n-butyl group, an isobutyl group, a tert-butyl group, a pentyl group, an isopentyl group, and a neopentyl group.

Specific examples of the halogenated lower alkyl group include groups in which some or all of the hydrogen atoms of the aforementioned "lower alkyl group for the substituent at the α-position" are substituted with halogen atoms. Examples of the halogen atom include a fluorine atom, a chlorine atom, a bromine atom and an iodine atom, and a fluorine atom is particularly desirable.

In the present invention, it is preferable that a hydrogen atom, a lower alkyl group or a halogenated lower alkyl group is bonded to the α-position of the acrylate ester, more preferably a hydrogen atom, a lower alkyl group or a fluorinated lower alkyl group. In terms of industrial availability, a hydrogen atom or a methyl group is particularly desirable.

It is particularly desirable that the component (A1) have a structural unit (a1) derived from an acrylate ester containing an acid dissociable, dissolution inhibiting group.

Further, in addition to this structural unit (a1), this polymer preferably also has a structural unit (a2) derived from an acrylate ester that contains a lactone-containing cyclic group.

Moreover, in addition to the structural unit (a1), or in addition to the combination of the structural units (a1) and (a2), the above-mentioned component (A1) (polymer) preferably also has a structural unit (a3) derived from an acrylate ester that contains a polar group-containing aliphatic hydrocarbon group.

Furthermore, the above-mentioned component (A1) (polymer) may also include a structural unit (a4) that is different from the aforementioned structural units (a1) to (a3).

Structural Unit (a1):

The structural unit (a1) is a structural unit derived from an acrylate ester that contains an acid dissociable, dissolution inhibiting group.

The acid dissociable, dissolution inhibiting group within the structural unit (a1) has an alkali dissolution inhibiting effect that renders the entire component (A1) insoluble in an alkali developing solution prior to dissociation, and then following dissociation under action of acid, increases the solubility of the entire component (A1) in the alkali developing solution. There are no particular limitations on the acid dissociable, dissolution inhibiting group within the structural unit (a1), and any of the groups that have been proposed as acid dissociable, dissolution inhibiting groups for the base resins of chemically amplified resists can be used. Generally, groups that form either a cyclic or chain-like tertiary alkyl ester with the carboxyl group of the (meth)acrylic acid, and acetal-type acid dissociable, dissolution inhibiting groups such as alkoxyalkyl groups are widely known. Here, the term "(meth)acrylic acid" is a generic term that includes either or both of acrylic acid having a hydrogen atom bonded to the α-position and methacrylic acid having a methyl group bonded to the α-position.

A tertiary alkyl ester describes a structure in which an ester is formed by substituting the hydrogen atom of a carboxyl group with a chain-like or cyclic tertiary alkyl group, and a tertiary carbon atom within the chain-like or cyclic tertiary alkyl group is bonded to the oxygen atom at the terminal of the carbonyloxy group (—C(O)—O—). In this tertiary alkyl ester, the action of acid causes cleavage of the bond between the oxygen atom and the tertiary carbon atom. The chain-like or cyclic alkyl group may have a substituent.

Hereafter, for the sake of simplicity, groups that exhibit acid dissociability as a result of the formation of a tertiary alkyl ester with a carboxyl group are referred to as "tertiary alkyl ester-type acid dissociable, dissolution inhibiting groups".

Examples of tertiary alkyl ester-type acid dissociable, dissolution inhibiting groups include aliphatic branched, acid dissociable, dissolution inhibiting groups and aliphatic cyclic group-containing acid dissociable, dissolution inhibiting groups.

The term "aliphatic branched" refers to a branched structure having no aromaticity. The "aliphatic branched, acid dissociable, dissolution inhibiting group" is not limited to be constituted of only carbon atoms and hydrogen atoms (not limited to hydrocarbon groups), but is preferably a hydrocarbon group. Further, the "hydrocarbon group" may be either saturated or unsaturated, but is preferably saturated.

Examples of the aliphatic branched acid dissociable, dissolution inhibiting group include groups represented by a formula —$C(R^{71})(R^{72})(R^{73})$. In this formula, $R^{71}$ to $R^{73}$ each independently represents a linear alkyl group of 1 to 5 carbon atoms. The group represented by —$C(R^{71})(R^{72})(R^{73})$ preferably contains from 4 to 8 carbon atoms, and specific examples include a tert-butyl group, 2-methyl-2-butyl group, 2-methyl-2-pentyl group, and 3-methyl-3-pentyl group, and a tert-butyl group is particularly desirable.

The term "aliphatic cyclic group" refers to a monocyclic group or polycyclic group that has no aromaticity.

In the aliphatic cyclic group-containing acid dissociable, dissolution inhibiting group, the aliphatic cyclic group may or may not have a substituent. Examples of substituents include lower alkyl groups of 1 to 5 carbon atoms, a fluorine atom, fluorinated lower alkyl groups of 1 to 5 carbon atoms, and an oxygen atom (=O).

The aliphatic cyclic group may be a hydrocarbon group formed solely from carbon and hydrogen (alicyclic group), or a heterocyclic group in which a portion of the carbon atoms that constitute the ring structure of an alicyclic group have been substituted with a hetero atom such as an oxygen atom, a nitrogen atom, or a sulfur atom. The aliphatic cyclic group is preferably an alicyclic group.

The aliphatic cyclic group may be either saturated or unsaturated, although a saturated group is preferred, as such groups exhibit superior transparency to ArF excimer lasers and the like, and also exhibit excellent resolution and depth of focus (DOF) and the like.

The number of carbon atoms within the aliphatic cyclic group is preferably within a range from 5 to 15.

Examples of the aliphatic monocyclic groups include groups in which one or more hydrogen atoms have been removed from a cycloalkane. Specific examples include groups in which one or more hydrogen atoms have been removed from cyclopentane or cyclohexane, and a group in which two hydrogen atoms have been removed from cyclohexane is preferable.

Examples of the aliphatic polycyclic groups include groups in which one or more hydrogen atoms have been removed from a bicycloalkane, tricycloalkane, tetracycloalkane or the like. Specific examples include groups in which one or more hydrogen atoms have been removed from a polycycloalkane such as adamantane, norbornane, isobornane, tricyclodecane or tetracyclododecane.

Of these, groups in which two hydrogen atoms have been removed from adamantane, norbornane or tetracyclododecane are readily available industrially, and are consequently preferred. Of these monocyclic and polycyclic groups, a group in which two hydrogen atoms have been removed from adamantane or norbornane is particularly desirable.

Examples of aliphatic cyclic group-containing acid dissociable, dissolution inhibiting groups include (i) groups having a tertiary carbon atom within the ring structure of an aliphatic cyclic group; and (ii) groups having an aliphatic cyclic group, and a branched alkylene group containing a tertiary carbon atom bonded to the aliphatic cyclic group.

Specific examples of the groups (i) include groups represented by general formulas (1-1) to (1-9) shown below.

Specific examples of the groups (ii) include groups represented by general formulas (2-1) to (2-6) shown below.

[Chemical Formula 5]

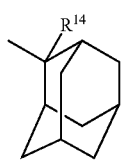
(1-1)

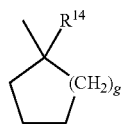
(1-2)

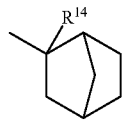
(1-3)

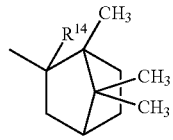
(1-4)

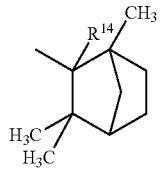
(1-5)

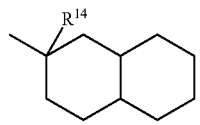
(1-6)

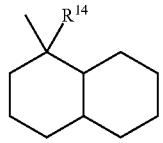
(1-7)

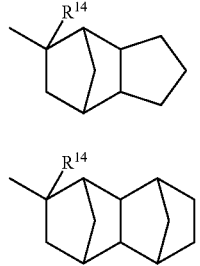
(1-8)

(1-9)

wherein $R^{14}$ represents an alkyl group, and g represents an integer of 0 to 8.

[Chemical Formula 6]

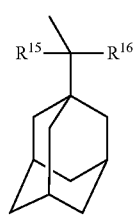
(2-1)

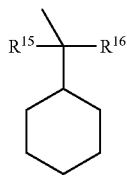
(2-2)

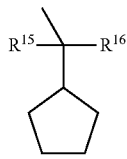
(2-3)

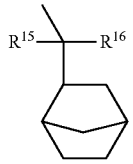
(2-4)

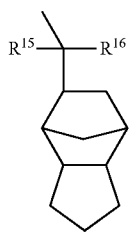
(2-5)

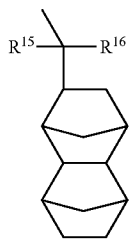
(2-6)

wherein $R^{15}$ and $R^{16}$ each independently represents an alkyl group.

As the alkyl groups of R14 to R16, lower alkyl groups are preferred, and linear or branched alkyl groups are particularly desirable. Specific examples include a methyl group, an ethyl group, a propyl group, an isopropyl group, an n-butyl group, an isobutyl group, a tert-butyl group, a pentyl group, an isopentyl group and a neopentyl group. Of these, a methyl group, an ethyl group or an n-butyl group is preferred, and a methyl group or an ethyl group is particularly desirable.

In general formula (1-2), g is preferably an integer of 0 to 5, more preferably an integer of 1 to 3, and most preferably 1 or 2.

Specific examples of the acid dissociable, dissolution inhibiting group represented by formula (1-2) include a 1-methyl-1-cyclobutyl group, a 1-ethyl-1-cyclobutyl group, a 1-isopropyl-1-cyclobutyl group, a 1-methyl-1-cyclopentyl group, a 1-ethyl-1-cyclopentyl group, a 1-isopropyl-1-cyclopentyl group, a 1-methyl-1-cyclohexyl group, a 1-ethyl-1-cyclohexyl group, a 1-isopropyl-1-cyclohexyl group, a 1-methyl-1-cycloheptyl group, a 1-ethyl-1-cycloheptyl group, a 1-isopropyl-1-cycloheptyl group, a 1-methyl-1-cyclooctyl group and a 1-ethyl-1-cyclooctyl group.

An "acetal-type acid dissociable, dissolution inhibiting group" generally substitutes a hydrogen atom at the terminal of an alkali-soluble group such as a carboxyl group or hydroxyl group, so as to be bonded with an oxygen atom. When acid is generated upon exposure, the generated acid acts to break the bond between the acetal-type acid dissociable, dissolution inhibiting group and the oxygen atom to which the acetal-type, acid dissociable, dissolution inhibiting group is bonded.

Examples of acetal-type acid dissociable, dissolution inhibiting groups include groups represented by general formula (p1) shown below.

[Chemical Formula 7]

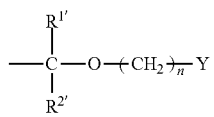
(p1)

wherein Y represents a linear or branched alkyl group or an aliphatic cyclic group; n represents an integer of 0 to 3; $R^{1'}$ and $R^{2'}$ each independently represents a linear or branched alkyl group or a hydrogen atom; and Y and $R^{1'}$ may be bonded to each other to form an aliphatic cyclic group.

In general formula (p1) above, Y represents a linear or branched alkyl group, or an aliphatic cyclic group.

When Y represents a linear or branched alkyl group, it is preferably an alkyl group of 1 to 15 carbon atoms, more preferably an alkyl group of 1 to 5 carbon atoms, still more preferably an ethyl group or a methyl group, and most preferably an ethyl group.

When Y represents an aliphatic cyclic group, as the aliphatic cyclic group, any of the aliphatic monocyclic/polycyclic groups which have been proposed for conventional ArF resists and the like can be appropriately selected for use. For example, the same groups described above in connection with the "aliphatic cyclic group" can be exemplified.

The aliphatic cyclic group for Y preferably has 4 to 15 carbon atoms, more preferably has 4 to 12 carbon atoms, and most preferably has 5 to 10 carbon atoms. Examples thereof include groups in which one or more hydrogen atoms have been removed from a monocycloalkane or a polycycloalkane such as a bicycloalkane, tricycloalkane or tetracycloalkane, which may or may not be substituted with a fluorine atom or a fluorinated alkyl group. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane. Of these, a group in which one or more hydrogen atoms have been removed from adamantane is preferable.

In general formula (p1), n is an integer of 0 to 3, preferably an integer of 0 to 2, more preferably 0 or 1, and most preferably 0.

$R^{1'}$ and $R^{2'}$ each independently represents a linear or branched alkyl group or a hydrogen atom.

As the linear or branched alkyl group for $R^{1'}$ and $R^{2'}$, a lower alkyl group is preferable. As the lower alkyl group, the same as the lower alkyl groups for R described later can be exemplified, and a methyl group or ethyl group is preferable, and a methyl group is particularly desirable.

In the present invention, it is preferable that at least one of $R^{1'}$ and $R^{2'}$ be a hydrogen atom. That is, it is preferable that the group represented by general formula (p1) is a group represented by general formula (p1-1) shown below.

[Chemical Formula 8]

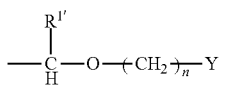

(p1-1)

wherein $R^{1'}$, n and Y are the same as $R^{1'}$, n and Y in general formula (p1) above.

Further, in general formula (p1) above, Y and $R^{1'}$ may be bonded to each other to form an aliphatic cyclic group.

In such a case, an aliphatic cyclic group is formed by Y, $R^{1'}$, —O—$(CH_2)_n$— and the carbon atom having $R^{2'}$ bonded thereto. Such an aliphatic cyclic group is preferably a 4 to 7-membered ring, and more preferably a 4 to 6-membered ring. Specific examples of the aliphatic cyclic group include a tetrahydropyranyl group and a tetrahydrofuranyl group.

As the structural unit (a1), it is preferable to use at least one member selected from the group consisting of structural units represented by formula (a1-0-1) shown below and structural units represented by formula (a1-0-2) shown below.

[Chemical Formula 9]

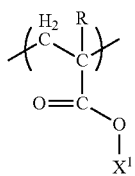

(a1-0-1)

wherein R represents a hydrogen atom, a lower alkyl group or a halogenated lower alkyl group; and $X^1$ represents an acid dissociable, dissolution inhibiting group.

[Chemical Formula 10]

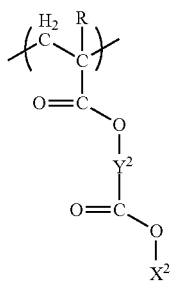

(a1-0-2)

wherein R represents a hydrogen atom, a lower alkyl group or a halogenated lower alkyl group; $X^2$ represents an acid dissociable, dissolution inhibiting group; and $Y^2$ represents a divalent linking group.

In general formula (a1-0-1) shown above, a lower alkyl group and a halogenated lower alkyl group for R are the same as the lower alkyl group and halogenated lower alkyl group which can be bonded to the α-position of the aforementioned acrylate ester.

$X^1$ is not particularly limited as long as it is an acid dissociable, dissolution inhibiting group. Examples thereof include the aforementioned tertiary alkyl ester-type acid dissociable, dissolution inhibiting groups and acetal-type acid dissociable, dissolution inhibiting groups, and tertiary alkyl ester-type acid dissociable, dissolution inhibiting groups are preferable.

In general formula (a1-0-2), R is as defined for R in general formula (a1-0-1) above.

$X^2$ is the same as $X^1$ in general formula (a1-0-1).

As the divalent linking group for $Y^2$, an alkylene group, a divalent aliphatic cyclic group, or a divalent linking group containing a hetero atom is preferable.

When $Y^2$ represents an alkylene group, it preferably has 1 to 10 carbon atoms, more preferably 1 to 6 carbon atoms, still more preferably 1 to 4 carbon atoms, and most preferably 1 to 3 carbon atoms.

When $Y^2$ represents a divalent aliphatic cyclic group, as the aliphatic cyclic group, the same as those exemplified above in connection with the explanation of "aliphatic cyclic group" can be used, except that two or more hydrogen atoms have been removed therefrom. It is particularly desirable that the aliphatic cyclic group be a group in which two or more hydrogen atoms have been removed from cyclopentane, cyclohexane, norbornane, isobornane, adamantane, tricyclodecane or tetracyclododecane.

When $Y^2$ represents a divalent linking group containing a hetero atom, examples of the divalent linking groups containing a hetero atom include —O—, —C(=O)—O—, —C(=O)—, —O—C(=O)—O—, —C(=O)—NH—, —NH— (in the formula, the H may be replaced with a substituent such as an alkyl group or an acyl group), —S—, —S(=O)$_2$—, —S(=O)$_2$—O—, a group represented by formula -A-O—B—, and a group represented by formula -[A-C(=O)—O]$_m$—B—. Here, each of A and B independently represents a divalent hydrocarbon group which may have a substituent, and m represents an integer of 0 to 3.

When $Y^2$ represents a divalent linking group —NH— and the H in the formula is replaced with a substituent such as an alkyl group or an acyl group, the substituent preferably has 1 to 10 carbon atoms, more preferably has 1 to 8 carbon atoms, and most preferably has 1 to 5 carbon atoms.

When $Y^2$ is a group represented by formula -A-O—B— or a group represented by formula -[A-C(=O)—O]$_m$—B—, each of A and B independently represents a divalent hydrocarbon group which may have a substituent.

m is an integer of 0 to 3, preferably an integer of 0 to 2, more preferably 0 or 1, and most preferably 1.

The hydrocarbon group represented by A may be either an aliphatic hydrocarbon group or an aromatic hydrocarbon group. An aliphatic hydrocarbon group refers to a hydrocarbon group having no aromaticity.

The aliphatic hydrocarbon group represented by A may be either saturated or unsaturated, but in general, the aliphatic hydrocarbon group is preferably saturated.

More specific examples of the aliphatic hydrocarbon group represented by A include linear or branched aliphatic hydrocarbon groups, and aliphatic hydrocarbon groups that contain a ring within their structures.

In the "linear or branched aliphatic hydrocarbon group" represented by A, the number of carbon atoms is preferably within a range from 1 to 10, more preferably within a range from 1 to 8, even more preferably within a range from 1 to 5, and most preferably 1 or 2.

As the linear aliphatic hydrocarbon group, linear alkylene groups are preferred, and specific examples include a methylene group, an ethylene group [—$(CH_2)_2$—], a trimethylene group [—$(CH_2)_3$—], a tetramethylene group [—$(CH_2)_4$—] and a pentamethylene group [—$(CH_2)_5$—].

As the branched aliphatic hydrocarbon group, branched alkylene groups are preferred, and specific examples include various alkylalkylene groups, including alkylmethylene groups such as —CH($CH_3$)—, —CH($CH_2CH_3$)—, —C($CH_3$)$_2$—, —C($CH_3$)($CH_2CH_3$)—, —C($CH_3$)($CH_2CH_2CH_3$)— and —C($CH_2CH_3$)$_2$—; alkylethylene groups such as —CH($CH_3$)$CH_2$—, —CH($CH_3$)CH($CH_3$)—, —C($CH_3$)$_2CH_2$—, —CH($CH_2CH_3$)$CH_2$— and —C(CH$_2$CH$_3$)$_2$—CH$_2$—; alkyltrimethylene groups such as —CH(CH$_3$)CH$_2$CH$_2$— and —CH$_2$CH(CH$_3$)CH$_2$—; and alkyltetramethylene groups such as —CH(CH$_3$)CH$_2$CH$_2$CH$_2$— and —CH$_2$CH(CH$_3$)CH$_2$CH$_2$—. The alkyl groups within these alkylalkylene groups are preferably linear alkyl groups of 1 to 5 carbon atoms.

The linear aliphatic hydrocarbon groups may or may not have a substituent. Examples of the substituent include a fluorine atom, a fluorinated lower alkyl group of 1 to 5 carbon atoms which is substituted by a fluorine atom, and an oxygen atom (=O).

Examples of the "aliphatic hydrocarbon groups that contain a ring within their structures" represented by A include cyclic aliphatic hydrocarbon groups (groups in which two hydrogen atoms have been removed from an aliphatic hydrocarbon ring), and groups in which this type of cyclic aliphatic hydrocarbon group is either bonded to the terminal of the abovementioned linear aliphatic hydrocarbon group or positioned partway along the linear aliphatic hydrocarbon group.

The cyclic aliphatic hydrocarbon group preferably has 3 to 20 carbon atoms, and more preferably has 3 to 12 carbon atoms.

The cyclic aliphatic hydrocarbon group may be either a polycyclic group or a monocyclic group. As the monocyclic group, a group in which two hydrogen atoms have been removed from a monocycloalkane of 3 to 6 carbon atoms is preferable. Examples of the monocycloalkane include cyclopentane and cyclohexane.

As the polycyclic group, a group in which two hydrogen atoms have been removed from a polycycloalkane of 7 to 12 carbon atoms is preferable. Specific examples of the polycycloalkane include adamantane, norbornane, isobornane, tricyclodecane and tetracyclododecane.

The cyclic aliphatic hydrocarbon groups may or may not have a substituent. Examples of substituents include a lower alkyl group of 1 to 5 carbon atoms, a fluorine atom, a fluorinated lower alkyl group of 1 to 5 carbon atoms which is substituted by a fluorine atom, and an oxygen atom (=O).

The group A is preferably a linear aliphatic hydrocarbon group, more preferably a linear alkylene group, still more preferably a linear alkylene group of 1 to 5 carbon atoms, particularly preferably a methyl group or an ethyl group, and most preferably an ethyl group.

Examples of the hydrocarbon group represented by B include the same divalent hydrocarbon groups as those exemplified above in relation to the hydrocarbon group represented by A.

As the group B, a linear or branched aliphatic hydrocarbon group is preferred, and a methylene group, an ethylene group or an alkylmethylene group is particularly desirable. The alkyl group within the alkylmethylene group is preferably a linear alkyl group of 1 to 5 carbon atoms, is more preferably a linear alkyl group of 1 to 3 carbon atoms, and is most preferably a methyl group.

Further, in the group represented by formula -[A-C(=O)—O]$_m$—B—, m is an integer of 0 to 3, preferably an integer of 0 to 2, more preferably 0 or 1, and most preferably 1.

In the present invention, as the divalent linking group for Y$^2$, a divalent linking group containing a hetero atom is preferable, and a linear group having an oxygen atom as a hetero atom, for example, a group that includes an ester bond is particularly desirable.

Of these divalent linking groups, groups represented by the aforementioned formula -A-O—B— or formula -A-C(=O)—O—B— are preferable, and a group represented by formula —(CH$_2$)$_a$—C(=O)—O—(CH$_2$)$_b$— is particularly desirable.

a represents an integer of 1 to 5, is preferably 1 or 2, and is most preferably 2.

b represents an integer of 1 to 5, is preferably 1 or 2, and is most preferably 1.

Specific examples of the structural unit (a1) include structural units represented by general formulas (a1-1) to (a1-4) shown below.

[Chemical Formula 11]

(a1-1)

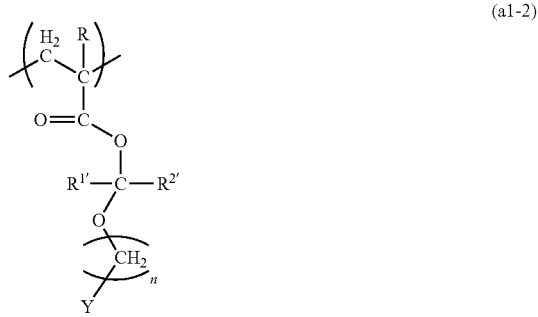

(a1-2)

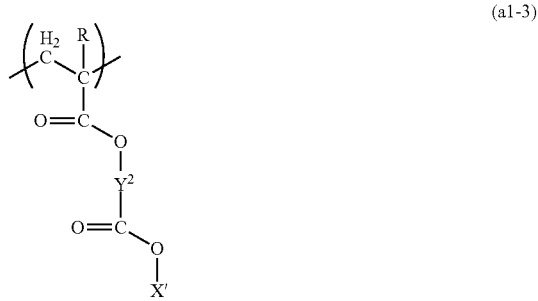

(a1-3)

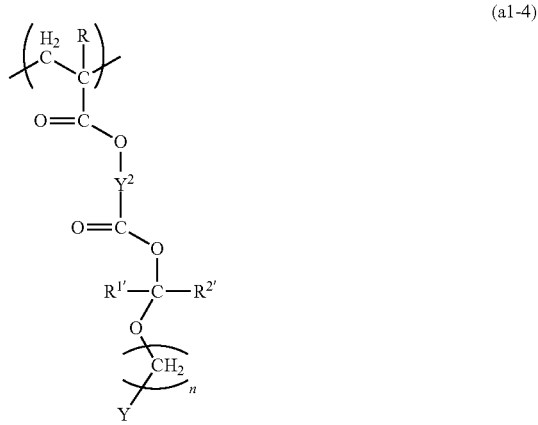

(a1-4)

wherein X' represents a tertiary alkyl ester-type acid dissociable, dissolution inhibiting group; Y represents a lower alkyl group of 1 to 5 carbon atoms or an aliphatic cyclic group; n represents an integer of 0 to 3; Y$^2$ and R represent a hydrogen atom, a lower alkyl group or a halogenated lower alkyl group; and $R^{1'}$ and $R^{2'}$ each independently represent a hydrogen atom or a lower alkyl group of 1 to 5 carbon atoms.

In general formulas (a1-1) to (a1-4), the lower alkyl group and halogenated lower alkyl group for R are the same as the lower alkyl group and halogenated lower alkyl group which can be bonded to the α-position of the aforementioned acrylate ester.

Examples of the tertiary alkyl ester-type acid dissociable, dissolution inhibiting group for X' in the formula above are the same as the above-exemplified tertiary alkyl ester-type acid dissociable, dissolution inhibiting groups for $X^1$.

As $R^{1'}$, $R^{2'}$, n and Y, may be exemplified by the same $R^{1'}$, $R^{2'}$, n and Y as defined for general formula (p1) described above in connection with the "acetal-type acid dissociable, dissolution inhibiting group".

Examples of $Y^2$ include the same divalent linking groups as those exemplified above for $Y^2$ in the above general formula (a1-0-2).

Specific examples of structural units represented by the above general formulas (a1-1) to (a1-4) are shown below.

In the following formulas, Rα represents a hydrogen atom, a methyl group or a trifluoromethyl group.

[Chemical Formula 12]

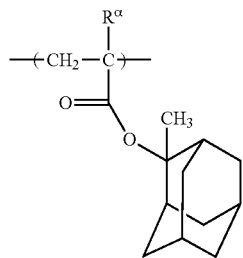
(a1-1-1)

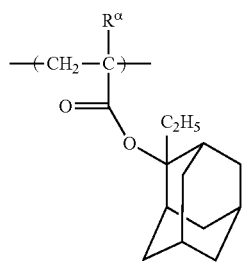
(a1-1-2)

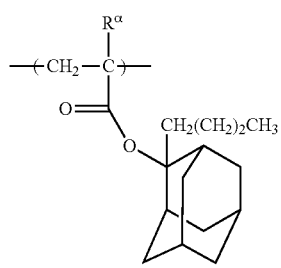
(a1-1-3)

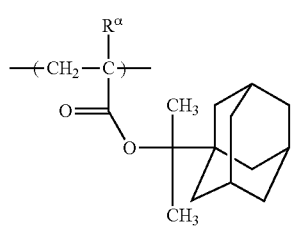
(a1-1-4)

-continued

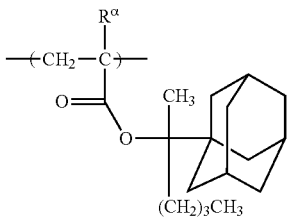
(a1-1-5)

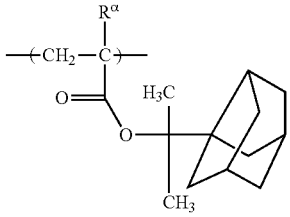
(a1-1-6)

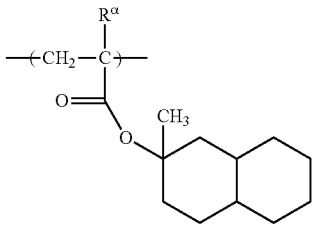
(a1-1-7)

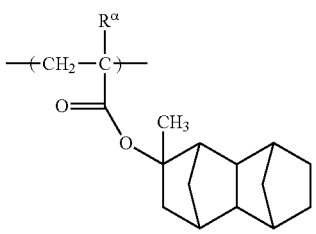
(a1-1-8)

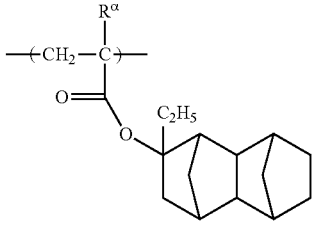
(a1-1-9)

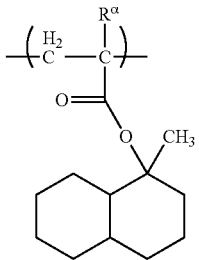
(a1-1-10)

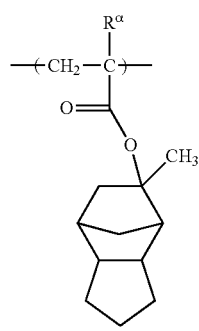
(a1-1-11)
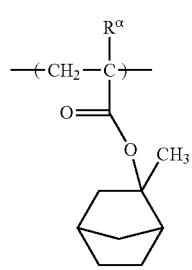
(a1-1-12)
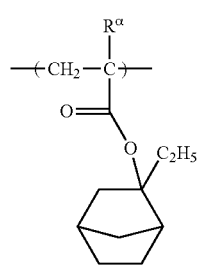
(a1-1-13)
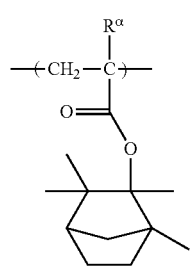
(a1-1-14)
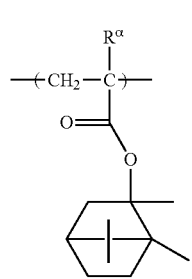
(a1-1-15)
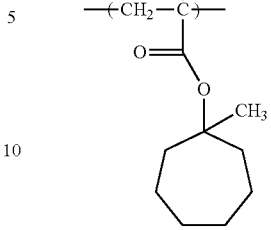
(a1-1-16)
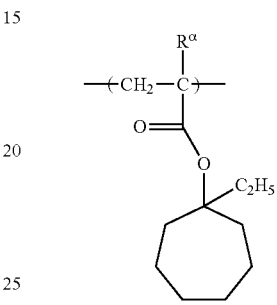
(a1-1-17)
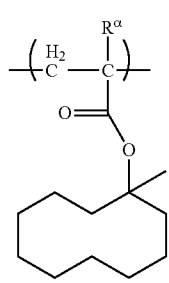
(a1-1-18)
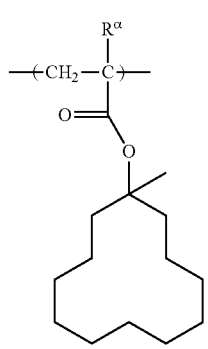
(a1-1-19)
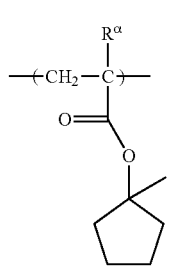
(a1-1-20)

(a1-1-21)
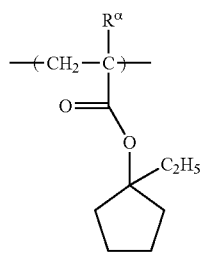
[Chemical Formula 13]
(a1-1-22)
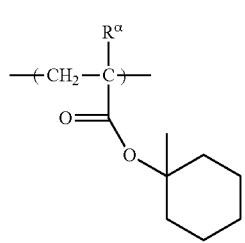
(a1-1-23)
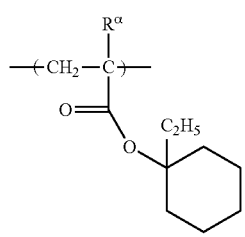
(a1-1-24)
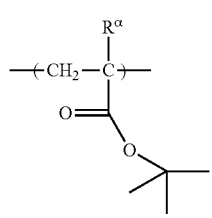
(a1-1-25)
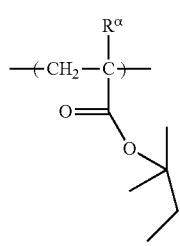
(a1-1-26)
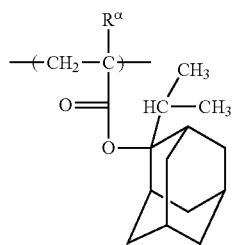
(a1-1-27)
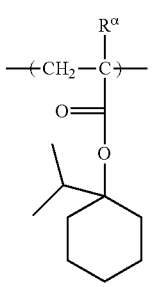
(a1-1-28)
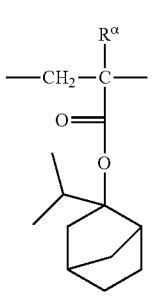
(a1-1-29)
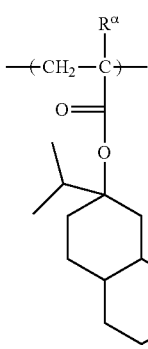
(a1-1-30)
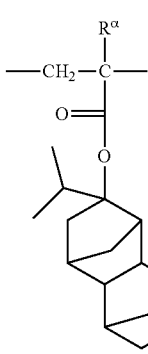
(a1-1-31)
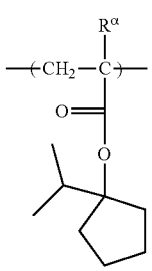

[Chemical Formula 14]
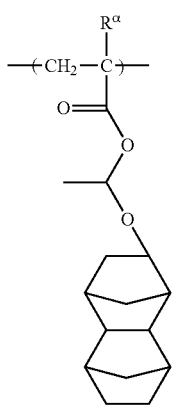 (a1-2-1)
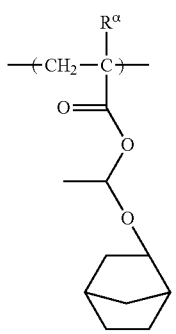 (a1-2-2)
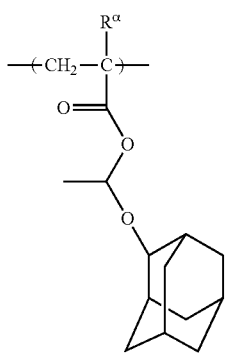 (a1-2-3)
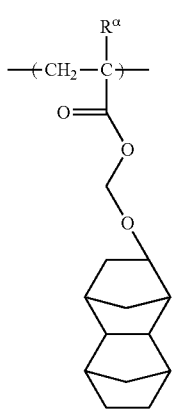 (a1-2-4)
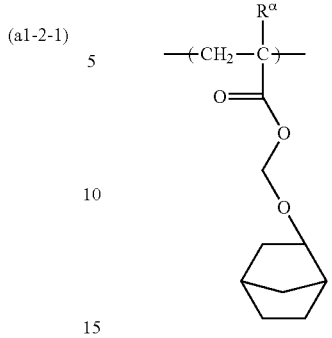 (a1-2-5)
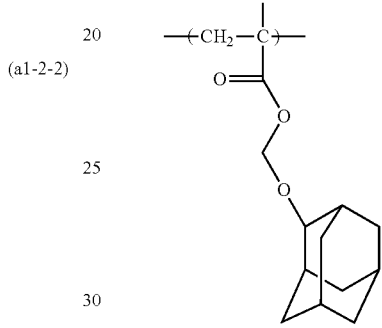 (a1-2-6)
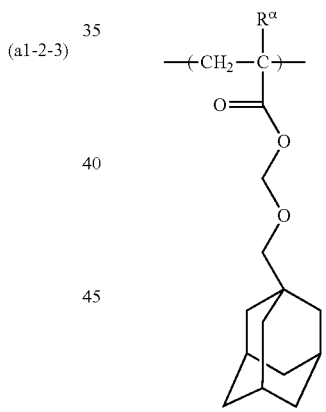 (a1-2-7)
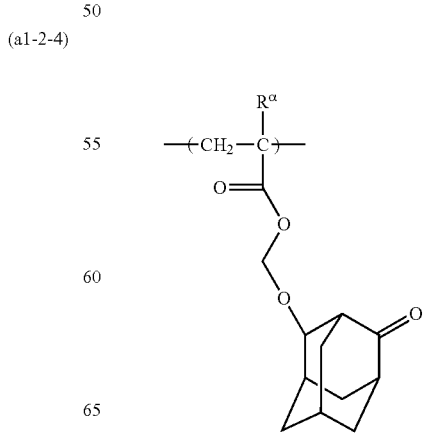 (a1-2-8)

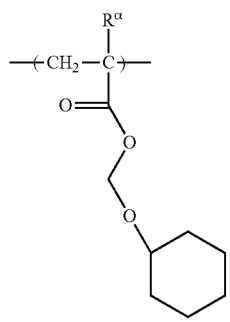
(a1-2-9)
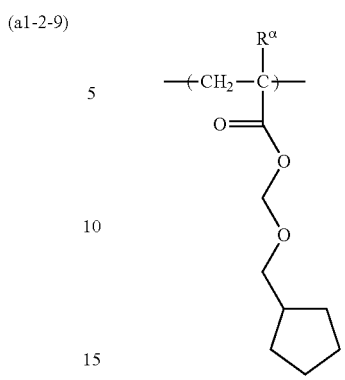
(a1-2-13)
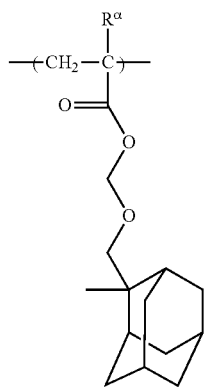
(a1-2-10)
(a1-2-14)
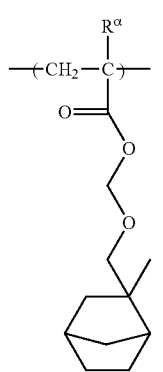
(a1-2-11)
(a1-2-15)
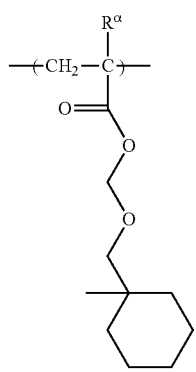
(a1-2-12)
(a1-2-16)

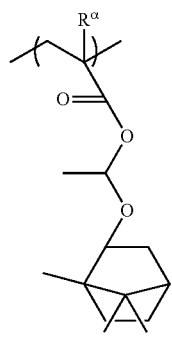
(a1-2-17)
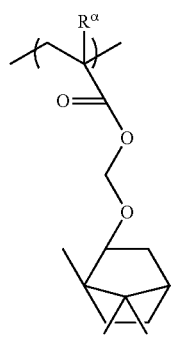
(a1-2-18)
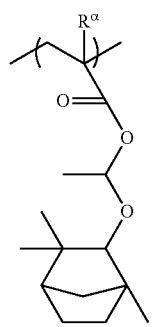
(a1-2-19)
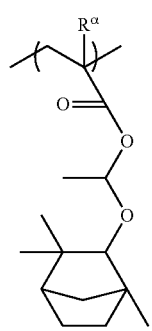
(a1-2-20)
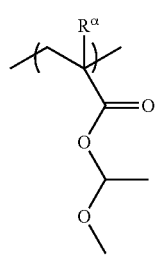
(a1-2-21)
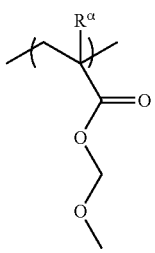
(a1-2-22)
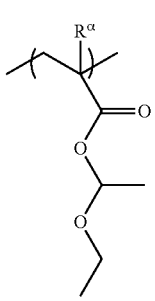
(a1-2-22)
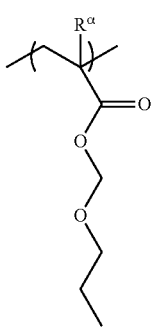
(a1-2-23)
[Chemical Formula 15]
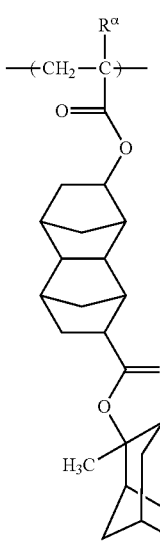
(a1-3-1)

(a1-3-2)
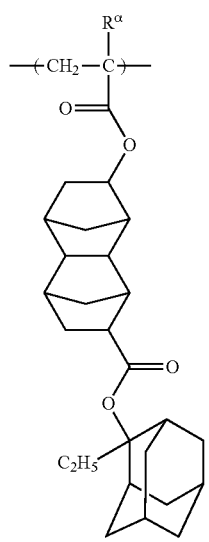
(a1-3-3)
(a1-3-4)
(a1-3-5)
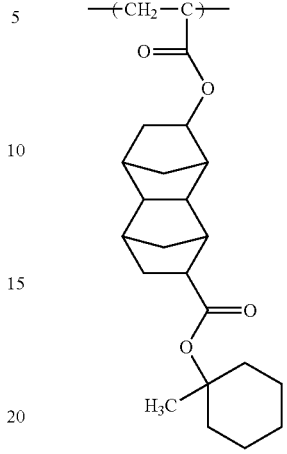
(a1-3-6)
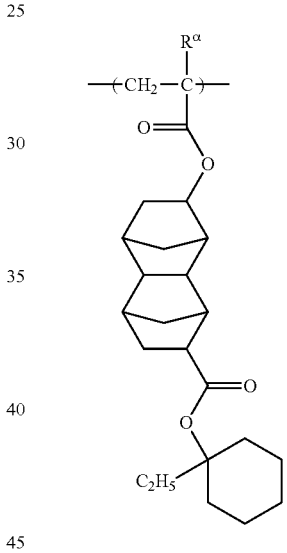
(a1-3-7)
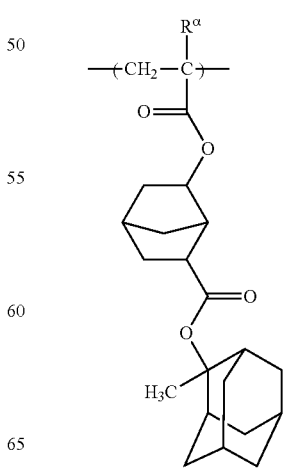

(a1-3-8)

(a1-3-9)

(a1-3-10)

(a1-3-11)

(a1-3-12)

(a1-3-13)

(a1-3-14)

(a1-3-15) 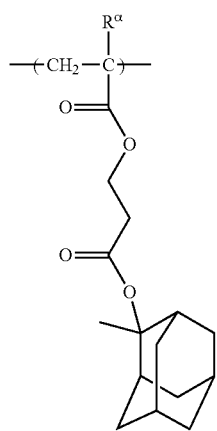
(a1-3-16) 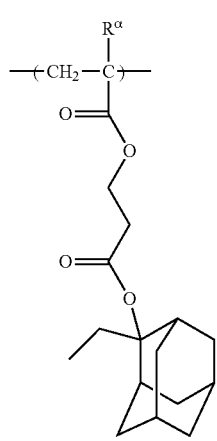
(a1-3-17) 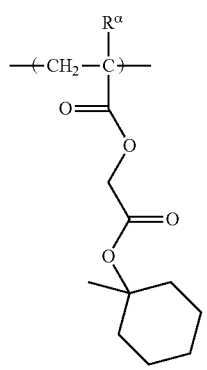
(a1-3-18) 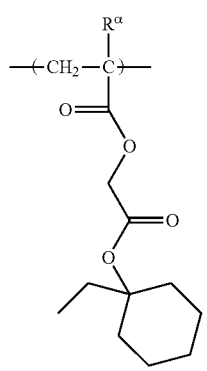
[Chemical Formula 16]
(a1-3-19) 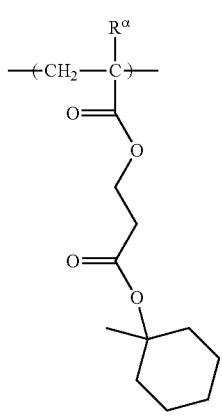
(a1-3-20) 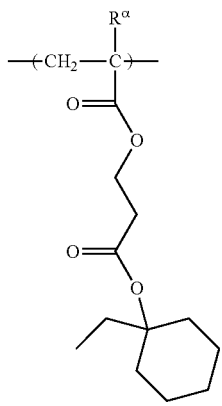
(a1-3-21)
(a1-3-22) 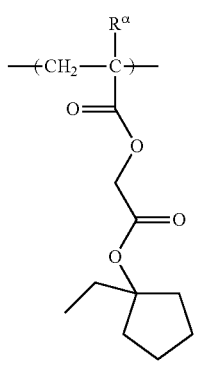

(a1-3-23)
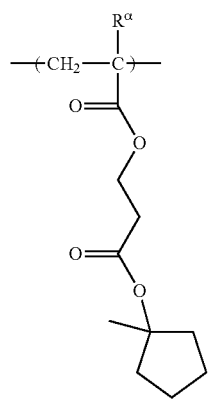
(a1-3-24)
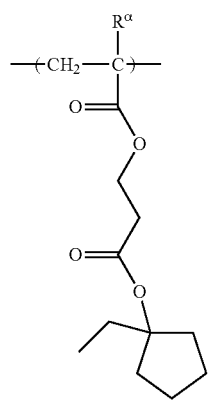
[Chemical Formula 17]
(a1-3-25)
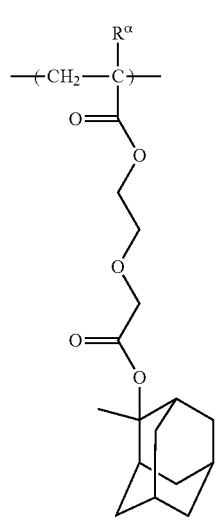
(A1-3-26)
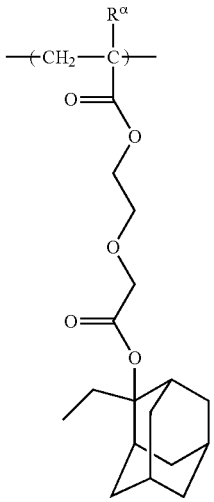
(a1-3-27)
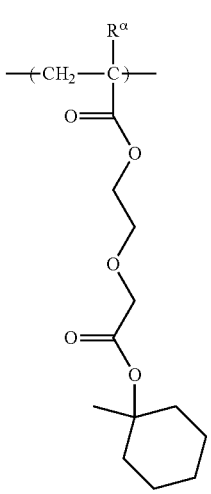
(a1-3-28)
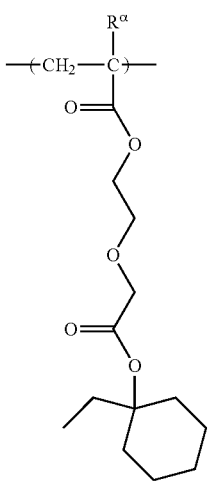

(a1-3-29) 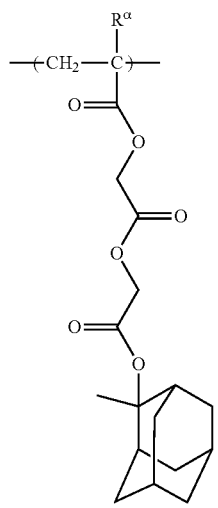
(a1-3-30) 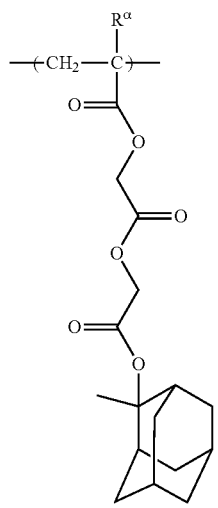
(a1-3-31) 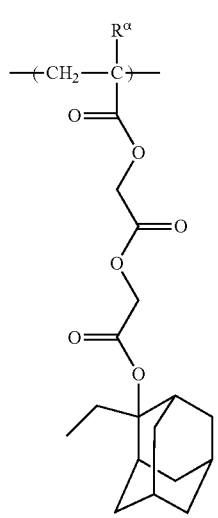
(a1-3-32) 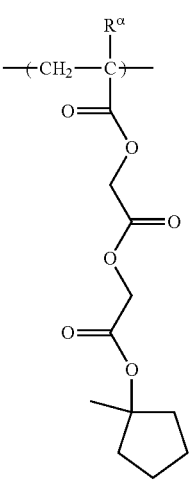
[Chemical Formula 18]
(a1-4-1) 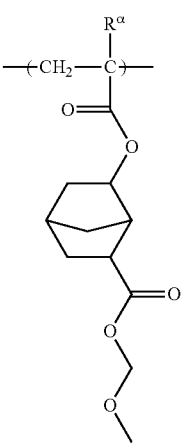
(a1-4-2) 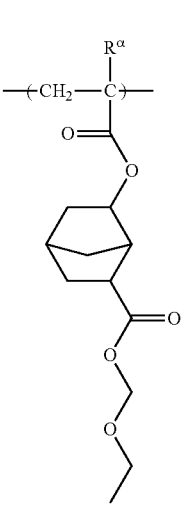

(a1-4-3) 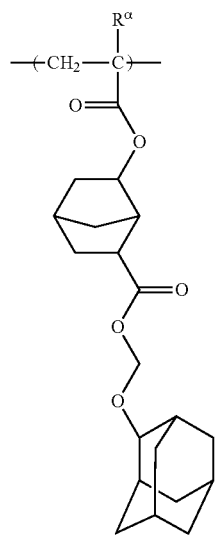
(a1-4-4) 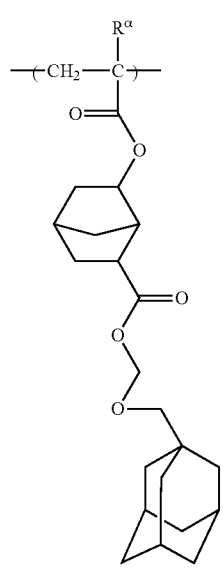
(a1-4-5) 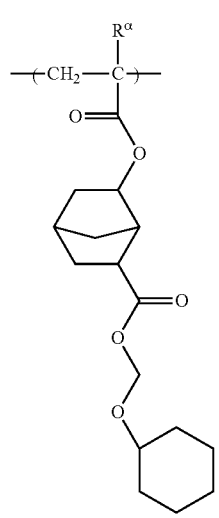
(a1-4-6) 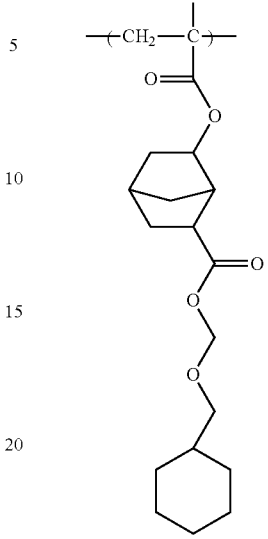
(a1-4-7) 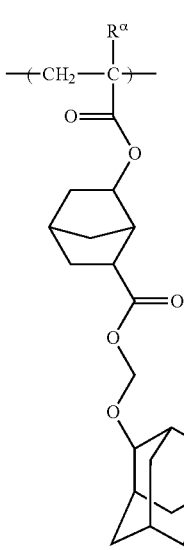
(a1-4-8) 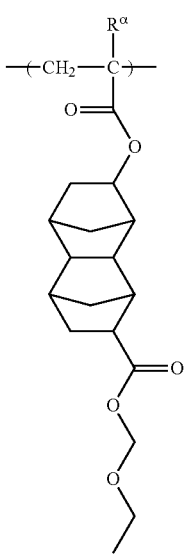

(a1-4-9) 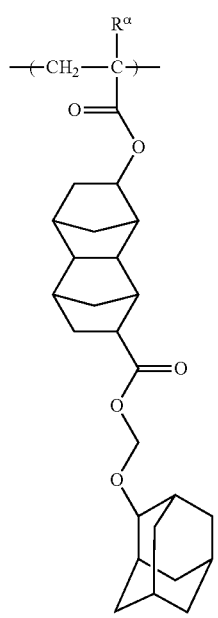
(a1-4-11) 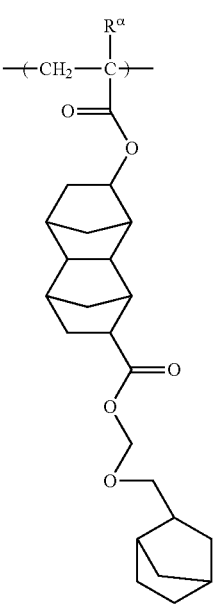
(a1-4-10) 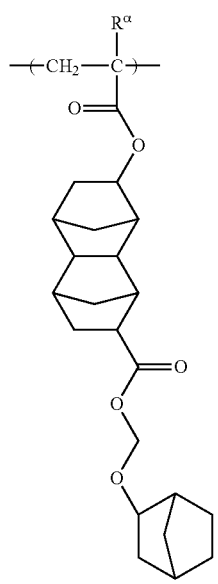
(a1-4-12) 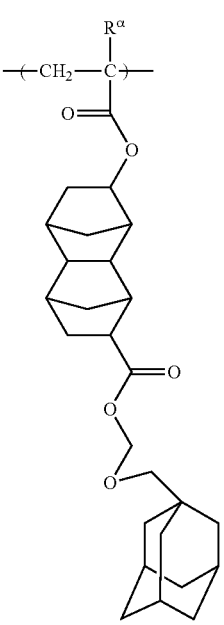

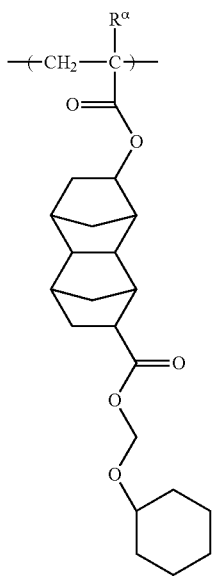

(a1-4-13)

(a1-4-14)

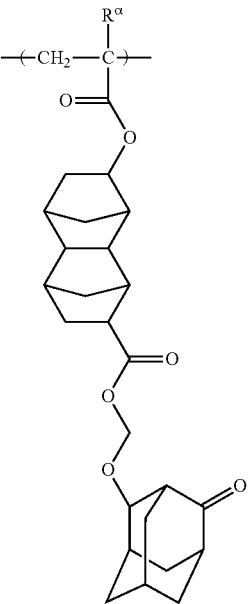

(a1-4-15)

As the structural unit (a1), one type of structural unit may be used alone, or two or more types of structural units may be used in combination.

Of the above, structural units represented by general formula (a1-1) or (a1-3) are preferable. More specifically, at least one structural unit selected from the group consisting of structural units represented by formulas (a1-1-1) to (a-1-1-4), (a1-1-20) to (a1-1-23) and (a1-3-25) to (a1-3-32) is more preferable.

As the structural unit (a1), structural units represented by general formula (a1-1-01) shown below, which include the structural units represented by formulas (a1-1-1) to (a1-1-3), structural units represented by general formula (a1-1-02) shown below, which include the structural units represented by formulas (a1-1-16) to (a1-1-17) and formulas (a1-1-20) to (a1-1-23), structural units represented by general formula (a1-3-01) shown below, which include the structural units represented by formulas (a1-3-25) to (a1-3-26), structural units represented by general formula (a1-3-02) shown below, which include the structural units represented by formulas (a1-3-27) to (a1-3-28), and structural units represented by general formula (a1-3-03) shown below are also preferable.

[Chemical Formula 19]

(a1-1-01)

wherein R represents a hydrogen atom, a lower alkyl group or a halogenated lower alkyl group; and $R^{11}$ represents a lower alkyl group.

[Chemical Formula 20]

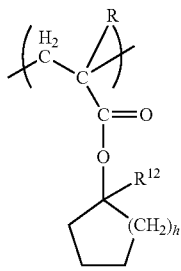

(a1-1-02)

wherein R represents a hydrogen atom, a lower alkyl group or a halogenated lower alkyl group; $R^{12}$ represents a lower alkyl group; and h represents an integer of 1 to 6.

In general formula (a1-1-01), R is as defined for R in general formula (a1-0-1) above. The lower alkyl group for $R^{11}$ is the same as the lower alkyl group for R above, and is preferably a methyl group, an ethyl group or an isopropyl group.

In general formula (a1-1-02), R is as defined for R in general formula (a1-0-1) above. The lower alkyl group for $R^{12}$ is the same as the lower alkyl group for R above. $R^{12}$ is preferably a methyl group or an ethyl group, and most preferably an ethyl group.

h is preferably 1 or 2, and most preferably 2.

[Chemical Formula 21]

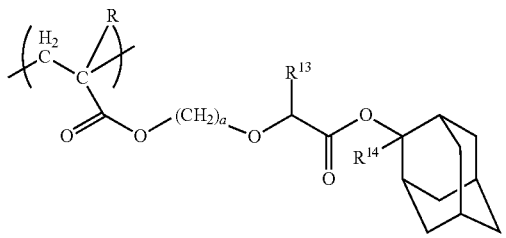

(a1-3-01)

wherein R represents a hydrogen atom, a lower alkyl group or a halogenated lower alkyl group; $R^{14}$ represents a lower alkyl group; $R^{13}$ represents a hydrogen atom or a methyl group; and a represents an integer of 1 to 10.

[Chemical Formula 22]

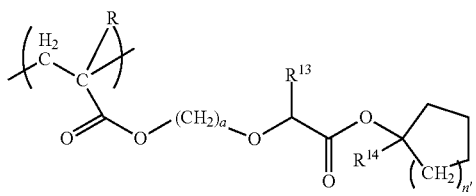

(a1-3-02)

wherein R represents a hydrogen atom, a lower alkyl group or a halogenated lower alkyl group; $R^{14}$ represents a lower alkyl group; $R^{13}$ represents a hydrogen atom or a methyl group; a represents an integer of 1 to 10; and n' represents an integer of 0 to 3.

In the aforementioned general formulas (a1-3-01) and (a1-3-02), R is as defined for R in general formula (a1-3) above.

$R^{13}$ is preferably a hydrogen atom.

The lower alkyl group for $R^{14}$ is the same as the lower alkyl group for R, and is preferably a methyl group or an ethyl group.

a is preferably an integer of 1 to 8, more preferably an integer of 2 to 5, and most preferably 2.

[Chemical Formula 23]

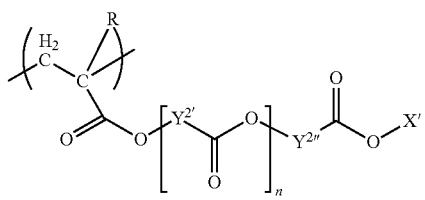

(a1-3-03)

wherein R represents a hydrogen atom, a lower alkyl group or a halogenated lower alkyl group; $Y^{2'}$ and $Y^{2''}$ each independently represents a divalent linking group; X' represents an acid dissociable, dissolution inhibiting group; and n represents an integer of 0 to 3.

In general formula (a1-3-03), R is as defined for R in general formula (a1-3) above.

Examples of the divalent linking group represented by $Y^{2'}$ and $Y^{2''}$ include the same divalent linking groups as those exemplified above for $Y^2$ in the aforementioned general formula (a1-3).

$Y^{2'}$ is preferably a divalent hydrocarbon group that may have a substituent, more preferably a linear aliphatic hydrocarbon group, and still more preferably a linear alkylene group. Of these, a linear alkylene group of 1 to 5 carbon atoms is more preferable, and a methylene group and an ethylene group are most preferable.

$Y^{2''}$ is preferably a divalent hydrocarbon group that may have a substituent, more preferably a linear aliphatic hydrocarbon group, and still more preferably a linear alkylene group. Of these, a linear alkylene group of 1 to 5 carbon atoms is more preferable, and a methylene group and an ethylene group are most preferable.

The acid dissociable, dissolution inhibiting group represented by X' is as defined for X' in general formula (a1-3) above.

X' is preferably a tertiary alkyl ester-type acid dissociable, dissolution inhibiting group, is more preferably an abovementioned group (i) having a tertiary carbon atom within the ring structure of a monovalent aliphatic cyclic group, and is most preferably a group represented by general formula (1-1) above.

n is an integer of 0 to 3, preferably an integer of 0 to 2, more preferably 0 or 1, and most preferably 1.

As the structural unit represented by formula (a1-3-03), structural units represented by general formula (a1-3-03-1) shown below which include the structural units represented by formulas (a1-3-29) and (a1-3-31), and structural units represented by general formula (a1-3-03-2) shown below which includes the structural units represented by formulas (a1-3-30) and (a1-3-32), are particularly desirable.

[Chemical Formula 24]

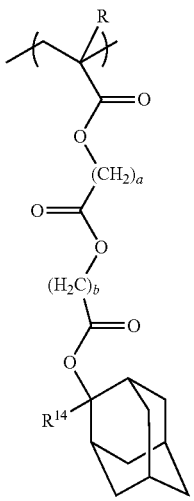
(a1-3-03-1)

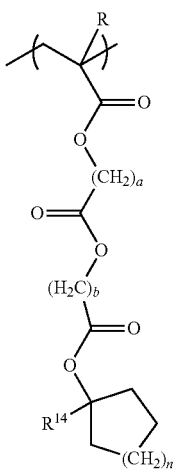
(a1-3-03-2)

wherein R is as defined for R in general formula (a1-3) above; $R^{14}$ is as defined for $R^{14}$ in general formula (a1-3-01) above; a represents an integer of 1 to 10; b represents an integer of 1 to 10; and n represents an integer of 0 to 3.

a is preferably an integer of 1 to 5, and is most preferably 1 or 2.

b is preferably an integer of 1 to 5, and is most preferably 1 or 2.

n is preferably 1 or 2.

In the component (A1), the amount of the structural unit (a1) based on the combined total of all structural units constituting the component (A1) is preferably 10 to 80 mol %, more preferably 20 to 70 mol %, and still more preferably 25 to 50 mol %. By making the amount of the structural unit (a1) at least as large as 10 mol %, a pattern can be easily formed using a resist composition prepared from the component (A1). On the other hand, by making the amount of the structural unit (a1) no more than 80 mol %, a good balance can be achieved with the other structural units.

Structural Unit (a2):

The structural unit (a2) is a structural unit derived from an acrylate ester containing a lactone-containing cyclic group.

The term "lactone-containing cyclic group" refers to a cyclic group including one ring containing a —O—C(O)— structure (lactone ring). The term "lactone ring" refers to a single ring containing a —O—C(O)— structure, and this ring is counted as the first ring. A lactone-containing cyclic group in which the only ring structure is the lactone ring is referred to as a monocyclic group, and groups containing other ring structures are described as polycyclic groups regardless of the structure of the other rings.

When the component (A1) is used in the formation of a resist film, the lactone-containing cyclic group of the structural unit (a2) is effective in improving the adhesion between the resist film and the substrate, and in enhancing the hydrophilicity, thereby increasing the compatibility with the developing solution containing water.

As the structural unit (a2), there is no particular limitation, and an arbitrary structural unit may be used.

Specific examples of lactone-containing monocyclic groups include groups in which one hydrogen atom has been removed from γ-butyrolactone, and groups in which one hydrogen atom has been removed from mevalonic lactone. Further, specific examples of lactone-containing polycyclic groups include groups in which one hydrogen atom has been removed from a lactone ring-containing bicycloalkane, tricycloalkane or tetracycloalkane.

More specifically, examples of the structural unit (a2) include structural units represented by general formulas (a2-1) to (a2-5) shown below.

[Chemical Formula 25]

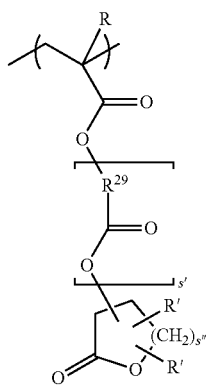
(a2-1)

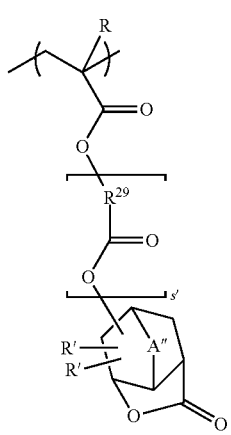
(a2-2)

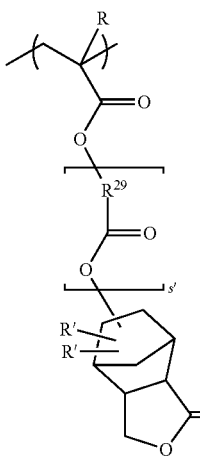
(a2-3)

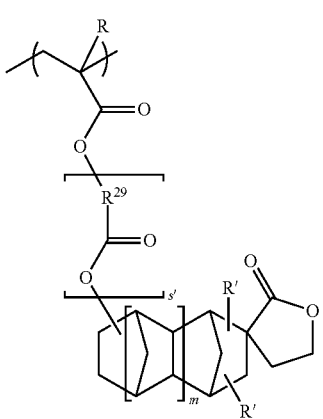
(a2-4)

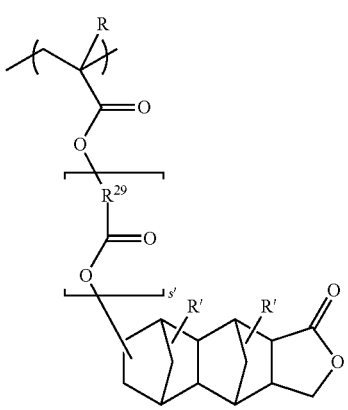
(a2-5)

wherein R represents a hydrogen atom, a lower alkyl group or a halogenated lower alkyl group; each R' represents, independently, a hydrogen atom, an alkyl group of 1 to 5 carbon atoms, an alkoxy group of 1 to 5 carbon atoms or —COOR", wherein each R" represents, independently, a hydrogen atom or a linear, branched or cyclic alkyl group of 1 to 15 carbon atoms; $R^{29}$ represents a divalent linking group; s' represents 0 or 1; s" represents 0 or 1; A" represents an alkylene group of 1 to 5 carbon atoms which may contain an oxygen atom or a sulfur atom; and m represents an integer of 0 or 1.

In general formulas (a2-1) to (a2-5), R is the same as R in the structural unit (a1).

Examples of the alkyl group of 1 to 5 carbon atoms for R' include a methyl group, an ethyl group, a propyl group, an n-butyl group and a tert-butyl group. Examples of the alkoxy group of 1 to 5 carbon atoms for R' include a methoxy group, an ethoxy group, an n-propoxy group, an iso-propoxy group, an n-butoxy group and a tert-butoxy group. In consideration of industrial availability, R' is preferably a hydrogen atom.

When R" is a linear or branched alkyl group, it preferably has 1 to 10 carbon atoms, and more preferably 1 to 5 carbon atoms.

When R" is a cyclic alkyl group, it preferably has 3 to 15 carbon atoms, more preferably 4 to 12 carbon atoms, and most preferably 5 to 10 carbon atoms. Examples thereof include groups in which one or more hydrogen atoms have been removed from a monocycloalkane or a polycycloalkane such as a bicycloalkane, tricycloalkane or tetracycloalkane, and which may or may not be substituted with fluorine atoms or fluorinated alkyl groups. Specific examples include groups in which one or more hydrogen atoms have been removed from a monocycloalkane such as cyclopentane or cyclohexane, and groups in which one or more hydrogen atoms have been removed from a polycycloalkane such as adamantane, norbornane, isobornane, tricyclodecane or tetracyclododecane.

Specific examples of alkylene groups of 1 to 5 carbon atoms which may contain an oxygen atom or a sulfur atom for A" include a methylene group, ethylene group, n-propylene group, isopropylene group, —O—CH$_2$—, —CH$_2$—O—CH$_2$—, —S—CH$_2$— and —CH$_2$—S—CH$_2$—.

Examples of $R^{29}$ include the same divalent linking groups as those exemplified above for $Y^2$ in the above general formula (a1-0-2). As $R^{29}$, an alkylene group is preferable, and a linear or branched alkylene group is more preferable. When $Y^2$ represents an alkylene group, it preferably has 1 to 10 carbon atoms, more preferably 1 to 6 carbon atoms, still more preferably 1 to 4 carbon atoms, and most preferably 1 to 3 carbon atoms.

Specific examples of the linear alkylene group include a methylene group, an ethylene group [—(CH$_2$)$_2$—], a trimethylene group [—(CH$_2$)$_3$—] and a tetramethylene group [—(CH$_2$)$_4$—]. Specific examples of the branched alkylene group include various alkylalkylene groups, including alkylmethylene groups such as —CH(CH$_3$)—, —CH(CH$_2$CH$_3$)—, —C(CH$_3$)$_2$— and —C(CH$_3$)(CH$_2$CH$_3$)—; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$— and —CH$_2$(CH$_2$CH$_3$)CH—; and alkyltrimethylene groups such as —CH(CH$_3$)CH$_2$CH$_2$— and —CH$_2$CH(CH$_3$)CH$_2$—. The alkyl groups within these alkylalkylene groups are preferably alkyl groups of 1 to 2 carbon atoms. As R29, a methylene group is most preferred.

In each of the formulas, s' may be either 0 or 1.

Further, in each of the formulas, s" may be either 0 or 1, but is preferably 1.

Specific examples of structural units represented by the aforementioned general formulas (a2-1) to (a2-5) when s' is 0 are shown below.

In the following formulas, Rα represents a hydrogen atom, a methyl group or a trifluoromethyl group.
[Chemical Formula 26]
(a2-1-1)
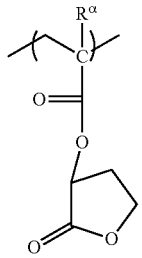
(a2-1-2)
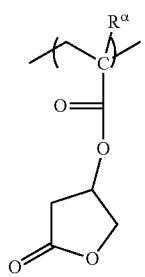
(a2-1-3)
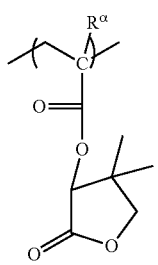
(a2-1-4)
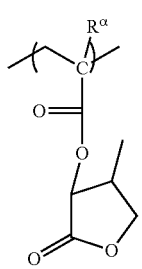
(a2-1-5)
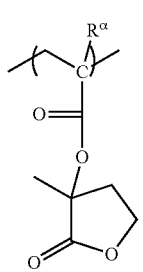
(a2-1-6)
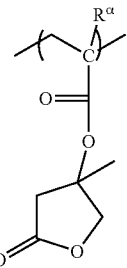
(a2-1-7)
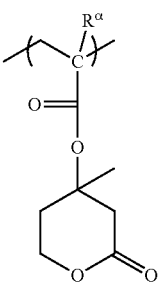
[Chemical Formula 27]
(a2-2-1)
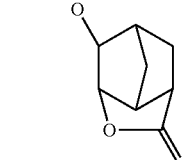
(a2-2-2)
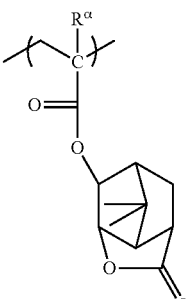
(a2-2-3)
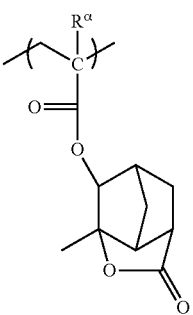

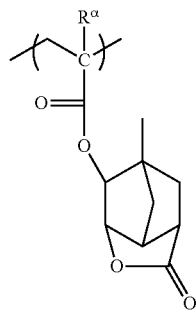 (a2-2-4)
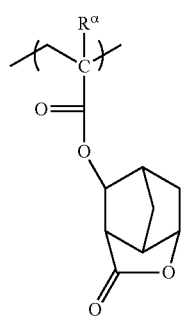 (a2-2-5)
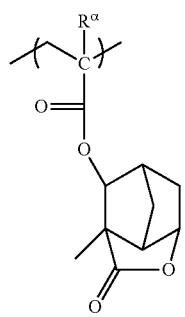 (a2-2-6)
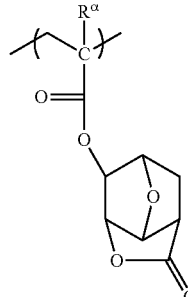 (a2-2-7)
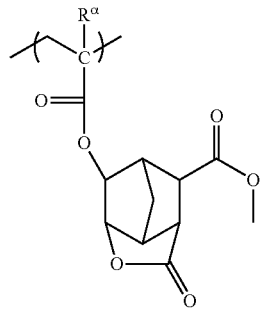 (a2-2-8)
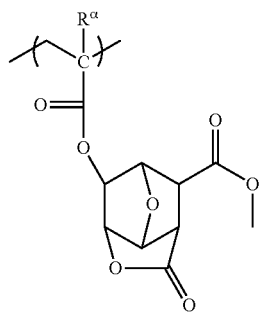 (a2-2-9)
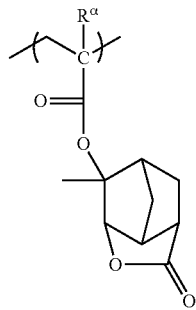 (a2-2-10)
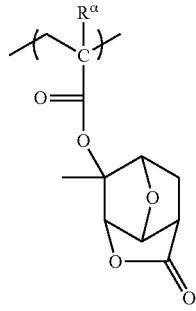 (a2-2-11)
[Chemical Formula 28]
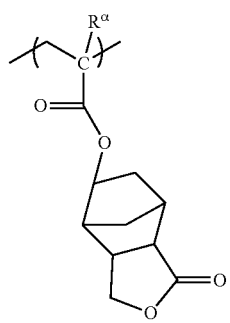 (a2-3-1)
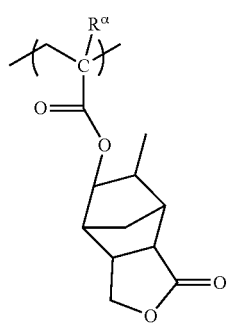 (a2-3-2)

(a2-3-3)
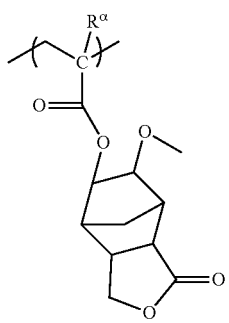
(a2-3-4)
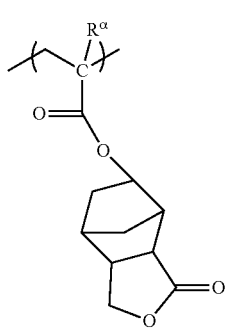
(a2-3-5)
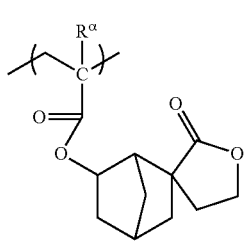
[Chemical Formula 29]
(a2-4-1)
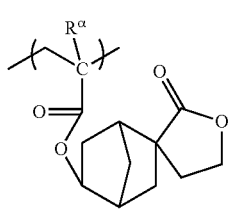
(a2-4-2)
(a2-4-3)
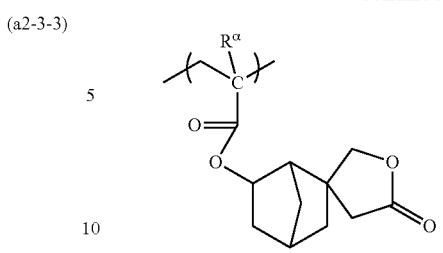
(a2-4-4)
(a2-4-5)
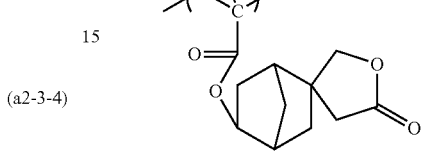
(a2-4-6)
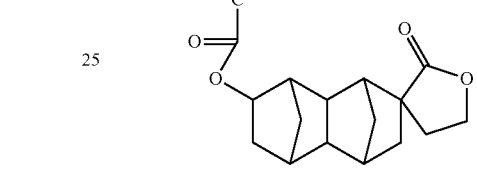
(a2-4-7)
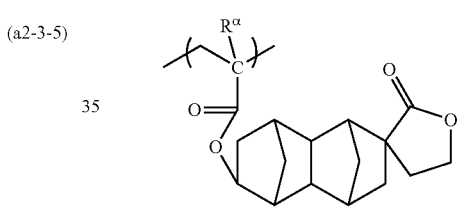
(a2-4-8)
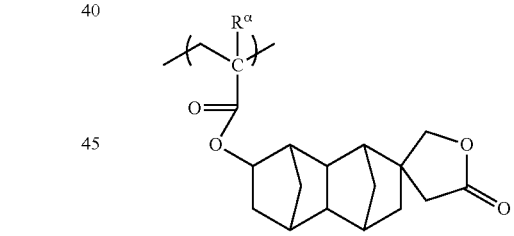
(a2-4-9)
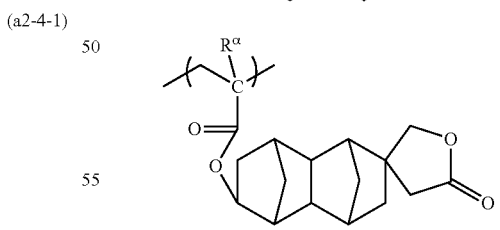
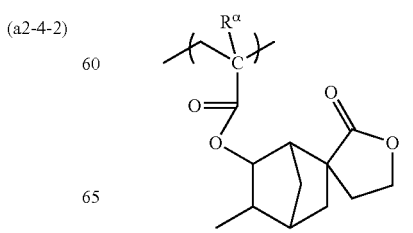

(a2-4-10)

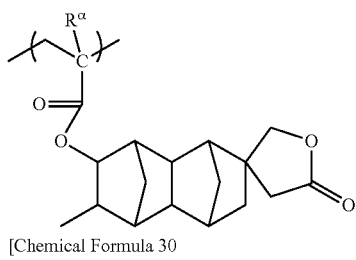

[Chemical Formula 30]

(a2-5-1)

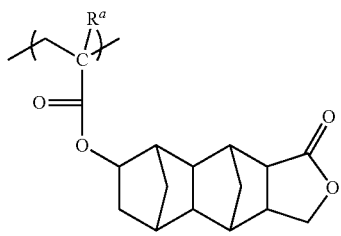

(a2-5-2)

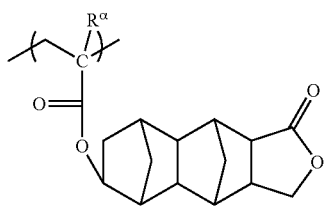

(a2-5-3)

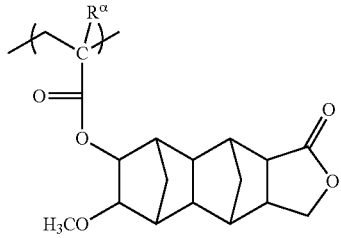

(a2-5-4)

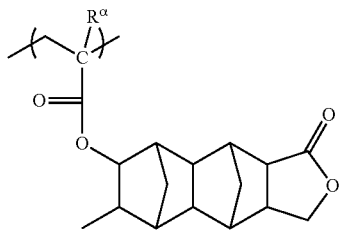

Further, specific examples of preferred structural units represented by the aforementioned general formulas (a2-1) to (a2-5) when s' is 1 include a group in which —$CH_2$—C(=O)—O— or —$C(CH_3)_2$—C(=O)—O— is positioned between the oxygen atom within a carbonyloxy group (—O—) which is bonded to the α-carbon atom and a lactone-containing cyclic group bonded to the oxygen atom in the above formulas.

In the component (A1), as the structural unit (a2), one type of structural unit may be used, or two or more types of structural units may be used in combination.

As the structural unit (a2), at least one structural unit selected from the group consisting of formulas (a2-1) to (a2-5) is preferable, and at least one structural unit selected from the group consisting of formulas (a2-1) to (a2-3) is more preferable. Of these, it is particularly desirable to use at least one structural unit selected from the group consisting of structural units represented by chemical formulas (a2-1-1), (a2-2-1), (a2-2-7), (a2-3-1) and (a2-3-5), and structural units in which —$CH_2$—C(=O)—O— or —$C(CH_3)_2$—C(=O)—O— is positioned between the oxygen atom within a carbonyloxy group (—O—) which is bonded to the α-carbon atom of the above structural units and a lactone-containing cyclic group bonded to the oxygen atom.

In the component (A1), the amount of the structural unit (a2) based on the combined total of all structural units constituting the component (A1) is preferably 5 to 60 mol %, more preferably 10 to 50 mol %, and still more preferably 20 to 50 mol %. By making the amount of the structural unit (a2) at least as large as 5 mol %, the effect of using the structural unit (a2) can be satisfactorily achieved. On the other hand, by making the amount of the structural unit (a2) no more than 60 mol %, a good balance can be achieved with the other structural units.

Structural Unit (a3):

The structural unit (a3) is a structural unit derived from an acrylate ester containing a polar group-containing aliphatic hydrocarbon group.

When the component (A1) includes the structural unit (a3), the hydrophilicity of the component (A) is improved, and hence, the compatibility of the component (A1) with the developing solution is improved. As a result, the alkali solubility of the exposed portions improves, which contributes to favorable improvements in the resolution.

Examples of the polar group include a hydroxyl group, a cyano group, a carboxyl group, or a hydroxyalkyl group in which some of the hydrogen atoms of the alkyl group have been substituted with fluorine atoms (namely, a fluorinated alkyl alcohol), although a hydroxyl group is particularly desirable.

Examples of the aliphatic hydrocarbon group include linear or branched hydrocarbon groups (and preferably alkylene groups) of 1 to 10 carbon atoms, and polycyclic aliphatic hydrocarbon groups (polycyclic groups). These polycyclic groups can be selected appropriately from the multitude of groups that have been proposed for the resins of resist compositions designed for use with ArF excimer lasers. The polycyclic group preferably has 7 to 30 carbon atoms.

Of the various possibilities, structural units derived from an acrylate ester that include an aliphatic polycyclic group that contains a hydroxyl group, a cyano group, a carboxyl group or a hydroxyalkyl group in which some of the hydrogen atoms of the alkyl group have been substituted with fluorine atoms are particularly desirable. Examples of the polycyclic groups include groups in which two or more hydrogen atoms have been removed from a bicycloalkane, tricycloalkane, tetracycloalkane or the like. Specific examples include groups in which two or more hydrogen atoms have been removed from a polycycloalkane such as adamantane, norbornane, isobornane, tricyclodecane or tetracyclododecane. Of these polycyclic groups, groups in which two or more hydrogen atoms have been removed from adamantane, norbornane or tetracyclododecane are preferred industrially.

When the aliphatic hydrocarbon group within the polar group-containing aliphatic hydrocarbon group is a linear or branched hydrocarbon group of 1 to 10 carbon atoms, the structural unit (a3) is preferably a structural unit derived from a hydroxyethyl ester of acrylic acid. On the other hand, when the above-mentioned hydrocarbon group is a polycyclic group, structural units represented by general formula (a3-1) shown below, structural units represented by general formula (a3-2), and structural units represented by general formula (a3-3) are preferable.

[Chemical Formula 31]

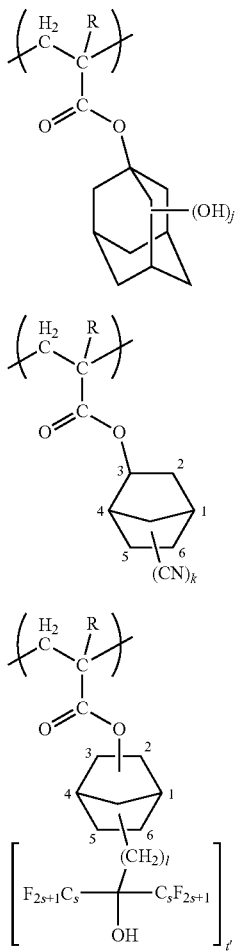

wherein R represents a hydrogen atom, a lower alkyl group or a halogenated lower alkyl group; j represents an integer of 1 to 3; k represents an integer of 1 to 3; t' represents an integer of 1 to 3; l represents an integer of 1 to 5; and s represents an integer of 1 to 3.

In general formulas (a3-1) to (a3-3), the lower alkyl group and halogenated lower alkyl group for R are the same as the lower alkyl group and halogenated lower alkyl group which can be bonded to the α-position of the aforementioned acrylate ester.

In general formula (a3-1), j is preferably 1 or 2, and more preferably 1. When j is 2, it is preferable that the hydroxyl groups be bonded to the 3rd and 5th positions of the adamantyl group. When j is 1, it is preferable that the hydroxyl group be bonded to the 3rd position of the adamantyl group. j is preferably 1, and it is particularly desirable that the hydroxyl group be bonded to the 3rd position of the adamantyl group.

In general formula (a3-2), k is preferably 1. The cyano group is preferably bonded to the 5th or 6th position of the norbonyl group.

In general formula (a3-3), t' is preferably 1, l is preferably 1 and s is preferably 1. Further, in formula (a3-3), it is preferable that a 2-norbonyl group or 3-norbonyl group be bonded to the terminal of the carboxy group of the acrylic acid. The fluorinated alkyl alcohol (—$(CH_2)_l$—$C(C_sF_{2s+1})_2$—OH) is preferably bonded to the 5th or 6th position of the norbonyl group.

As the structural unit (a3), one type of structural unit may be used alone, or two or more types of structural units may be used in combination.

In the component (A1), the amount of the structural unit (a3) based on the combined total of all structural units constituting the component (A1) is preferably 5 to 50 mol %, more preferably 5 to 40 mol %, and still more preferably 5 to 25 mol %.

Structural Unit (a4):

The component (A1) may also have a structural unit (a4) which is other than the above-mentioned structural units (a1) to (a3), as long as the effects of the present invention are not impaired.

As the structural unit (a4), any other structural unit which cannot be classified as one of the above structural units (a1) to (a3) can be used without any particular limitations, and any of the multitude of conventional structural units used within resist resins for ArF excimer lasers or KrF excimer lasers (and particularly for ArF excimer lasers) can be used.

Examples of the structural unit (a4) include a structural unit derived from acrylic acid (hereafter referred to as "structural unit (a4')") and a structural unit which contains a non-acid-dissociable aliphatic polycyclic group and is also derived from an acrylate ester (hereafter referred to as "structural unit (a4")").

With respect to the structural unit (a4'), the term "structural unit derived from acrylic acid" refers to a structural unit which is formed by the cleavage of the ethylenic double bond of acrylic acid.

The term "acrylic acid" is a generic term that includes not only acrylic acid having a hydrogen atom bonded to the carbon atom on the α-position, but also acrylic acid having a substituent (an atom other than a hydrogen atom or a group) bonded to the carbon atom on the α-position. As the substituent, a lower alkyl group or a halogenated lower alkyl group can be mentioned. With respect to the "structural unit derived from acrylic acid", the "α-position (the carbon atom on the α-position)" refers to the carbon atom having the carbonyl group bonded thereto, unless specified otherwise.

In the acrylic acid, the lower alkyl group and halogenated lower alkyl group for the substituent at the α-position are the same as the lower alkyl group and halogenated lower alkyl group for R in the aforementioned structural unit (a1). In the present invention, it is preferable that a hydrogen atom, a lower alkyl group or a halogenated lower alkyl group bonded to the α-position of the acrylic acid, more preferably a hydrogen atom, a lower alkyl group or a fluorinated lower alkyl group. In terms of industrial availability, a hydrogen atom or a methyl group is particularly desirable.

Examples of the aliphatic polycyclic group within the structural unit (a4") include the same groups as those described above in connection with the aforementioned structural unit (a1), and any of the multitude of conventional polycyclic groups used within the resin component of resist compositions for ArF excimer lasers or KrF excimer lasers (and particularly for ArF excimer lasers) can be used. In consideration of industrial availability and the like, at least one polycyclic group selected from amongst a tricyclodecanyl group, an adamantyl group, a tetracyclododecanyl group, an isobornyl group, and a norbornyl group is particularly desirable. These polycyclic groups may be substituted with a linear or branched alkyl group of 1 to 5 carbon atoms.

Specific examples of the structural unit (a4") include units with structures represented by general formulas (a-4-1) to (a-4-5) shown below.

[Chemical Formula 32]

(a4-1)
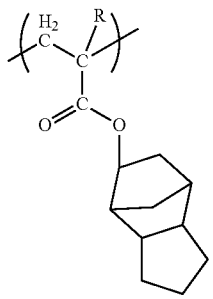

(a4-2)
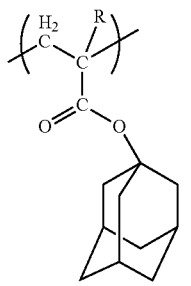

(a4-3)
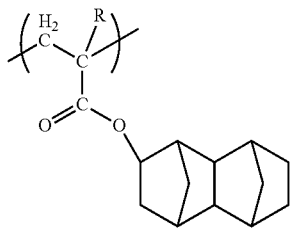

(a4-4)
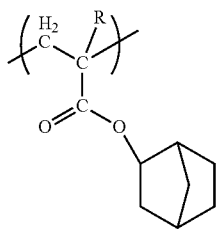

(a4-5)
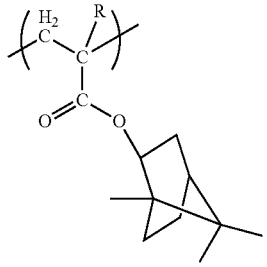

wherein R represents a hydrogen atom, a lower alkyl group or a halogenated lower alkyl group.

In general formulas (a-4-1) to (a-4-5), the lower alkyl group and halogenated lower alkyl group for R are the same as the lower alkyl group and the halogenated lower alkyl group for R of the above-mentioned structural unit (a1).

When the structural unit (a4') is included in the component (A1), the amount of the structural unit (a4') based on the combined total of all the structural units that constitute the component (A1) is preferably within the range from 1 to 15 mol %, and more preferably from 1 to 10 mol %.

When the structural unit (a4") is included in the component (A1), the amount of the structural unit (a4") based on the combined total of all the structural units that constitute the component (A1) is preferably within the range from 1 to 30 mol %, and more preferably from 10 to 20 mol %.

The component (A1) is preferably a copolymer having the structural units (a1), (a2) and (a3). Examples of such a copolymer include a copolymer consisting of the structural units (a1), (a2) and (a3), and a copolymer consisting of the structural units (a1), (a2), (a3) and (a4).

In the component (A), as the component (A1), one type may be used alone, or two or more types may be used in combination.

The weight average molecular weight (Mw) (the polystyrene equivalent value determined by gel permeation chromatography) of the component (A1) is not particularly limited, but is preferably 2,000 to 50,000, more preferably 3,000 to 30,000, and most preferably 5,000 to 20,000. By making the weight average molecular weight no more than 50,000, the component (A1) exhibits satisfactory solubility in a resist solvent when used as a resist. On the other hand, by making the weight average molecular weight at least as large as 2,000, dry etching resistance and cross-sectional shape of the resist pattern becomes satisfactory.

Further, the dispersity (Mw/Mn) is preferably 1.0 to 5.0, more preferably 1.0 to 3.0, and most preferably 1.2 to 2.5. Here, Mn is the number average molecular weight.

The component (A1) can be obtained, for example, by a conventional radical polymerization or the like of the monomers corresponding with each of the structural units, using a radical polymerization initiator such as azobisisobutyronitrile (AIBN).

Furthermore, in the component (A1), by using a chain transfer agent such as HS—$CH_2$—$CH_2$—$CH_2$—$C(CF_3)_2$—OH, a —$C(CF_3)_2$—OH group can be introduced at the terminals of the component (A 1). Such a copolymer having introduced a hydroxyalkyl group in which some of the hydrogen atoms of the alkyl group are substituted with fluorine atoms is effective in reducing developing defects and LER (line edge roughness: unevenness of the side walls of a line pattern).

[Component (A2)]

As the component (A2), a low molecular compound is preferable, which has a molecular weight of at least 500 and less than 2,000, and contains an acid dissociable, dissolution inhibiting group exemplified above in connection with the component (A1) and a hydrophilic group. Specific examples include compounds containing a plurality of phenol skeletons in which a part of the hydrogen atoms within hydroxyl groups have been substituted with the aforementioned acid dissociable, dissolution inhibiting groups.

Preferred examples of the component (A2) include low molecular weight phenolic compounds that are known, for example, as sensitizers or heat resistance improvers for use in non-chemically amplified g-line or i-line resists, wherein some of the hydrogen atoms within hydroxyl group of these compounds have been substituted with the acid dissociable, dissolution inhibiting groups exemplified above, and any of these compounds may be used.

Examples of these low molecular weight phenolic compounds include bis(4-hydroxyphenyl)methane, bis(2,3,4-trihydroxyphenyl)methane, 2-(4-hydroxyphenyl)-2-(4'-hydroxyphenyl)propane, 2-(2,3,4-trihydroxyphenyl)-2-(2',3',4'-trihydroxyphenyl)propane, tris(4-hydroxyphenyl)methane, bis(4-hydroxy-3,5-dimethylphenyl)-2-hydroxyphenylmethane, bis(4-hydroxy-2,5-dimethylphenyl)-2-hydroxyphenylmethane, bis(4-hydroxy-3,5-dimethylphenyl)-3,4-dihydroxyphenylmethane, bis(4- hydroxy-2,5-dimethylphenyl)-3,4-dihydroxyphenylmethane, bis(4-hydroxy-3-methylphenyl)-3,4-dihydroxyphenylmethane, bis(3-cyclohexyl-4-hydroxy-6-methylphenyl)-4-hydroxyphenylmethane, bis(3-cyclohexyl-4-hydroxy-6-methylphenyl)-3,4-dihydroxyphenylmethane, 1-[1-(4-hydroxyphenyl)isopropyl]-4-[1,1-bis(4-hydroxyphenyl)ethyl]benzene, and dimers, trimers and tetramers of formalin condensation products of phenols such as phenol, m-cresol, p-cresol and xylenol. Needless to say, the low molecular weight phenolic compound is not limited to these examples.

Also, there are no particular limitations on the acid dissociable, dissolution inhibiting group, and suitable examples include the groups described above.

As the component (A2), one type may be used alone, or two or more types may be used in combination.

As the component (A), one type may be used alone, or two or more types may be used in combination.

As the component (A), it is preferable to use one containing the component (A1).

In the resist composition of the present invention, the amount of the component (A) can be appropriately adjusted depending on the thickness of the resist film to be formed, and the like.

<Component (B)>

The component (B) includes an acid generator (B1) (hereafter, referred to as "component (B1)") consisting of a compound represented by general formula (b1-11) shown below.

[Chemical Formula 33]

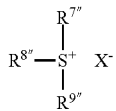
(b1-11)

wherein $R^{7'''}$ to $R^{9'''}$ each independently represent an aryl group or an alkyl group, wherein two of $R^{7'''}$ to $R^{9'''}$ may be bonded to each other to form a ring with the sulfur atom, and at least one of $R^{7'''}$ to $R^{9'''}$ represents a substituted aryl group having a group represented by general formula (I) shown below as a substituent; and $X^-$ represents an anion.

[Chemical Formula 34]

—O—$R^f$ (I)

wherein $R^f$ represents a fluorinated alkyl group.

In general formula (b1-11), the aryl group for $R^{7'''}$ to $R^{9'''}$ may be an unsubstituted aryl group having no substituent or a substituted aryl group in which a part or all of the hydrogen atoms of the aforementioned unsubstituted aryl group has been substituted with substituents.

Examples of the unsubstituted aryl group include an aryl group having 6 to 20 carbon atoms. The aryl group preferably has 6 to 10 carbon atoms because it can be synthesized at a low cost. As the aryl group, a phenyl group or a naphthyl group is particularly desirable.

Examples of the substituent for the substituted aryl group include a group represented by general formula (I) above, an alkyl group, an alkoxy group, an ether group, a halogen atom, a halogenated alkyl group, and a hydroxyl group.

In general formula (I), examples of the fluorinated alkyl group for $R^f$ include groups in which part or all of the hydrogen atoms within the below described unsubstituted alkyl groups have been substituted with a fluorine atom.

The unsubstituted alkyl group may be any of linear, branched or cyclic. Alternatively, the unsubstituted alkyl group may be a combination of a linear or branched alkyl group with a cyclic alkyl group.

The unsubstituted linear alkyl group preferably has 1 to 20 carbon atoms, more preferably 1 to 10 carbon atoms, and still more preferably 1 to 8 carbon atoms. Specific examples include a methyl group, an ethyl group, an n-propyl group, an n-butyl group, an n-pentyl group, an n-hexyl group, an n-heptyl group, an n-octyl group, an n-nonyl group and an n-decanyl group.

The unsubstituted branched alkyl group preferably has 3 to 20 carbon atoms, more preferably 3 to 10 carbon atoms, and still more preferably 3 to 8 carbon atoms. As the branched alkyl group, a tertiary alkyl group is preferable.

As an example of an unsubstituted cyclic alkyl group, a group in which one hydrogen atom has been removed from a monocycloalkane or a polycycloalkane such as a bicycloalkane, tricycloalkane or tetracycloalkane can be given. Specific examples include monocycloalkyl groups such as a cyclopentyl group and a cyclohexyl group; and polycycloalkyl groups such as an adamantyl group, a norbornyl group, an isobornyl group, a tricyclodecanyl group and a tetracyclododecanyl group.

Examples of the combination of a linear or branched alkyl group with a cyclic alkyl group include groups in which a cyclic alkyl group as a substituent is bonded to a linear or branched alkyl group, and groups in which a linear or branched alkyl group as a substituent is bonded to a cyclic alkyl group.

As the above-mentioned unsubstituted alkyl group, a linear or branched alkyl group is preferable, and a linear alkyl group is particularly desirable.

The fluorinated alkyl group for $R^f$ may be either a group in which part of the hydrogen atoms within the aforementioned unsubstituted alkyl group has been substituted with a fluorine atom, or a group in which all of the hydrogen atoms within an unsubstituted alkyl group described below has been substituted with a fluorine atom (i.e., a perfluoroalkyl group).

The fluorinated alkyl group has 2 or more carbon atoms, and the carbon atom that is adjacent to the oxygen atom (—O—) in general formula (I) preferably has no fluorine atoms bonded thereto, whereas the carbon atom at the terminal of $R^f$ preferably has a fluorine atom bonded thereto.

As the fluorinated alkyl group, a linear or branched fluorinated alkyl group is preferable, and a group represented by general formula (I-1) shown below is particularly desirable.

[Chemical Formula 35]

(I-1)

wherein $R^{10'''}$ represents a linear or branched alkylene group, and $R^{11'''}$ represents a linear or branched perfluoroalkyl group.

In formula (I-1), the alkylene group for $R^{10'''}$ may be linear or branched, and is preferably linear. Further, the number of carbon atoms within the alkylene group is preferably within a range from 1 to 10, and more preferably within a range from 3 to 5. Specific examples of the alkylene group for $R^{10'''}$ include groups in which one hydrogen atom has been removed from the alkyl groups exemplified above as unsubstituted linear alkyl groups and unsubstituted branched alkyl groups. As $R^{10'''}$, a propylene group is particularly desirable.

The perfluoroalkyl group for $R^{11'''}$ may be linear or branched, and is preferably linear. Further, the number of carbon atoms within the perfluoroalkyl group is preferably within a range from 1 to 10, and more preferably within a range from 1 to 4. As $R^{11'''}$, a nonafluoro-n-butyl group is particularly desirable.

As the group represented by formula (I-1), a group represented by formula $-(CH_2)_e-(CF_2)_f-CF_3$ is particularly desirable (wherein e represents an integer of 1 to 10, and is preferably an integer of 3 to 5; f represents an integer of 0 to 9, and is preferably an integer of 0 to 3; and e+f is preferably an integer of 2 to 19, and is more preferably an integer of 4 to 7).

The alkyl group as the substituent for the aforementioned substituted aryl group is preferably an alkyl group of 1 to 5 carbon atoms, and a methyl group, an ethyl group, a propyl group, an n-butyl group or a tert-butyl group is particularly desirable.

The alkoxy group as the substituent for the aforementioned substituted aryl group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the ether group as the substituent for the aforementioned substituted aryl group include a group represented by formula $-R^{01}-O-R^{02}$ (wherein $R^{01}$ represents an alkylene group and $R^{02}$ represents an alkyl group).

The alkylene group for $R^{01}$ may be linear, branched or cyclic, and is preferably linear or branched. Further, the number of carbon atoms within the alkylene group is preferably within a range from 1 to 10, and more preferably within a range from 1 to 5. Specific examples of the alkylene group include groups in which one hydrogen atom has been removed from the alkyl groups exemplified above as unsubstituted alkyl groups.

The alkyl group for $R^{02}$ may be linear, branched or cyclic, and is preferably linear or branched. Further, the number of carbon atoms within the alkyl group is preferably within a range from 1 to 10, and more preferably within a range from 1 to 5. More specifically, as the alkyl group, groups the same as the unsubstituted alkyl groups exemplified above can be mentioned.

Preferred examples of the halogen atom as the substituent for the aforementioned substituted aryl group include a fluorine atom and a chlorine atom, and a fluorine atom is particularly desirable.

Examples of the halogenated alkyl group as the substituent for the aforementioned substituted aryl group include groups in which part of or all of the hydrogen atoms of the aforementioned alkyl groups exemplified above as substituents have been substituted with halogen atoms. As the halogen atom within the halogenated alkyl group, an atom the same as the halogen atoms exemplified above as substituents can be mentioned. As the halogenated alkyl group, a fluorinated alkyl group is particularly desirable.

The alkyl group for $R^{7'''}$ to $R^{9'''}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

When two of $R^{7'''}$ to $R^{9'''}$ are bonded to each other to form a ring with the sulfur atom, it is preferable that the two of $R^{7'''}$ to $R^{9'''}$ form a 3 to 10-membered ring including the sulfur atom, and it is particularly desirable that the two of $R^{7'''}$ to $R^{9'''}$ form a 5 to 7-membered ring including the sulfur atom.

When two of $R^{7'''}$ to $R^{9'''}$ are bonded to each other to form a ring with the sulfur atom, the remaining one of $R^{7'''}$ to $R^{9'''}$ is preferably an aryl group. The aryl group is preferably a substituted aryl group having a group represented by general formula (I) above as a substituent.

In the present invention, at least one of $R^{7'''}$ to $R^{9'''}$ represents a substituted aryl group having a group represented by general formula (I) above as a substituent (hereafter, referred to as a substituted aryl group (I)).

The number of groups represented by general formula (I) above included in one substituted aryl group (I) is preferably within a range from 1 to 3, and is most preferably 1.

Further, in the substituted aryl group (I), the aryl group to which the group represented by formula (I) bonds is preferably a phenyl group or a naphthyl group, and a phenyl group is particularly desirable. In this case, the group represented by formula (I) preferably bonds to the para position of the phenyl group.

The substituted aryl group (I) may also include another substituent other than the group represented by formula (I). Examples of the other substituent include an alkyl group, an alkoxy group, an ether group, a halogen atom, a halogenated alkyl group, and a hydroxyl group. These include the same substituents as those described above with respect to the substituents for the substituted aryl group.

The number of other substituents included in one substituted aryl group (I) is preferably within a range from 0 to 2.

One, two or all three of $R^{7'''}$ to $R^{9'''}$ may be a substituted aryl group (I). However, it is most preferable that only one of $R^{7'''}$ to $R^{9'''}$ be a substituted aryl group (I).

In this case, it is preferable that the remaining two of $R^{7'''}$ to $R^{9'''}$ either represent an aryl group that may have another substituent other than the group represented by formula (I), or be bonded to each other to form a ring with the sulfur atom.

When the remaining two of $R^{7'''}$ to $R^{9'''}$ represent an aryl group that may have a substituent, the aryl group is preferably an unsubstituted aryl group, more preferably a phenyl group or a naphthyl group, and most preferably a phenyl group.

Specific examples of preferred cation moiety of the component (B1) are shown below.

[Chemical Formula 36]

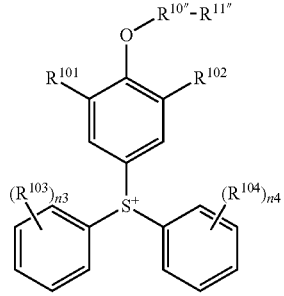

(b1-c-1)

-continued

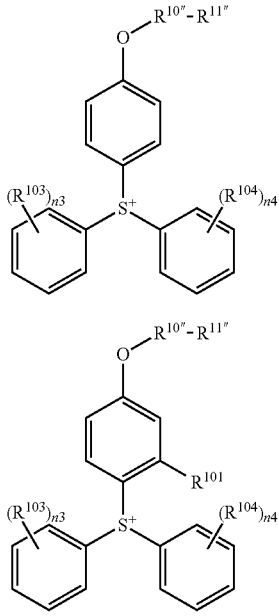

(b1-c-2)

(b1-c-3)

wherein $R^{10'''}$ and $R^{11'''}$ are as defined above for $R^{10'''}$ and $R^{11'''}$ respectively in general formula (I-1), $R^{101}$ to $R^{104}$ each independently represents an alkyl group or an alkoxy group, and n3 and n4 each independently represents an integer of 0 to 5.

In formulas (b1-c-1) to (b1-c-3), as the alkyl group and alkoxy group for $R^{101}$ to $R^{104}$, the same alkyl group and alkoxy group as those described above as the substituents for the substituted aryl group can be mentioned.

In formula (b1-11), there is no particular limitation on the anion for X$^-$, and any anion moiety can be appropriately selected for use which is known as an anion moiety of an onium salt-based acid generator.

Preferred examples of the anion for X$^-$ include an anion represented by general formula (x-1) shown below.

[Chemical Formula 37]

$$R^{4'''}\text{—}SO_3^- \quad\quad (x\text{-}1)$$

wherein $R^{4'''}$ represents an alkyl group, a halogenated alkyl group, an aryl group or an alkenyl group which may have a substituent.

The alkyl group for $R^{4'''}$ may be a linear, branched or cyclic alkyl group.

The linear or branched alkyl group preferably has 1 to 10 carbon atoms, more preferably 1 to 8 carbon atoms, and most preferably 1 to 4 carbon atoms.

The cyclic alkyl group preferably has 4 to 20 carbon atoms, more preferably 4 to 15 carbon atoms, still more preferably 4 to 10 carbon atoms, and most preferably 6 to 10 carbon atoms.

Examples of the halogenated alkyl group for $R^{4'''}$ include groups in which some or all of the hydrogen atoms of an above-mentioned linear, branched or cyclic alkyl group have been substituted with halogen atoms. Examples of the halogen atom include a fluorine atom, a chlorine atom, a bromine atom and an iodine atom, and a fluorine atom is particularly desirable.

In the halogenated alkyl group, the percentage of the number of halogen atoms based on the total number of halogen atoms and hydrogen atoms (halogenation ratio (%)) is preferably 10 to 100%, more preferably 50 to 100%, and most preferably 100%. Higher halogenation ratios are preferred, as they result in increased acid strength.

The aryl group for $R^{4'''}$ is preferably an aryl group of 6 to 20 carbon atoms.

The alkenyl group for $R^{4'''}$ is preferably an alkenyl group of 2 to 10 carbon atoms.

With respect to $R^{4'''}$, the expression "may have a substituent" means that part of or all of the hydrogen atoms within the alkyl group, the halogenated alkyl group, the aryl group or the alkenyl group may be substituted with a substituent (an atom other than a hydrogen atom or a group).

The number of substituents within $R^{4'''}$ may be either 1, or 2 or greater.

Examples of the substituent include a halogen atom, a hetero atom, an alkyl group, an oxygen atom (=O), and a group represented by formula Z-Q$^1$- [wherein Q$^1$ represents a divalent linking group containing an oxygen atom, and Z represents a hydrocarbon group of 3 to 30 carbon atoms which may have a substituent].

Examples of the halogen atom include the same halogen atoms as those described above with respect to the halogenated alkyl group for $R^{4'''}$.

Examples of the alkyl group include the same alkyl groups as those described above for $R^{4'''}$.

Examples of the hetero atom include an oxygen atom, a nitrogen atom, and a sulfur atom.

In the group represented by formula Z-Q$^1$-, Q$^1$ represents a divalent linking group containing an oxygen atom.

Q$^1$ may include another atom other than the oxygen atom. Examples of the atom other than the oxygen atom include a carbon atom, a hydrogen atom, a sulfur atom and a nitrogen atom.

Examples of the divalent linking groups containing an oxygen atom include non-hydrocarbon, oxygen atom-containing linking groups such as an oxygen atom (an ether bond; —O—), an ester bond (—C(=O)—O—), an amide bond (—C(=O)—NH—), a carbonyl group (—C(=O)—) and a carbonate bond (—O—C(=O)—O—); and combinations of the aforementioned non-hydrocarbon, oxygen atom-containing linking groups with an alkylene group.

Specific examples of the combinations of the aforementioned non-hydrocarbon, oxygen atom-containing linking groups and an alkylene group include —R$^{91}$—O—, —R$^{92}$—O—C(=O)—, —C(=O)—O—R$^{93}$—O—C(=O)—, —O—R$^{93}$—O—C(=O)— and —R$^{92}$—O—C(=O)—R$^{93}$—O—C(=O)— (wherein each of R$^{91}$ to R$^{93}$ independently represents an alkylene group).

The alkylene group for R$^{91}$ to R$^{93}$ is preferably a linear or branched alkylene group, and the alkylene group preferably has 1 to 12 carbon atoms, more preferably 1 to 5 carbon atoms, and most preferably 1 to 3 carbon atoms.

Specific examples of the alkylene group include a methylene group [—CH$_2$—]; alkylmethylene groups such as —CH(CH$_3$)—, —CH(CH$_2$CH$_3$)—, —C(CH$_3$)$_2$—, —C(CH$_3$)(CH$_2$CH$_3$)—, —C(CH$_3$)(CH$_2$CH$_2$CH$_3$)— and —C(CH$_2$CH$_3$)$_2$; an ethylene group [—CH$_2$CH$_2$—]; alkylethylene groups such as —CH(CH$_3$)CH$_2$—, —CH(CH$_3$)CH(CH$_3$)—, —C(CH$_3$)$_2$CH$_2$—, —CH(CH$_2$CH$_3$)CH$_2$— and —CH(CH$_2$CH$_3$)CH$_2$—; a trimethylene group (n-propylene group) [—CH$_2$CH$_2$CH$_2$—]; alkyltrimethylene groups such as —CH(CH$_3$)CH$_2$CH$_2$— and —CH$_2$CH(CH$_3$)CH$_2$—; a tetramethylene group [—CH$_2$CH$_2$CH$_2$CH$_2$—]; alkyltetramethylene groups such as —CH(CH$_3$)CH$_2$CH$_2$CH$_2$— and —CH$_2$CH(CH$_3$)CH$_2$CH$_2$—; and a pentamethylene group [—CH$_2$CH$_2$CH$_2$CH$_2$CH$_2$—].

As Q$^1$, a divalent linking group containing an ester bond and/or an ether bond is preferable, and groups represented by formula —O—, —R$^{91}$—O—, —R$^{92}$—O—C(=O)—, —C(=O)—O—, —C(=O)—O—R$^{93}$—, —C(=O)—O—R$^{93}$—O—C(=O)—, —O—R$^{93}$—O—C(=O)— and —R$^{92}$—O—C(=O)—R$^{93}$—O—C(=O)— are particularly desirable.

In the group represented by the formula Z-Q$^1$-, the hydrocarbon group for Z may be either an aromatic hydrocarbon group or an aliphatic hydrocarbon group.

An aromatic hydrocarbon group is a hydrocarbon group having an aromatic ring. The aromatic hydrocarbon group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms. Here, the number of carbon atoms within a substituent(s) is not included in the number of carbon atoms of the aromatic hydrocarbon group.

Specific examples of aromatic hydrocarbon groups include an aryl group which is an aromatic hydrocarbon ring having one hydrogen atom removed therefrom, such as a phenyl group, a biphenyl group, a fluorenyl group, a naphthyl group, an anthryl group or a phenanthryl group; and an arylalkyl group such as a benzyl group, a phenethyl group, a 1-naphthylmethyl group, a 2-naphthylmethyl group, a 1-naphthylethyl group, or a 2-naphthylethyl group. The alkyl chain within the arylalkyl group preferably has 1 to 4 carbon atoms, more preferably 1 to 2 carbon atoms, and most preferably 1 carbon atom.

The aromatic hydrocarbon group may have a substituent. For example, a part of the carbon atoms constituting the aromatic ring within the aromatic hydrocarbon group may be substituted with a hetero atom, or a hydrogen atom bonded to the aromatic ring within the aromatic hydrocarbon group may be substituted with a substituent.

In the former example, a heteroaryl group in which a part of the carbon atoms constituting the ring within the aforementioned aryl group has been substituted with a hetero atom such as an oxygen atom, a sulfur atom or a nitrogen atom, and a heteroarylalkyl group in which a part of the carbon atoms constituting the aromatic hydrocarbon ring within the aforementioned arylalkyl group has been substituted with the aforementioned hetero atom can be used.

In the latter example, as the substituent for the aromatic hydrocarbon group, an alkyl group, an alkoxy group, a halogen atom, a halogenated alkyl group, a hydroxyl group, an oxygen atom (=O), —COOR", —OC(=O)R", a hydroxyalkyl group, a cyano group or the like can be used. The above-mentioned R" represents a hydrogen atom or a linear, branched or cyclic alkyl group of 1 to 15 carbon atoms.

The alkyl group as the substituent for the aromatic hydrocarbon group is preferably an alkyl group of 1 to 5 carbon atoms, and a methyl group, an ethyl group, a propyl group, an n-butyl group or a tert-butyl group is particularly desirable.

The alkoxy group as the substituent for the aromatic hydrocarbon group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom as the substituent for the aromatic hydrocarbon group include a fluorine atom, a chlorine atom, a bromine atom and an iodine atom, and a fluorine atom is preferable.

Examples of the halogenated alkyl group as the substituent for the aromatic hydrocarbon group include a group in which a part of or all of the hydrogen atoms within the aforementioned alkyl group have been substituted with the aforementioned halogen atoms.

R" within the group —COOR" or —OC(=O)R" as the substituent for the aromatic hydrocarbon group is as defined above for R" in the aforementioned structural unit (a2).

Examples of the hydroxyalkyl group as the substituent for the aromatic hydrocarbon group include a group in which at least one hydrogen atom of the aforementioned alkyl groups exemplified above as substituents has been substituted with a hydroxyl group.

The aromatic hydrocarbon group for Z is preferably an aryl group which may have a substituent, an arylalkyl group or a heteroaryl group.

As the aryl group, an unsubstituted aryl group or an aryl group having a halogen atom as a substituent (namely, a halogenated aryl group) is preferable, and a phenyl group, a naphthyl group or a fluorinated phenyl group is particularly desirable.

As the arylalkyl group, one in which an alkyl group is a methyl group is preferable, and a naphthylmethyl group or a benzyl group is particularly desirable.

As the heteroaryl group, one containing a nitrogen atom as a hetero atom is preferable, and a group in which one hydrogen atom has been removed from pyridine is particularly desirable.

The aliphatic hydrocarbon group for Z may be a saturated aliphatic hydrocarbon group or an unsaturated aliphatic hydrocarbon group, or may also be a combination thereof. Further, the aliphatic hydrocarbon group may be any of linear, branched or cyclic.

In the aliphatic hydrocarbon group for Z, a part of the carbon atoms constituting the aliphatic hydrocarbon group may be substituted with a substituent group containing a hetero atom, or a part or all of the hydrogen atoms constituting the aliphatic hydrocarbon group may be substituted with a substituent group containing a hetero atom.

As the "hetero atom" for Z, there is no particular limitation as long as it is an atom other than a carbon atom and a hydrogen atom, and examples thereof include a halogen atom, an oxygen atom, a sulfur atom and a nitrogen atom. Examples of the halogen atom include a fluorine atom, a chlorine atom, an iodine atom and a bromine atom.

The substituent group containing a hetero atom may consist solely of the above-mentioned hetero atom, or may be a group containing a group or atom other than the above-mentioned hetero atom.

Specific examples of the substituent group for substituting a part of the carbon atoms include —O—, —C(=O)—O—, —C(=O)—, —O—C(=O)—O—, —C(=O)—NH—, —NH— (the H may be replaced with a substituent such as an alkyl group or an acyl group), —S—, —S(=O)$_2$— and —S(=O)$_2$—O—. When the aliphatic hydrocarbon group is cyclic, the aliphatic hydrocarbon group may contain these substituent groups in the ring structure.

Examples of the substituent group for substituting a part or all of the hydrogen atoms include an alkoxy group, a halogen atom, a halogenated alkyl group, a hydroxyl group, an oxygen atom (=O) and a cyano group.

The aforementioned alkoxy group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom include a fluorine atom, a chlorine atom, a bromine atom and an iodine atom, and a fluorine atom is preferable.

Examples of the aforementioned halogenated alkyl group include a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

As the aliphatic hydrocarbon group, a linear or branched saturated hydrocarbon group, a linear or branched monovalent unsaturated hydrocarbon group, a cyclic aliphatic hydrocarbon group (aliphatic cyclic group), or a combination thereof is preferable.

The linear saturated hydrocarbon group (alkyl group) preferably has 1 to 20 carbon atoms, more preferably 1 to 15 carbon atoms, and most preferably 1 to 10 carbon atoms. Specific examples include a methyl group, an ethyl group, a propyl group, a butyl group, a pentyl group, a hexyl group, a heptyl group, an octyl group, a nonyl group, a decanyl group, an undecyl group, a dodecyl group, a tridecyl group, an isotridecyl group, a tetradecyl group, a pentadecyl group, a hexadecyl group, an isohexadecyl group, a heptadecyl group, an octadecyl group, a nonadecyl group, an icosyl group, a henicosyl group and a docosyl group.

The branched saturated hydrocarbon group (alkyl group) preferably has 3 to 20 carbon atoms, more preferably 3 to 15 carbon atoms, and most preferably 3 to 10 carbon atoms. Specific examples include a 1-methylethyl group, a 1-methylpropyl group, a 2-methylpropyl group, a 1-methylbutyl group, a 2-methylbutyl group, a 3-methylbutyl group, a 1-ethylbutyl group, a 2-ethylbutyl group, a 1-methylpentyl group, a 2-methylpentyl group, a 3-methylpentyl group and a 4-methylpentyl group.

The unsaturated hydrocarbon group preferably has 2 to 10 carbon atoms, more preferably 2 to 5 carbon atoms, still more preferably 2 to 4 carbon atoms, and most preferably 3 carbon atoms. Examples of linear monovalent unsaturated hydrocarbon groups include a vinyl group, a propenyl group (an allyl group) and a butynyl group. Examples of branched monovalent unsaturated hydrocarbon groups include a 1-methylpropenyl group and a 2-methylpropenyl group.

Among the above-mentioned examples, as the unsaturated hydrocarbon group, a propenyl group is particularly desirable.

The aliphatic cyclic group may be either a monocyclic group or a polycyclic group. The aliphatic cyclic group preferably has 3 to 30 carbon atoms, more preferably 5 to 30 carbon atoms, still more preferably 5 to 20 carbon atoms, still more preferably 6 to 15 carbon atoms, and most preferably 6 to 12 carbon atoms.

Examples thereof include groups in which one or more of the hydrogen atoms have been removed from a monocycloalkane; and groups in which one or more of the hydrogen atoms have been removed from a polycycloalkane such as a bicycloalkane, a tricycloalkane, or a tetracycloalkane. Specific examples include groups in which one or more hydrogen atoms have been removed from a monocycloalkane such as cyclopentane or cyclohexane; and groups in which one or more hydrogen atoms have been removed from a polycycloalkane such as adamantane, norbornane, isobornane, tricyclodecane or tetracyclododecane.

When the aliphatic cyclic group does not contain a hetero atom-containing substituent group in the ring structure thereof, the aliphatic cyclic group is preferably a polycyclic group, more preferably a group in which one or more hydrogen atoms have been removed from a polycycloalkane, and a group in which one or more hydrogen atoms have been removed from adamantane is particularly desirable.

When the aliphatic cyclic group contains a hetero atom-containing substituent group in the ring structure thereof, the hetero atom-containing substituent group is preferably —O—, —C(=O)—O—, —S—, —S(=O)$_2$— or —S(=O)$_2$—O—. Specific examples of such aliphatic cyclic groups include groups represented by formulas (L1) to (L5) and (S1) to (S4) shown below.

[Chemical Formula 38]

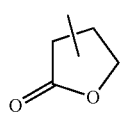
(L1)

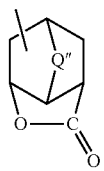
(L2)

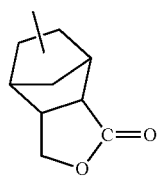
(L3)

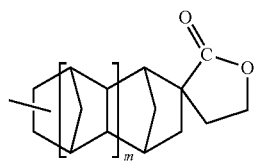
(L4)

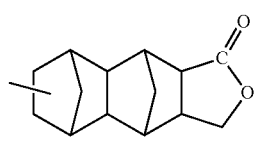
(L5)

(S1)

(S2)

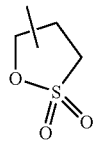
(S3)

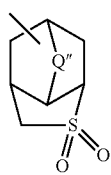
(S4)

wherein Q″ represents an alkylene group of 1 to 5 carbon atoms, —O—, —S—, —O—$R^{94}$— or —S—$R^{95}$— (wherein each of $R^{94}$ and $R^{95}$ independently represents an alkylene group of 1 to 5 carbon atoms); and m represents an integer of 0 or 1.

In the formula above, as the alkylene group for Q″, $R^{94}$ and $R^{95}$, the same alkylene groups as those described above for $R^{91}$ to $R^{93}$ can be used.

In these aliphatic cyclic groups, a part of the hydrogen atoms bonded to the carbon atoms constituting the ring structure may be substituted with a substituent. Examples of substituents include an alkyl group, an alkoxy group, a halogen atom, a halogenated alkyl group, a hydroxyl group and an oxygen atom (=O).

As the alkyl group, an alkyl group of 1 to 5 carbon atoms is preferable, and a methyl group, an ethyl group, a propyl group, an n-butyl group or a tert-butyl group is particularly desirable.

As the alkoxy group and the halogen atom, the same groups as the aforementioned substituent groups for substituting a part or all of the hydrogen atoms can be used.

In the present invention, Z preferably includes a cyclic group which may have a substituent. The cyclic group may be an aromatic hydrocarbon group which may have a substituent or an aliphatic cyclic group which may have a substituent, and an aliphatic cyclic group which may have a substituent is preferable.

The aromatic hydrocarbon group is preferably a naphthyl group which may have a substituent or a phenyl group which may have a substituent.

As the aliphatic cyclic group which may have a substituent, an aliphatic polycyclic group which may have a substituent is preferable. As the aliphatic polycyclic group, the aforementioned groups in which one or more hydrogen atoms have been removed from polycycloalkanes, the aforementioned groups represented by formulas (L2) to (L5) and (S3) to (S4), and the like are preferable.

In the present invention, $R^{4″}$ preferably has a group represented by formula Z-$Q^1$- as a substituent. In this case, $R^{4″}$ is preferably a group represented by formula Z-$Q^1$-$Y^1$- (wherein $Q^1$ and Z are the same as defined above for $Q^1$ and Z in the aforementioned formula Z-$Q^1$-; and $Y^1$ represents an alkylene group of 1 to 4 carbon atoms which may have a substituent, or a fluorinated alkylene group of 1 to 4 carbon atoms which may have a substituent).

That is, $X^-$ is preferably an anion represented by general formula (x-1) shown below.

[Chemical Formula 39]

(x-11)

wherein $Q^1$ represents a divalent linking group containing an oxygen atom; Z represents a hydrocarbon group of 3 to 30 carbon atoms which may have a substituent; and $Y^1$ represents an alkylene group of 1 to 4 carbon atoms which may have a substituent, or a fluorinated alkylene group of 1 to 4 carbon atoms which may have a substituent.

In formula (x-11), Z and $Q^1$ are the same as defined above for Z and $Q^1$ in the aforementioned formula Z-$Q^1$-.

As the alkylene group for $Y^1$, the same alkylene groups as those described above for $Q^1$ having 1 to 4 carbon atoms can be used.

As the fluorinated alkylene group, groups in which part of or all of the hydrogen atoms in the alkylene groups described above are substituted with fluorine atoms can be used.

Specific examples of $Y^1$ include —$CF_2$—, —$CF_2CF_2$—, —$CF_2CF_2CF_2$—, —$CF(CF_3)CF_2$—, —$CF(CF_2CF_3)$—, —$C(CF_3)_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—, —$CF(CF_2CF_2CF_3)$—, —$C(CF_3)(CF_2CF_3)$—; —CHF—, —$CH_2CF_2$—, —$CH_2CH_2CF_2$—, —$CH_2CF_2CF_2$—, —$CH(CF_3)CH_2$—, —$CH(CF_2CF_3)$—, —$C(CH_3)(CF_3)$—, —$CH_2CH_2CH_2CF_2$—, —$CH_2CH_2CF_2CF_2$—, —$CH(CF_3)CH_2CH_2$—, —$CH_2CH(CF_3)CH_2$—, —$CH(CF_3)CH(CF_3)$—, —$C(CF_3)_2CH_2$—, —$CH_2$—, —$CH_2CH_2$—, —$CH_2CH_2CH_2$—, —$CH(CH_3)CH_2$—, —$CH(CH_2CH_3)$—, —$C(CH_3)_2$—, —$CH_2CH_2CH_2CH_2$—, —$CH(CH_3)CH_2CH_2$—, —$CH_2CH(CH_3)CH_2$—, —$CH(CH_3)CH(CH_3)$—, —$C(CH_3)_2CH_2$—, —$CH(CH_2CH_3)CH_2$—, —$CH(CH_2CH_2CH_3)$—, and —$C(CH_3)(CH_2CH_3)$—.

As $Y^1$, a fluorinated alkylene group is preferable, and a fluorinated alkylene group in which the carbon atom bonded to the adjacent sulfur atom is fluorinated is particularly desirable. Examples of such fluorinated alkylene groups include —$CF_2$—, —$CF_2CF_2$—, —$CF_2CF_2CF_2$—, —$CF(CF_3)CF_2$—, —$CF_2CF_2CF_2CF_2$—, —$CF(CF_3)CF_2CF_2$—, —$CF_2CF(CF_3)CF_2$—, —$CF(CF_3)CF(CF_3)$—, —$C(CF_3)_2CF_2$—, —$CF(CF_2CF_3)CF_2$—; —$CH_2CF_2$—, —$CH_2CH_2CF_2$—, —$CH_2CF_2CF_2$—; —$CH_2CH_2CH_2CF_2$—, —$CH_2CH_2CF_2CF_2$—, and —$CH_2CF_2CF_2CF_2$—.

Among these, —$CF_2$—, —$CF_2CF_2$—, —$CF_2CF_2CF_2$—, and —$CH_2CF_2CF_2$— are preferable, —$CF_2$—, —$CF_2CF_2$— and —$CF_2CF_2CF_2$— are more preferable, and —$CF_2$— is particularly desirable.

The alkylene group or fluorinated alkylene group may have a substituent. The alkylene group or fluorinated alkylene group "has a substituent" means that part or all of the hydrogen atoms or fluorine atoms in the alkylene group or fluorinated alkylene group have been substituted with atoms or groups other than hydrogen atoms and fluorine atoms.

Examples of substituents which the alkylene group or fluorinated alkylene group may have include an alkyl group of 1 to 4 carbon atoms, an alkoxy group of 1 to 4 carbon atoms, and a hydroxyl group.

Preferred examples of the anions represented by formula (x-11) include anions represented by general formula (x-11-1) shown below.

[Chemical Formula 40]

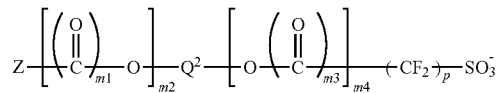

(x-11-1)

wherein Z is the same as defined above for Z in the aforementioned formula Z-$Q^1$-; $Q^2$ represents a single bond or an alkylene group; p represents an integer of 1 to 3; and m1 to m4 each independently represents 0 or 1, with the proviso that m2+m3 is 1 or 2.

In the aforementioned formula (x-11-1), p represents an integer of 1 to 3, and is preferably 1 or 2.

As the alkylene group for $Q^2$, the same alkylene groups for $R^{91}$ to $R^{93}$ as those described above in relation to $Q^1$ can be used.

Each of m1 to m4 represents 0 or 1, with the proviso that m2+m3 is 1 or 2.

More specifically, examples of the anions represented by general formula (x-11-1) include anions represented by general formula (x-11-10), anions represented by general formula (x-11-20), anions represented by general formula (x-11-30), and anions represented by general formula (x-11-40) which are shown below.

The anions represented by general formula (x-11-10) are shown below.

[Chemical Formula 41]

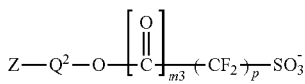
(x-11-10)

In formula (x-11-10), Z, $Q^2$, m3 and p are defined above for Z, $Q^2$, m3 and p, respectively in the aforementioned general formula (x-11-1).

In formula (x-11-10), Z is preferably an aliphatic cyclic group which may have a substituent, a linear aliphatic hydrocarbon group which may have a substituent, or an aromatic hydrocarbon group which may have a substituent. Of these, an aliphatic cyclic group which includes a hetero atom-containing substituent group in the ring structure thereof is particularly desirable.

As $Q^2$, a single bond or a methylene group is particularly desirable. Especially, when Z is an aliphatic cyclic group which may have a substituent, $Q^2$ is preferably a single bond. On the other hand, when Z is an aromatic hydrocarbon group which may have a substituent, $Q^2$ is preferably a methylene group.

Specific examples of preferred anions represented by general formula (x-11-10) are shown below.

[Chemical Formula 42]

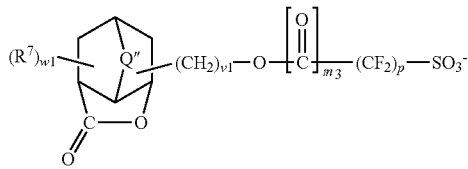
(x-11-11)

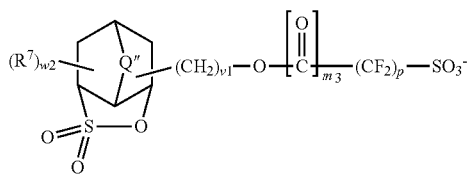
(x-11-12)

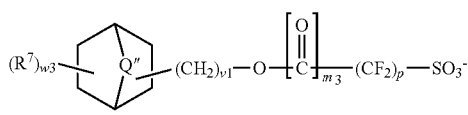
(x-11-13)

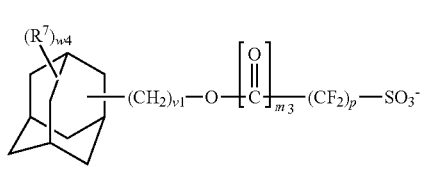
(x-11-14)

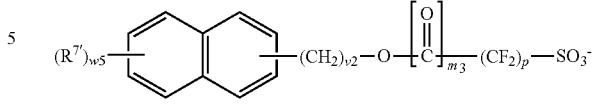
(x-11-15)

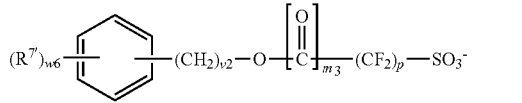
(x-11-16)

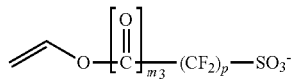
(x-11-17)

wherein Q" is as defined above for Q" in the aforementioned formulas (L1) to (L5) and (S1) to (S4); m3 and p are as defined above for m3 and p in the aforementioned general formula (x-11-1); each of $R^7$ and $R^{7'}$ independently represents a substituent; each of w1 to w6 independently represents an integer of 0 to 3; and each of v1 to v2 independently represents an integer of 0 to 5.

In the above formulas, as the substituent for $R^7$, the same groups as those which the aforementioned aliphatic hydrocarbon group for Z may have as a substituent can be used.

In the above formulas, as the substituent for $R^{7'}$, the same groups as those which the aforementioned aromatic hydrocarbon group for Z may have as a substituent can be used.

When the subscripts (w1 to w6) of $R^7$ and $R^{7'}$ represent an integer of 2 or more, the plurality of $R^7$ and $R^{7'}$ in the compound (anion) may be the same or may be different from each other.

Each of w1 to w6 independently and preferably represents an integer of 0 to 2, and is most preferably 0.

Each of v1 to v2 independently and preferably represents an integer of 0 to 3, and is most preferably 0.

The anions represented by general formula (x-11-20) are shown below.

[Chemical Formula 43]

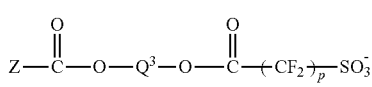
(x-11-20)

In formula (x-11-20), Z is the same as defined above for Z in the aforementioned formula Z-$Q^1$-; p is as defined above for p in the aforementioned general formula (x-11-1); and $Q^3$ represents an alkylene group.

In formula (x-11-20), Z is preferably an aliphatic cyclic group which may have a substituent, a linear aliphatic hydrocarbon group which may have a substituent, or an aromatic hydrocarbon group which may have a substituent.

As the alkylene group for $Q^3$, the same alkylene groups for R91 to R93 as those described above in relation to $Q^1$ can be used.

Specific examples of preferred anions represented by general formula (x-11-20) are shown below.

[Chemical Formula 44]

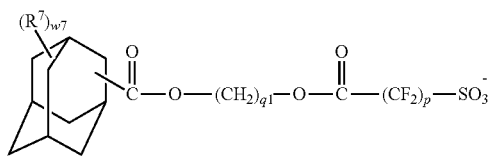
(x-11-21)

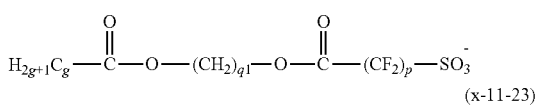
(x-11-22)

(x-11-23)

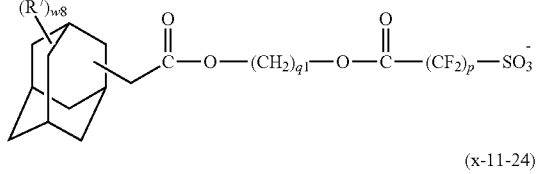
(x-11-24)

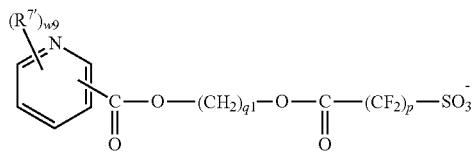

wherein p is as defined above for p in the aforementioned general formula (x-11-1); $R^7$ and $R^{7'}$ are as defined above for $R^7$ and $R^{7'}$ in the aforementioned general formulas (x-11-11) to (x-11-17); each of w7 to w9 independently represents an integer of 0 to 3; q1 represents an integer of 1 to 12; and g represents an integer of 1 to 20.

When the subscripts (w7 to w9) of $R^7$ and $R^{7'}$ represent an integer of 2 or more, the plurality of $R^7$ and $R^{7'}$ in the compound (anion) may be the same or different from each other.

Each of w7 to w9 independently and preferably represents an integer of 0 to 2, more preferably 0 or 1, and still more preferably 0.

q1 is preferably 1 to 8, more preferably 1 to 5, and still more preferably 1 to 3.

g is preferably 1 to 15, and more preferably 1 to 10.

p is preferably 1 or 2, and is most preferably 1.

The anions represented by general formula (x-11-30) are shown below.

[Chemical Formula 45]

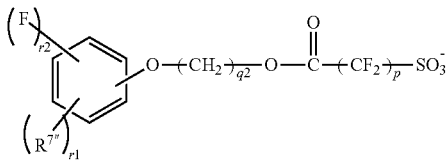
(x-11-30)

In formula (x-11-30), p is as defined above for p in the aforementioned general formula (x-11-1); q2 represents an integer of 0 to 5; $R^{7''}$ represents an alkyl group, an alkoxy group, a halogen atom (excluding a fluorine atom), a halogenated alkyl group, a hydroxyl group, an oxygen atom (=O), —COOR", —OC(=O)R", a hydroxyalkyl group or a cyano group; and r1 represents an integer of 0 to 2; and r2 represents an integer of 1 to 5, with the proviso that $1 \leq r1+r2 \leq 5$.

In formula (x-11-30), q2 is preferably 1 to 4, more preferably 1 or 2, and most preferably 2.

As an alkyl group, an alkoxy group, a halogen atom (excluding a fluorine atom), a halogenated alkyl group, —COOR", —OC(=O)R", and a hydroxyalkyl group for $R^{7''}$, the same groups as those exemplified above which the aforementioned aromatic hydrocarbon group for Z may have as a substituent can be used.

r1 is most preferably 0.

r2 is preferably 2 to 5, and is most preferably 5.

The anions represented by general formula (x-11-40) are shown below.

[Chemical Formula 46]

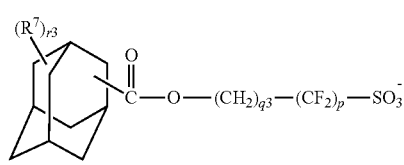
(x-11-40)

In formula (x-11-40), p is as defined above for p in the aforementioned general formula (x-11-1); $R^7$ is as defined above for $R^7$ in the aforementioned general formulas (x-11-11) to (x-11-17); q3 represents an integer of 1 to 12; and r3 represents an integer of 0 to 3.

In formula (x-11-40), $R^7$ is preferably an alkyl group, an alkoxy group, a halogen atom, a halogenated alkyl group, a hydroxyl group, an oxygen atom (=O) or a cyano group.

As the alkyl group, an alkyl group of 1 to 5 carbon atoms is preferable, and a methyl group, an ethyl group, a propyl group, an n-butyl group or a tert-butyl group is particularly desirable.

The aforementioned alkoxy group is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

Examples of the halogen atom include a fluorine atom, a chlorine atom, a bromine atom and an iodine atom, and a fluorine atom is preferable.

Examples of the aforementioned halogenated alkyl group include a group in which a part or all of the hydrogen atoms within an alkyl group of 1 to 5 carbon atoms (e.g., a methyl group, an ethyl group, a propyl group, an n-butyl group or a tert-butyl group) have been substituted with the aforementioned halogen atoms.

When the subscript (r3) of $R^7$ represents an integer of 2 or more, the plurality of $R^7$ in the compound (anion) may be the same or different from each other.

p is preferably 1 or 2, and is most preferably 1.

q3 is preferably 1 to 5, more preferably 1 to 3, and most preferably 1.

r3 is preferably an integer of 0 to 2, more preferably 0 or 1, and still more preferably 0.

Further, as $R^{4''}$, a group having an oxygen atom (=O) as a substituent is also preferable. In such a case, as $R^{4''}$, a group represented by formula $R^{10''}$—$(CH_2)_{n'}$— (wherein $R^{10''}$ represents a cyclic alkyl group of 3 to 20 carbon atoms having an oxygen atom (=O) as a substituent; and n' is 0 or 1) is preferable. The expression "having an oxygen atom (=O) as a substituent" means that two hydrogen atoms bonded to one carbon atom that constitutes a cyclic alkyl group of 3 to 20 carbon atoms have been substituted with an oxygen atom (=O).

There are no particular limitations on the cyclic alkyl group for $R^{10''}$, with the proviso that it has 3 to 20 carbon atoms, although it preferably has 4 to 20 carbon atoms and may be either a polycyclic group or a monocyclic group. Examples thereof include groups in which one hydrogen atom has been removed from a monocycloalkane or a polycycloalkane such as a bicycloalkane, a tricycloalkane or a tetracycloalkane. As the monocyclic group, groups in which one hydrogen atom has been removed from a monocycloalkane of 3 to 8 carbon atoms are preferable, and specific examples thereof include a cyclopentyl group, a cyclohexyl group, a cycloheptyl group, and a cyclooctyl group. The polycyclic group preferably has 7 to 12 carbon atoms, and specific examples thereof include an adamantyl group, a norbornyl group, an isobornyl group, a tricyclodecanyl group, and a tetracyclododecanyl group.

As $R^{10''}$, a polycyclic alkyl group of 6 to 20 carbon atoms having an oxygen atom (=O) as a substituent is preferable, and groups in which two hydrogen atoms bonded to one carbon atom that constitutes an adamantyl group, a norbornyl group or a tetracyclododecanyl group have been substituted with an oxygen atom (=O) are more preferable from an industrial point of view, and a norbornyl group having an oxygen atom (=O) as a substituent is particularly desirable.

The alkyl group for $R^{10''}$ may also have another substituent other than the oxygen atom. Examples of the substituent include a lower alkyl group of 1 to 5 carbon atoms.

In formula $R^{10''}$—$(CH_2)_{n'}$—, n' is 0 or 1, and is preferably 1.

When $R^{4''}$ is a group represented by formula $R^{10''}$—$(CH_2)_{n'}$—, $X^-$ is preferably a camphor sulfonate ion (namely, an ion obtained by replacing one hydrogen atom in camphor with —$SO_3^-$), and is particularly preferably an ion represented by the chemical formula (x-12-1) shown below (namely, an ion in which a sulfonate ion (—$SO_3^-$) is bonded to the carbon atom of the methyl group bonded to position 1 of the norbornane ring).

[Chemical Formula 47]

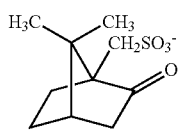

(x-12-1)

Further, examples of the anions which can be used as $X^-$, in addition to those described above, include anions represented by general formulas (b-3) and (b-4) shown below.

[Chemical Formula 48]

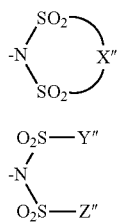

(b-3)

(b-4)

wherein X" represents an alkylene group of 2 to 6 carbon atoms in which at least one hydrogen atom has been substituted with a fluorine atom; Y" and Z" each independently represents an alkyl group or halogenated alkyl group which may have a substituent; and —$SO_2$— bonded to Z" may be substituted with —C(=O)—.

X" represents a linear or branched alkylene group in which at least one hydrogen atom has been substituted with a fluorine atom, and the alkylene group has 2 to 6 carbon atoms, preferably 3 to 5 carbon atoms, and most preferably 3 carbon atoms.

The smaller the number of carbon atoms within the alkylene group of X" within the above ranges for the number of carbon atoms, the better the solubility in a resist solvent.

In the alkylene group of X", it is preferable that the number of hydrogen atoms substituted with fluorine atoms is as large as possible, as the acid strength increases, and the transparency to high energy radiation of 200 nm or less or to electron beams is improved. The percentage of the fluorine atoms within the alkylene group or alkyl group, i.e., the fluorination ratio, is preferably from 70 to 100%, more preferably from 90 to 100%, and it is particularly desirable that the alkylene group or alkyl group be a perfluoroalkylene group or perfluoroalkyl group in which all hydrogen atoms are substituted with fluorine atoms.

The alkyl group for Y" and Z" may be a linear, branched or cyclic alkyl group, and examples thereof include the same alkyl groups as those described above for $R^{4''}$.

The halogenated alkyl group for Y" and Z" is a group in which some or all of the hydrogen atoms of the alkyl group have been substituted with halogen atoms, and examples thereof include the same halogenated alkyl groups as those described above for $R^{4''}$.

In the halogenated alkyl group, the ratio of the number of halogen atoms relative to the combined total of halogen atoms and hydrogen atoms within the halogenated alkyl group (namely, the halogenation ratio (%)) is preferably 10 to 100%, is more preferably 50 to 100%, and is most preferably 100%. Higher halogenation ratios are preferred, as they result in increased acid strength.

As the halogenated alkyl group, a fluorinated alkyl group is particularly desirable.

The alkyl group or halogenated alkyl group for Y" and Z" may have a substituent.

In the alkyl group for Y" and Z", the expression "may have a substituent" means that some or all of the hydrogen atoms within the alkyl group may be substituted with a substituent. In the halogenated alkyl group for Y" and Z", the expression "may have a substituent" means that some or all of the halogen atoms and hydrogen atoms within the halogenated alkyl group may be substituted with a substituent. The number of substituents within Y" and Z" may be either 1, or 2 or greater.

The substituent which the alkyl group or halogenated alkyl group for Y" and Z" may have can be any atom or group other than a carbon atom, a hydrogen atom and a halogen atom, and examples thereof include hetero atoms, alkyl groups, and groups represented by formula $Z^5$-$Q^5$-[wherein, $Q^5$ represents a divalent linking group containing an oxygen atom, and $Z^5$ represents a hydrocarbon group of 3 to 30 carbon atoms which may have a substituent.].

Among these substituents, examples of the hetero atoms and alkyl groups include the same hetero atoms and alkyl groups as those exemplified above as the substituents for $R^{4''}$.

In the group represented by formula $Z^5$-$Q^5$-, $Q^5$ represents a divalent linking group containing an oxygen atom.

As $Q^5$, the same divalent linking groups containing an oxygen atom as those described above for $Q^1$ in the group represented by formula Z-$Q^1$- can be used.

As $Q^5$, a divalent linking group containing an ester bond and/or an ether bond is preferable, and groups represented by formula —O—, —$R^{91}$—O—, —$R^{92}$—O—C(=O)—, —C(=O)—O—, —C(=O)—O—$R^{93}$— and —C(=O)—O—$R^{93}$—O—C(=O)— (wherein $R^{91}$ to $R^{93}$ are the same as defined above as the alkylene groups for $R^{91}$ to $R^{93}$ described above in relation to $Q^1$) are particularly desirable.

In the group represented by formula $Z^5$-$Q^5$-, $Z^5$ represents a hydrocarbon group of 3 to 30 carbon atoms which may have a substituent.

As $Z^5$, the same as those described above for Z in the group represented by formula Z-$Q^1$- can be used.

$Z^5$ is preferably an aliphatic hydrocarbon group, more preferably a linear or cyclic aliphatic hydrocarbon group, and still more preferably a cyclic aliphatic hydrocarbon group.

In the above-mentioned general formula (b-4), —$SO_2$— bonded to Z" may be substituted with —C(=O)—. That is, the anion moiety represented by the above general formula (b-4) may be an anion moiety represented by general formula (b-4') shown below.

[Chemical Formula 49]

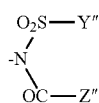
(b-4')

wherein Y" and Z" are as defined above for Y" and Z" in the above general formula (b-4).

In the present invention, at least one of Y" and Z" in general formula (b-4) and in formula (b-4') is preferably a fluorinated alkyl group which may have a substituent.

Especially in general formula (b-4), it is particularly desirable that either one of Y" and Z" be a perfluoroalkyl group, and the other be an alkyl group or fluorinated alkyl group which may have a substituent. In formula (b-4'), it is preferable that either one of Y" and Z" be a perfluoroalkyl group, and the other be an alkyl group which may have a substituent, and it is particularly desirable that Y" be a perfluoroalkyl group and Z" be an alkyl group which may have a substituent.

Examples of the anions represented by formula (b-4) or (b-4') in such cases described above include anions represented by formulas (b-4-1) to (b-4-8) as shown below.

[Chemical Formula 50]

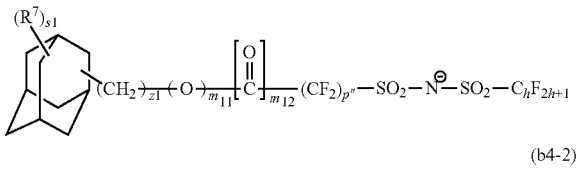
(b4-1)

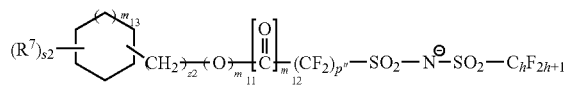
(b4-2)

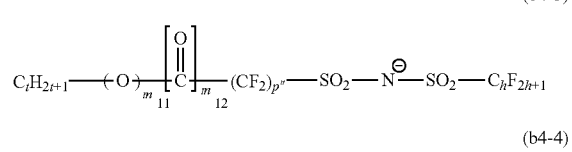
(b4-3)

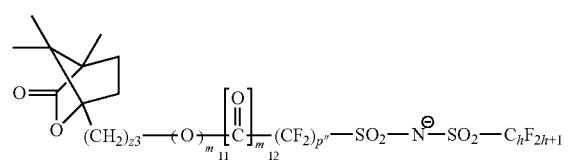
(b4-4)

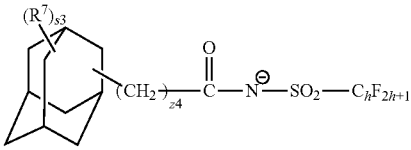
(b4-5)

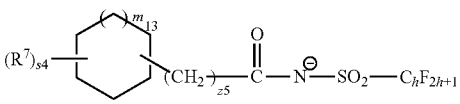
(b4-6)

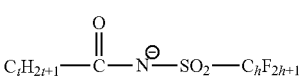
(b4-7)

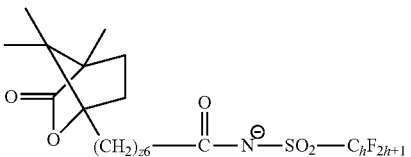
(b4-8)

wherein $R^7$ represents a substituent; each of s1 to s4 independently represents an integer of 0 to 3; each of z1 to z6 independently represents an integer of 0 to 3; p" represents an integer of 0 to 4; $m_{11}$ to $m_{13}$ are 0 or 1; h represents an integer of 1 to 4; and t represents an integer of 1 to 20.

In the above formulas, as the substituent for $R^7$, the same groups as those which the aforementioned aliphatic hydrocarbon group for Z in the group represented by formula Z-$Q^1$- may have as a substituent can be used.

When the subscripts (s1 to s4) of $R^7$ represent an integer of 2 or more, the plurality of $R^7$ in the compound (anion) may be the same or different from each other.

s1 to s4 are preferably 0 or 1, and are most preferably 0.
z1 to z6 are preferably 0 or 1.
p" is preferably 0 to 2.
$m_{12}$ is preferably 0.
h is preferably 1 or 2, and is most preferably 1.
t is more preferably 1 to 15, and still more preferably 3 to 12.

In the present invention, the anions represented by formulas (b-4-1) to (b-4-4) are particularly desirable.

Further, examples of the anions which can be used as X⁻, in addition to those described above, include a methide anion. Examples of the methide anion include anions represented by general formula (b-c1) shown below.

[Chemical Formula 51]

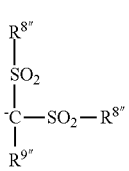
(b-c1)

wherein $R^{8"}$ represents an alkyl group of 1 to 10 carbon atoms in which at least one hydrogen atom is substituted with a fluorine atom; and $R^{9"}$ represents a hydrocarbon group which may have a substituent, or —$SO_2$—$R^{8"}$.

In general formula (b-c1), $R^{8"}$ represents an alkyl group of 1 to 10 carbon atoms in which at least one hydrogen atom is substituted with a fluorine atom. The alkyl group may be a linear, branched or cyclic alkyl group. As $R^{8'''}$ in the present invention, a linear or branched alkyl group is preferable, and a linear alkyl group is more preferable.

When $R^{9'''}$ represents a hydrocarbon group which may have a substituent in general formula (b-c1) (the expression "hydrocarbon group which may have a substituent" means that a part or all of the hydrogen atoms constituting the hydrocarbon group may be substituted with a substituent), the hydrocarbon group for $R^{9'''}$ may be either an aliphatic hydrocarbon group or an aromatic hydrocarbon group. Specific examples thereof include the same hydrocarbon groups as those described above for Z in the above formula $Z-Q^1-$.

As $R^{9'''}$, an aryl group having a halogen atom as a substituent (namely, a halogenated aryl group), or $-SO_2-R^{8'''}$ is preferable. The aryl group within the halogenated aryl group is an aryl group of 6 to 10 carbon atoms such as a phenyl group and a naphthyl group, and examples of the halogenated aryl group include groups in which a part or all of the hydrogen atoms of the above-mentioned aryl groups have been substituted with halogen atoms. As the halogen atom within the halogenated alkyl group, a fluorine atom is preferable.

$R^{8'''}$ in formula $-SO_2-R^{8'''}$ is as defined above for $R^{8'''}$ in the aforementioned general formula (b-c1).

Among those described above, as $X^-$, anions represented by the aforementioned general formula (x-1) are preferred. Of these, an anion in which $R^{4''}$ in general formula (x-1) represents a fluorinated alkyl group which may have a substituent (namely, a fluorinated alkylsulfonate ion which may have a substituent) is particularly desirable.

Further, as the anion represented by general formula (x-1), anions represented by the aforementioned general formula (x-11) are preferred, and an anion in which $Y^1$ in general formula (x-11) represents a fluorinated alkylene group of 1 to 4 carbon atoms which may have a substituent is particularly desirable.

Furthermore, as $X^-$, anions represented by the aforementioned general formulas (b-3) and (b-4) and anions represented by the aforementioned formula (x-12-1) are also preferred.

As the component (B1), one type may be used alone, or two or more types may be used in combination.

The proportion of the component (B1) within the component (B) is preferably from 1 to 100% by weight, more preferably from 5 to 70% by weight, and still more preferably from 10 to 50% by weight.

In the resist composition of the present invention, the component (B) may further include an acid generator component other than the component (B1) (hereafter, referred to as "component (B2)").

As the component (B2), there is no particular limitation, and any of the known acid generators used in conventional chemically amplified resist compositions can be used. Examples of these acid generators are numerous, and include onium salt-based acid generators such as iodonium salts and sulfonium salts; oxime sulfonate-based acid generators; diazomethane-based acid generators such as bisalkyl or bisaryl sulfonyl diazomethanes and poly(bis-sulfonyl)diazomethanes; nitrobenzylsulfonate-based acid generators; iminosulfonate-based acid generators; and disulfone-based acid generators.

As an onium salt-based acid generator, a compound represented by general formula (b-1) or (b-2) shown below can be used.

[Chemical Formula 52]

wherein $R^{1'''}$ to $R^{3'''}$ and $R^{5'''}$ to $R^{6'''}$ each independently represent an aryl group or alkyl group which may have a substituent, wherein two of $R^{1'''}$ to $R^{3'''}$ in formula (b-1) may be bonded to each other to form a ring with the sulfur atom, and at least one of $R^{1'''}$ to $R^{3'''}$ represents the aforementioned aryl group; at least one of $R^{5'''}$ to $R^{6'''}$ represents the aforementioned aryl group; and $R^{4''}$ is as defined above for $R^{4''}$ in the aforementioned general formula (x-1).

In general formula (b-1), $R^{1'''}$ to $R^{3'''}$ each independently represent an aryl group or alkyl group which may have a substituent. In general formula (b-1), two of $R^{1'''}$ to $R^{3'''}$ in formula (b-1) may be bonded to each other to form a ring with the sulfur atom.

Further, among $R^{1'''}$ to $R^{3'''}$, at least one group represents an aryl group. Among $R^{1'''}$ to $R^{3'''}$, two or more groups are preferably aryl groups, and it is particularly desirable that all of $R^{1'''}$ to $R^{3'''}$ are aryl groups.

The aryl group for $R^{1'''}$ to $R^{3'''}$ is not particularly limited, and examples thereof include an aryl group having 6 to 20 carbon atoms. The aryl group is preferably an aryl group having 6 to 10 carbon atoms because it can be synthesized at a low cost. Specific examples thereof include a phenyl group and a naphthyl group.

The aryl group may have a substituent. The expression "having a substituent" means that some or all of the hydrogen atoms of the aryl group are substituted with substituents, and examples of the substituent include an alkyl group, an alkoxy group, a halogen atom, a hydroxyl group, an alkoxyalkyloxy group, and a group $-O-R^{50}-CO-O-R^{51}$ (wherein $R^{50}$ represents an alkylene group, and $R^{51}$ represents an acid dissociable group).

The alkyl group, with which hydrogen atoms of the aryl group may be substituted, is preferably an alkyl group having 1 to 5 carbon atoms, and most preferably a methyl group, an ethyl group, a propyl group, an n-butyl group, or a tert-butyl group.

The alkoxy group, with which hydrogen atoms of the aryl group may be substituted, is preferably an alkoxy group having 1 to 5 carbon atoms, more preferably a methoxy group, an ethoxy group, an n-propoxy group, an iso-propoxy group, an n-butoxy group or a tert-butoxy group, and most preferably a methoxy group or an ethoxy group.

The halogen atom, with which hydrogen atoms of the aryl group may be substituted, is preferably a fluorine atom.

Examples of the alkoxyalkyloxy group, with which hydrogen atoms of the aryl group may be substituted, include a group $-O-C(R^{47})(R^{48})-O-R^{49}$ (wherein each of $R^{47}$ and $R^{48}$ independently represents a hydrogen atom or a linear or branched alkyl group; $R^{49}$ represents an alkyl group; and $R^{47}$ and $R^{48}$ may be bonded to each other to form one ring structure, with the proviso that at least one of $R^{47}$ and $R^{48}$ is a hydrogen atom).

The alkyl group for $R^{47}$ and $R^{48}$ preferably has 1 to 5 carbon atoms, and is preferably an ethyl group or a methyl group, and most preferably a methyl group.

It is preferable that either one of $R^{47}$ and $R^{48}$ be a hydrogen atom and the other be a hydrogen atom or a methyl group, and it is particularly desirable that both of $R^{47}$ and $R^{48}$ be a hydrogen atom.

The alkyl group for $R^{49}$ preferably has 1 to 15 carbon atoms, and may be linear, branched or cyclic.

The linear or branched alkyl group for $R^{49}$ preferably has 1 to 5 carbon atoms. Examples thereof include a methyl group, an ethyl group, a propyl group, an n-butyl group and a tert-butyl group.

The cyclic alkyl group for $R^{49}$ preferably has 4 to 15 carbon atoms, more preferably 4 to 12 carbon atoms, and most preferably 5 to 10 carbon atoms. Specific examples thereof include groups in which one or more hydrogen atoms have been removed from a monocycloalkane or a polycycloalkane such as a bicycloalkane, tricycloalkane or tetracycloalkane, and which may or may not be substituted with alkyl groups of 1 to 5 carbon atoms, fluorine atoms or fluorinated alkyl groups. Examples of the monocycloalkane include cyclopentane and cyclohexane. Examples of the polycycloalkane include adamantane, norbornane, isobornane, tricyclodecane and tetracyclododecane. Of these, a group in which one or more hydrogen atoms have been removed from adamantane is particularly desirable.

$R^{47}$ and $R^{48}$ may be bonded to each other to form one ring structure. In such a case, a cyclic group is formed by $R^{47}$, $R^{48}$, the oxygen atom having $R^{49}$ bonded thereto, and the carbon atom having the oxygen atom and $R^{48}$ bonded thereto. Such a cyclic group is preferably a 4 to 7-membered ring, and more preferably a 4 to 6-membered ring.

In the group —O—$R^{50}$—CO—O—$R^{51}$, with which hydrogen atoms of the aryl group may be substituted, the alkylene group for $R^{50}$ is preferably a linear or branched alkylene group, and is preferably an alkylene group of 1 to 5 carbon atoms. Examples of the alkylene group include a methylene group, an ethylene group, a trimethylene group, a tetramethylene group and a 1,1-dimethylethylene group.

The acid dissociable group for $R^{51}$ is not particularly limited as long as it is an organic group which can be dissociated by the action of acid (the acid generated from the component (B) upon exposure), and examples thereof include the same as those exemplified above as acid dissociable, dissolution inhibiting groups within the structural unit (a1). Here, unlike the aforementioned acid dissociable, dissolution inhibiting group, the acid dissociable group does not necessarily exhibit a dissolution inhibiting effect in an alkali developing solution.

Examples of the acid dissociable group include a tertiary alkyl ester-type acid dissociable group such as a cyclic or chain-like tertiary alkyl group, or an acetal-type acid dissociable group such as an alkoxyalkyl group. Among these, a tertiary alkyl ester-type acid dissociable group is preferable.

Specific examples of the tertiary alkyl ester-type acid dissociable group include a 2-methyl-2-adamantyl group, a 2-ethyl-2-adamantyl group, a 1-methyl-1-cyclopentyl group, a 1-ethyl-1-cyclopentyl group, a 1-methyl-1-cyclohexyl group, a 1-ethyl-1-cyclohexyl group, a 1-(1-adamantyl)-1-methylethyl group, a 1-(1-adamantyl)-1-methylpropyl group, a 1-(1-adamantyl)-1-methylbutyl group, a 1-(1-adamantyl)-1-methylpentyl group, a 1-(1-cyclopentyl)-1-methylethyl group, a 1-(1-cyclopentyl)-1-methylpropyl group, a 1-(1-cyclopentyl)-1-methylbutyl group, a 1-(1-cyclopentyl)-1-methylpentyl group, a 1-(1-cyclohexyl)-1-methylethyl group, a 1-(1-cyclohexyl)-1-methylpropyl group, a 1-(1-cyclohexyl)-1-methylbutyl group, a 1-(1-cyclohexyl)-1-methylpentyl group, a tert-butyl group, a tert-pentyl group and a tert-hexyl group.

The alkyl group for $R^{1'''}$ to $R^{3'''}$ is not particularly limited and includes, for example, a linear, branched or cyclic alkyl group having 1 to 10 carbon atoms. In terms of achieving excellent resolution, the alkyl group preferably has 1 to 5 carbon atoms. Specific examples thereof include a methyl group, an ethyl group, an n-propyl group, an isopropyl group, an n-butyl group, an isobutyl group, an n-pentyl group, a cyclopentyl group, a hexyl group, a cyclohexyl group, a nonyl group, and a decanyl group, and a methyl group is most preferable because it is excellent in resolution and can be synthesized at a low cost.

The alkyl group may have a substituent. The expression "have a substituent" means that some or all of the hydrogen atoms of the alkyl group are substituted with substituents. As the substituent, the same groups as those which the aforementioned aryl group may have as a substituent can be used.

When two of $R^{1'''}$ to $R^{3'''}$ in formula (b-1) are bonded to each other to form a ring with the sulfur atom, it is preferable that the two of $R^{1'''}$ to $R^{3'''}$ form a 3 to 10-membered ring including the sulfur atom, and it is particularly desirable that the two of $R^{1'''}$ to $R^{3'''}$ form a 5 to 7-membered ring including the sulfur atom.

When two of $R^{1'''}$ to $R^{3'''}$ in formula (b-1) are bonded to each other to form a ring with the sulfur atom, the remaining one of $R^{1'''}$ to $R^{3'''}$ is preferably an aryl group. As examples of the aryl group, the same as the above-mentioned aryl groups for $R^{1'''}$ to $R^{3'''}$ can be exemplified.

Preferred examples of the cation moiety of the compound represented by formula (b-1) include the cation moieties represented by formulas (I-1-1) to (I-1-10) shown below. Of these, the cation moieties having a triphenylmethane structure such as those represented by formulas (I-1-1) to (I-1-8) are particularly desirable.

In the formulas (I-1-9) to (I-1-10) shown below, each of $R^9$ and $R^{10}$ independently represents a phenyl group or naphthyl group which may have a substituent, an alkyl group of 1 to 5 carbon atoms, an alkoxy group or a hydroxyl group.

u represents an integer of 1 to 3, and is most preferably 1 or 2.

[Chemical Formula 53]

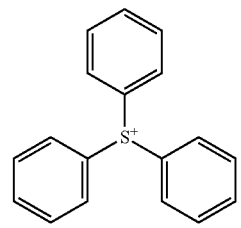

(I-1-1)

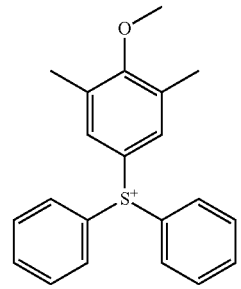

(I-1-2)

(I-1-3)

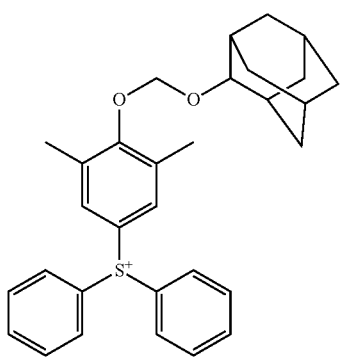

(I-1-4)

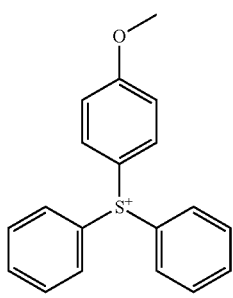

(I-1-5)

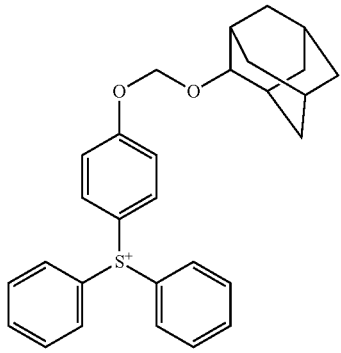

(I-1-6)

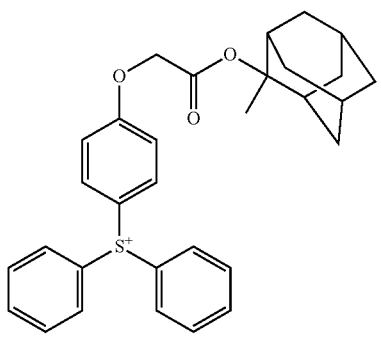

(I-1-7)

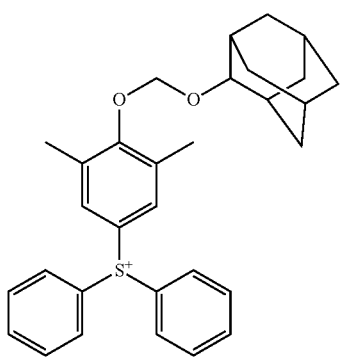

(I-1-8)

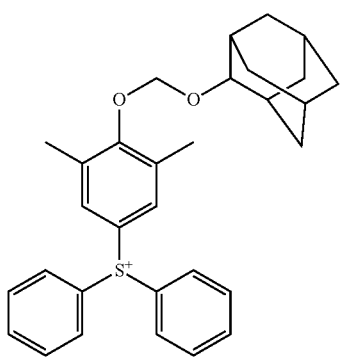

(I-1-9)

$$R^9 - \overset{+}{S} \begin{pmatrix} (CH_2)_u \end{pmatrix}$$

(I-1-10)

$$R^{10} \overset{O}{\underset{}{\bigg\|}} \overset{+}{S} \begin{pmatrix} (CH_2)_u \end{pmatrix}$$

In formula (b-2), $R^{5''}$ and $R^{6''}$ each independently represent an aryl group or an alkyl group. At least one of $R^{5''}$ and $R^{6''}$ represents an aryl group. It is preferable that both of $R^{5''}$ and $R^{6''}$ represent an aryl group.

As the aryl group for $R^{5''}$ and $R^{6''}$, the same as the aryl groups for $R^{1''}$ to $R^{3''}$ can be exemplified.

As the alkyl group for $R^{5''}$ and $R^{6''}$, the same as the alkyl groups for $R^{1''}$ to $R^{3''}$ can be exemplified.

It is particularly desirable that both of $R^{5''}$ and $R^{6''}$ represents a phenyl group.

As $R^{4''}$ in formula (b-2), the same as those mentioned above for $R^{4''}$ in formula (b-1) can be exemplified.

Specific examples of suitable onium salt-based acid generators represented by formula (b-1) or (b-2) include diphenyliodonium trifluoromethanesulfonate or nonafluorobutanesulfonate; bis(4-tert-butylphenyl)iodonium trifluoromethanesulfonate or nonafluorobutanesulfonate; triphenylsulfonium trifluoromethanesulfonate, heptafluoropropanesulfonate or nonafluorobutanesulfonate; tri(4-methylphenyl)sulfonium trifluoromethanesulfonate, heptafluoropropanesulfonate or nonafluorobutanesulfonate; dimethyl(4-hydroxynaphthyl)sulfonium trifluoromethanesulfonate, heptafluoropropanesulfonate or nonafluorobutanesulfonate; monophenyldimethylsulfonium trifluoromethanesulfonate, heptafluoropropanesulfonate or nonafluorobutanesulfonate; diphenylmonomethylsulfonium trifluoromethanesulfonate, heptafluoropropanesulfonate or nonafluorobutanesulfonate; (4-methylphenyl)diphenylsulfonium trifluoromethanesulfonate, heptafluoropropanesulfonate or nonafluorobutanesulfonate; (4-methoxyphenyl)diphenylsulfonium trifluoromethanesulfonate, heptafluoropropanesulfonate or nonafluorobutanesulfonate; tri(4-tert-butyl)phenylsulfonium trifluoromethanesulfonate, heptafluoropropanesulfonate or nonafluorobutanesulfonate; diphenyl(1-(4-methoxy)naphthyl)sulfonium trifluoromethanesulfonate, heptafluoropropanesulfonate or nonafluorobutanesulfonate; di(1-naphthyl)phenylsulfonium trifluoromethanesulfonate, heptafluoropropanesulfonate or nonafluorobutanesulfonate; 1-phenyltetrahydrothiophenium trifluoromethanesulfonate, heptafluoropropanesulfonate or nonafluorobutanesulfonate; 1-(4-methylphenyl)tetrahydrothiophenium trifluoromethanesulfonate, heptafluoropropanesulfonate or nonafluorobutanesulfonate; 1-(3,5-dimethyl-4-hydroxyphenyl)tetrahydrothiophenium trifluoromethanesulfonate, heptafluoropropanesulfonate or nonafluorobutanesulfonate; 1-(4-methoxynaphthalene-1-yl)tetrahydrothiophenium trifluoromethanesulfonate, heptafluoropropanesulfonate or nonafluorobutanesulfonate; 1-(4-ethoxynaphthalene-1-yl)tetrahydrothiophenium trifluoromethanesulfonate, heptafluoropropanesulfonate or nonafluorobutanesulfonate; 1-(4-n-butoxynaphthalene-1-yl)tetrahydrothiophenium trifluoromethanesulfonate, heptafluoropropanesulfonate or nonafluorobutanesulfonate; 1-phenyltetrahydrothiopyranium trifluoromethanesulfonate, heptafluoropropanesulfonate or nonafluorobutanesulfonate; 1-(4-hydroxyphenyl)tetrahydrothiopyranium trifluoromethanesulfonate, heptafluoropropanesulfonate or nonafluorobutanesulfonate; 1-(3,5-dimethyl-4-hydroxyphenyl)tetrahydrothiopyranium trifluoromethanesulfonate, heptafluoropropanesulfonate or nonafluorobutanesulfonate; and 1-(4-methylphenyl)tetrahydrothiopyranium trifluoromethanesulfonate, heptafluoropropanesulfonate or nonafluorobutanesulfonate.

It is also possible to use onium salts in which the anion moiety of these onium salts are replaced by methanesulfonate, n-propanesulfonate, n-butanesulfonate, or n-octanesulfonate.

Further, onium salt-based acid generators in which the anion moiety in the aforementioned general formula (b-1) or (b-2) is replaced by an anion moiety represented by the aforementioned general formula (b-3) or (b-4) (the cation moiety is the same as (b-1) or (b-2)) may also be used.

Furthermore, as the onium salt-based acid generator, a sulfonium salt having a cation moiety represented by general formula (b-5) or (b-6) shown below may also be used.

[Chemical Formula 54]

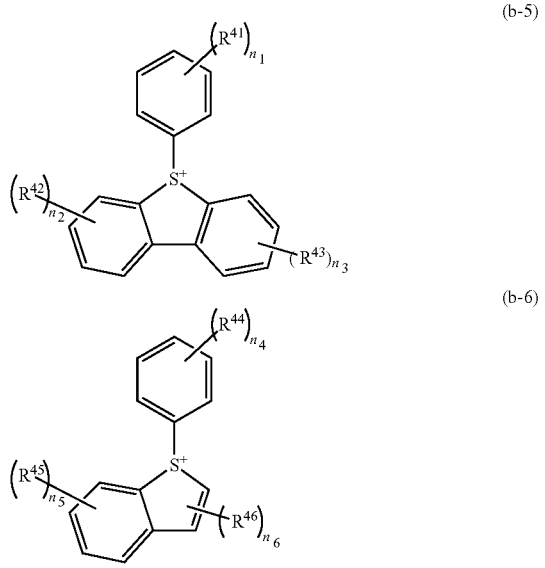

(b-5)

(b-6)

wherein $R^{41}$ to $R^{46}$ each independently represent an alkyl group, an acetyl group, an alkoxy group, a carboxyl group, a hydroxyl group or a hydroxyalkyl group; $n_1$ to $n_5$ each independently represent an integer of 0 to 3; and $n_6$ represents an integer of 0 to 2.

With respect to $R^{41}$ to $R^{46}$, the alkyl group is preferably an alkyl group of 1 to 5 carbon atoms, more preferably a linear or branched alkyl group, and most preferably a methyl group, an ethyl group, a propyl group, an isopropyl group, an n-butyl group or a tert-butyl group.

The alkoxy group is preferably an alkoxy group of 1 to 5 carbon atoms, more preferably a linear or branched alkoxy group, and most preferably a methoxy group or an ethoxy group.

The hydroxyalkyl group is preferably the aforementioned alkyl group in which one or more hydrogen atoms have been substituted with hydroxy groups, and examples thereof include a hydroxymethyl group, a hydroxyethyl group and a hydroxypropyl group.

When the subscripts $n_1$ to $n_6$ of $R^{41}$ to $R^{46}$ represent an integer of 2 or more, the plurality of $R^{41}$ to $R^{46}$ may be the same or different from each other.

$n_1$ is preferably 0 to 2, more preferably 0 or 1, and still more preferably 0.

It is preferable that $n_2$ and $n_3$ each independently represent 0 or 1, and more preferably 0.

$n_4$ is preferably 0 to 2, and more preferably 0 or 1.

$n_5$ is preferably 0 or 1, and more preferably 0.

$n_6$ is preferably 0 or 1, and more preferably 1.

The anion moiety of the sulfonium salt having a cation moiety represented by general formula (b-5) or (b-6) is not particularly limited, and the same anion moieties as those used within previously proposed onium salt-based acid generators may be used. Examples of such anion moieties include fluorinated alkylsulfonate ions such as anion moieties ($R^{4"}SO_3^-$) for onium salt-based acid generators represented by general formula (b-1) or (b-2) shown above; and anion moieties represented by general formula (b-3) or (b-4) shown above. Among these, a fluorinated alkylsulfonate ion is preferable, a fluorinated alkylsulfonate ion of 1 to 4 carbon atoms is more preferable, and a linear perfluoroalkylsulfonate ion of 1 to 4 carbon atoms is particularly desirable. Specific examples thereof include a trifluoromethylsulfonate ion, a heptafluoro-n-propylsulfonate ion and a nonafluoro-n-butylsulfonate ion.

In the present description, an oximesulfonate-based acid generator is a compound having at least one group represented by general formula (B-1) shown below, and has a feature of generating acid by irradiation. Such oximesulfonate-based acid generators are widely used for a chemically amplified resist composition, and can be appropriately selected.

[Chemical Formula 55]

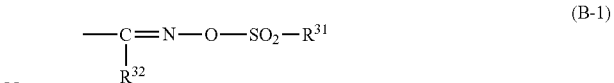

(B-1)

wherein $R^{31}$ and $R^{32}$ each independently represent an organic group.

The organic group for $R^{31}$ and $R^{32}$ refers to a group containing a carbon atom, and may include atoms other than carbon atoms (e.g., a hydrogen atom, an oxygen atom, a nitrogen atom, a sulfur atom, a halogen atom (such as a fluorine atom and a chlorine atom) and the like).

As the organic group for $R^{31}$, a linear, branched, or cyclic alkyl group or aryl group is preferable. The alkyl group or the aryl group may have a substituent. The substituent is not particularly limited, and examples thereof include a fluorine atom and a linear, branched, or cyclic alkyl group having 1 to 6 carbon atoms. The expression "have a substituent" means that some or all of the hydrogen atoms of the alkyl group or the aryl group are substituted with substituents.

The alkyl group preferably has 1 to 20 carbon atoms, more preferably has 1 to 10 carbon atoms, still more preferably has 1 to 8 carbon atoms, still more preferably has 1 to 6 carbon atoms, and most preferably has 1 to 4 carbon atoms. As the alkyl group, a partially or completely halogenated alkyl group (hereinafter, sometimes referred to as a "halogenated alkyl group") is particularly desirable. The "partially halogenated alkyl group" refers to an alkyl group in which some of the hydrogen atoms are substituted with halogen atoms, and the "completely halogenated alkyl group" refers to an alkyl group in which all of the hydrogen atoms are substituted with halogen atoms. Examples of the halogen atom include a fluorine atom, a chlorine atom, a bromine atom and an iodine atom, and a fluorine atom is particularly desirable. In other words, the halogenated alkyl group is preferably a fluorinated alkyl group.

The aryl group preferably has 4 to 20 carbon atoms, more preferably 4 to 10 carbon atoms, and most preferably 6 to 10 carbon atoms. As the aryl group, a partially or completely halogenated aryl group is particularly desirable. The "partially halogenated aryl group" refers to an aryl group in which some of the hydrogen atoms are substituted with halogen atoms, and the "completely halogenated aryl group" refers to an aryl group in which all of hydrogen atoms are substituted with halogen atoms.

As $R^{31}$, an alkyl group of 1 to 4 carbon atoms which has no substituent, or a fluorinated alkyl group of 1 to 4 carbon atoms is particularly desirable.

As the organic group for $R^{32}$, a linear, branched, or cyclic alkyl group, an aryl group, or a cyano group is preferable. Examples of the alkyl group and the aryl group for $R^{32}$ are the same as those of the alkyl group and the aryl group for $R^{31}$.

As $R^{32}$, a cyano group, an alkyl group of 1 to 8 carbon atoms having no substituent or a fluorinated alkyl group of 1 to 8 carbon atoms is particularly desirable.

Preferred examples of the oxime sulfonate-based acid generator include compounds represented by general formula (B-2) or (B-3) shown below.

[Chemical Formula 56]

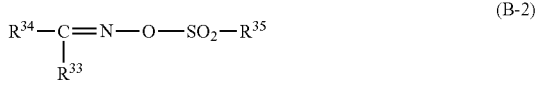

(B-2)

wherein $R^{33}$ represents a cyano group, an alkyl group having no substituent, or a halogenated alkyl group; $R^{34}$ represents an aryl group; and $R^{35}$ represents an alkyl group having no substituent, or a halogenated alkyl group.

[Chemical Formula 57]

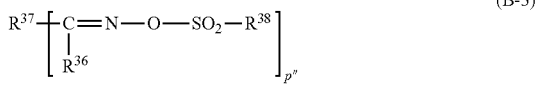

(B-3)

wherein $R^{36}$ represents a cyano group, an alkyl group having no substituent, or a halogenated alkyl group; $R^{37}$ represents a divalent or trivalent aromatic hydrocarbon group; $R^{38}$ represents an alkyl group having no substituent, or a halogenated alkyl group; and p" represents 2 or 3.

In the aforementioned general formula (B-2), the alkyl group having no substituent or the halogenated alkyl group for $R^{33}$ preferably has 1 to 10 carbon atoms, more preferably has 1 to 8 carbon atoms, and most preferably has 1 to 6 carbon atoms.

As $R^{33}$, a halogenated alkyl group is preferable, and a fluorinated alkyl group is more preferable.

The fluorinated alkyl group for $R^{33}$ preferably has 50% or more of the hydrogen atoms thereof fluorinated, more preferably has 70% or more, and most preferably has 90% or more.

Examples of the aryl group for $R^{34}$ include groups in which one hydrogen atom has been removed from an aromatic hydrocarbon ring, such as a phenyl group, a biphenyl group, a fluorenyl group, a naphthyl group, an anthryl group, and a phenanthryl group, and heteroaryl groups in which some of the carbon atoms constituting the ring(s) of these groups are substituted with hetero atoms such as an oxygen atom, a sulfur atom, and a nitrogen atom. Of these, a fluorenyl group is preferable.

The aryl group for $R^{34}$ may have a substituent such as an alkyl group of 1 to 10 carbon atoms, a halogenated alkyl group, or an alkoxy group. The alkyl group and halogenated alkyl group as the substituent preferably has 1 to 8 carbon atoms, and more preferably has 1 to 4 carbon atoms. The halogenated alkyl group is preferably a fluorinated alkyl group.

The alkyl group having no substituent or the halogenated alkyl group for $R^{35}$ preferably has 1 to 10 carbon atoms, more preferably has 1 to 8 carbon atoms, and most preferably 1 to 6 carbon atoms.

As $R^{35}$, a halogenated alkyl group is preferable, and a fluorinated alkyl group is more preferable.

In terms of enhancing the strength of the acid generated, the fluorinated alkyl group for $R^{35}$ preferably has 50% or more of the hydrogen atoms fluorinated, more preferably has 70% or more of the hydrogen atoms fluorinated, and still more preferably has 90% or more of the hydrogen atoms fluorinated. A completely fluorinated alkyl group in which 100% of the hydrogen atoms are substituted with fluorine atoms is particularly desirable.

In the aforementioned general formula (B-3), the alkyl group having no substituent and the halogenated alkyl group for $R^{36}$ are the same as the alkyl group having no substituent and the halogenated alkyl group for $R^{33}$.

Examples of the divalent or trivalent aromatic hydrocarbon group for $R^{37}$ include groups in which one or two hydrogen atoms have been removed from the aryl group for $R^{34}$.

As the alkyl group having no substituent or the halogenated alkyl group for $R^{38}$, the same one as the alkyl group having no substituent or the halogenated alkyl group for $R^{35}$ can be used.

p" is preferably 2.

Specific examples of suitable oxime sulfonate-based acid generators include α-(p-toluenesulfonyloxyimino)-benzyl cyanide, α-(p-chlorobenzenesulfonyloxyimino)-benzyl cyanide, α-(4-nitrobenzenesulfonyloxyimino)-benzyl cyanide, α-(4-nitro-2-trifluoromethylbenzenesulfonyloxyimino)-benzyl cyanide, α-(benzenesulfonyloxyimino)-4-chlorobenzyl cyanide, α-(benzenesulfonyloxyimino)-2,4-dichlorobenzyl cyanide, α-(benzenesulfonyloxyimino)-2,6-dichlorobenzyl cyanide, α-(benzenesulfonyloxyimino)-4-methoxybenzyl cyanide, α-(2-chlorobenzenesulfonyloxyimino)-4-methoxybenzyl cyanide, α-(benzenesulfonyloxyimino)-thien-2-yl acetonitrile, α-(4-dodecylbenzenesulfonyloxyimino)benzyl cyanide, α-[(p-toluenesulfonyloxyimino)-4-methoxyphenyl]acetonitrile, α-[(dodecylbenzenesulfonyloxyimino)-4-methoxyphenyl]acetonitrile, α-(tosyloxyimino)-4-thienyl cyanide, α-(methylsulfonyloxyimino)-1-cyclopentenyl acetonitrile, α-(methylsulfonyloxyimino)-1-cyclohexenyl acetonitrile, α-(methylsulfonyloxyimino)-1-cycloheptenyl acetonitrile, α-(methylsulfonyloxyimino)-1-cyclooctenylacetonitrile, α-(trifluoromethylsulfonyloxyimino)-1-cyclopentenyl acetonitrile, α-(trifluoromethylsulfonyloxyimino)-cyclohexyl acetonitrile, α-(ethylsulfonyloxyimino)-ethyl acetonitrile, α-(propylsulfonyloxyimino)-propyl acetonitrile, α-(cyclohexylsulfonyloxyimino)-cyclopentyl acetonitrile, α-(cyclohexylsulfonyloxyimino)-cyclohexyl acetonitrile, α-(cyclohexylsulfonyloxyimino)-1-cyclopentenylacetonitrile, α-(ethylsulfonyloxyimino)-1-cyclopentenyl acetonitrile, α-(isopropylsulfonyloxyimino)-1-cyclopentenyl acetonitrile, α-(n-butylsulfonyloxyimino)-1-cyclopentenyl acetonitrile, α-(ethylsulfonyloxyimino)-1-cyclohexenyl acetonitrile, α-(isopropylsulfonyloxyimino)-1-cyclohexenyl acetonitrile, α-(n-butylsulfonyloxyimino)-1-cyclohexenyl acetonitrile, α-(methylsulfonyloxyimino)-phenyl acetonitrile, α-(methylsulfonyloxyimino)-p-methoxyphenyl acetonitrile, α-(trifluoromethylsulfonyloxyimino)-phenyl acetonitrile, α-(trifluoromethylsulfonyloxyimino)-p-methoxyphenyl acetonitrile, α-(ethylsulfonyloxyimino)-p-methoxyphenyl acetonitrile, α-(propylsulfonyloxyimino)-p-methylphenyl acetonitrile, and α-(methylsulfonyloxyimino)-p-bromophenyl acetonitrile.

Further, oxime sulfonate-based acid generators disclosed in Japanese Unexamined Patent Application, First Publication No. Hei 9-208554 (Chemical Formulas 18 and 19 shown in paragraphs [0012] to [0014]) and oxime sulfonate-based acid generators disclosed in WO 2004/074242A2 (Examples 1 to 40 described at pages 65 to 85) may be preferably used.

Furthermore, as preferable examples, the following can be exemplified.

[Chemical Formula 58]

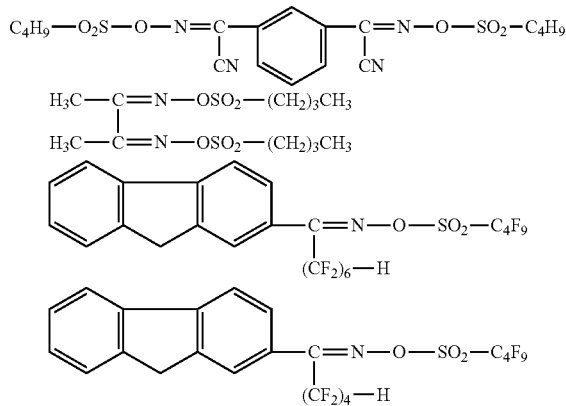

Of the aforementioned diazomethane-based acid generators, specific examples of suitable bisalkyl or bisaryl sulfonyl diazomethanes include bis(isopropylsulfonyl)diazomethane, bis(p-toluenesulfonyl)diazomethane, bis(1,1-dimethylethylsulfonyl)diazomethane, bis(cyclohexylsulfonyl)diazomethane, and bis(2,4-dimethylphenylsulfonyl)diazomethane.

Further, diazomethane-based acid generators disclosed in Japanese Unexamined Patent Application, First Publication No. Hei 11-035551, Japanese Unexamined Patent Application, First Publication No. Hei 11-035552 and Japanese Unexamined Patent Application, First Publication No. Hei 11-035573 may be preferably used.

Furthermore, poly(bis-sulfonyl)diazomethanes may be exemplified by those disclosed in Japanese Unexamined Patent Application, First Publication No. Hei 11-322707, including 1,3-bis(phenylsulfonyldiazomethylsulfonyl)propane, 1,4-bis(phenylsulfonyldiazomethylsulfonyl)butane, 1,6-bis(phenylsulfonyldiazomethylsulfonyl)hexane, 1,10-bis(phenylsulfonyldiazomethylsulfonyl)decane, 1,2-bis(cyclohexylsulfonyldiazomethylsulfonyl)ethane, 1,3-bis(cyclohexylsulfonyldiazomethylsulfonyl)propane, 1,6-bis(cyclohexylsulfonyldiazomethylsulfonyl)hexane, and 1,10-bis(cyclohexylsulfonyldiazomethylsulfonyl)decane.

As the component (B2), any one type of these acid generators may be used alone, or two or more types may be used in combination.

Of these, as the component (B2), an onium salt-based acid generator having an anion in which the aforementioned $R^{4''}$ represents a fluorinated alkyl group which may have a substituent (namely, a fluorinated alkylsulfonate ion which may have a substituent) is preferable. An onium salt-based acid generator in which $Y^1$ in the aforementioned general formula (x-11) represents a fluorinated alkylene group of 1 to 4 carbon atoms which may have a substituent is particularly desirable.

When the component (B2) is included in the component (B), the amount of the component (B2) within the component (B) is preferably 10 to 90% by weight, and more preferably 50 to 75% by weight.

The ratio (molar ratio) between the blend quantities of the component (B1) and the component (B2) within the component (B) is preferably within a range from (B1):(B2)=9:1 to 1:9, more preferably from 4:1 to 1:4, and still more preferably from 1:1 to 1:3.

The total amount of the component (B) within the resist composition of the present invention is preferably from 0.5 to 60 parts by weight, more preferably from 1 to 40 parts by weight, and still more preferably from 1 to 30 parts by weight, relative to 100 parts by weight of the component (A). When the amount of the component (B) is within the above-mentioned range, formation of a resist pattern can be satisfactorily performed. Further, by virtue of the above-mentioned range, a uniform solution can be obtained and the storage stability becomes satisfactory.

<Optional Component>

For improving the resist pattern shape and the post exposure stability of the latent image formed by the pattern-wise exposure of the resist layer, the resist composition of the present invention may further contain a nitrogen-containing organic compound (D) (hereafter referred to as the component (D)) as an optional component.

A multitude of these components (D) have already been proposed, and any of these known compounds may be used. Examples thereof include amines such as an aliphatic amine and an aromatic amine, and an aliphatic amine, and a secondary aliphatic amine or tertiary aliphatic amine is particularly preferable. Here, an "aliphatic amine" refers to an amine having one or more aliphatic groups, and the aliphatic groups preferably have 1 to 20 carbon atoms.

Examples of these aliphatic amines include amines in which at least one hydrogen atom of ammonia ($NH_3$) has been substituted with an alkyl group or hydroxyalkyl group of 1 to 20 carbon atoms (i.e., alkylamines or alkyl alcohol amines), and cyclic amines.

Specific examples of the alkylamines and alkyl alcohol amines include monoalkylamines such as n-hexylamine, n-heptylamine, n-octylamine, n-nonylamine, and n-decylamine; dialkylamines such as diethylamine, di-n-propylamine, di-n-heptylamine, di-n-octylamine, and dicyclohexylamine; trialkylamines such as trimethylamine, triethylamine, tri-n-propylamine, tri-n-butylamine, tri-n-hexylamine, tri-n-pentylamine, tri-n-heptylamine, tri-n-octylamine, tri-n-nonylamine, tri-n-decanylamine, and tri-n-dodecylamine; and alkyl alcohol amines such as diethanolamine, triethanolamine, diisopropanolamine, triisopropanolamine, di-n-octanolamine, tri-n-octanolamine, stearyl diethanolamine and lauryl diethanolamine. Among these, trialkylamines and/or alkyl alcohol amines are preferable.

Examples of the cyclic amine include heterocyclic compounds containing a nitrogen atom as a hetero atom. The heterocyclic compound may be a monocyclic compound (aliphatic monocyclic amine), or a polycyclic compound (aliphatic polycyclic amine).

Specific examples of the aliphatic monocyclic amine include piperidine and piperazine.

The aliphatic polycyclic amine preferably has 6 to 10 carbon atoms, and specific examples thereof include 1,5-diazabicyclo[4.3.0]-5-nonene, 1,8-diazabicyclo[5.4.0]-7-undecene, hexamethylenetetramine, and 1,4-diazabicyclo[2.2.2]octane.

Examples of other aliphatic amines include tris(2-methoxymethoxyethyl)amine, tris {2-(2-methoxyethoxy)ethyl}amine, tris{2-(2-methoxyethoxymethoxy)ethyl}amine, tris{2-(1-methoxyethoxy)ethyl}amine, tris{2-(1-ethoxyethoxy)ethyl}amine, tris{2-(1-ethoxypropoxy)ethyl}amine, and tris[2-{2-(2-hydroxyethoxy)ethoxy}ethyl]amine.

Further, as the component (D), an aromatic amine may also be used. Examples of aromatic amines include aniline, pyridine, 4-dimethylaminopyridine, pyrrole, indole, pyrazole, imidazole and derivatives thereof, diphenylamine, triphenylamine, tribenzylamine, 2,6-diisopropylaniline, 2,2'-dipyridyl, and 4,4'-dipyridyl.

These compounds can be used either alone, or in combinations of two or more different compounds.

The component (D) is typically used in an amount within a range from 0.01 to 5.0 parts by weight, relative to 100 parts by weight of the component (A).

Furthermore, in the resist composition of the present invention, for preventing any deterioration in sensitivity, and improving the resist pattern shape and the post exposure stability of the latent image formed by the pattern-wise exposure of the resist layer, at least one compound (E) (hereafter referred to as the component (E)) selected from the group consisting of an organic carboxylic acid, or a phosphorus oxo acid or derivative thereof can be added.

Examples of suitable organic carboxylic acids include acetic acid, malonic acid, citric acid, malic acid, succinic acid, benzoic acid, and salicylic acid.

Examples of phosphorus oxo acids or derivatives thereof include phosphoric acid, phosphonic acid and phosphinic acid. Among these, phosphonic acid is particularly desirable.

Examples of phosphorus oxo acid derivatives include esters in which a hydrogen atom within the above-mentioned oxo acids is substituted with a hydrocarbon group. Examples of the hydrocarbon group include an alkyl group of 1 to 5 carbon atoms and an aryl group of 6 to 15 carbon atoms.

Examples of phosphoric acid derivatives include phosphoric acid esters such as di-n-butyl phosphate and diphenyl phosphate.

Examples of phosphonic acid derivatives include phosphonic acid esters such as dimethyl phosphonate, di-n-butyl phosphonate, phenylphosphonic acid, diphenyl phosphonate and dibenzyl phosphonate.

Examples of phosphinic acid derivatives include phosphinic acid esters such as phenylphosphinic acid.

As the component (E), one type may be used alone, or two or more types may be used in combination.

As the component (E), an organic carboxylic acid is preferable, and salicylic acid is particularly desirable.

The component (E) is typically used in an amount within a range from 0.01 to 5.0 parts by weight, relative to 100 parts by weight of the component (A).

If desired, other miscible additives can also be added to the resist composition of the present invention. Examples of such miscible additives include additive resins for improving the performance of the resist film, surfactants for improving the applicability, dissolution inhibitors, plasticizers, stabilizers, colorants, halation prevention agents, and dyes.

<Organic Solvent>

The resist composition of the present invention can be prepared by dissolving the materials for the resist composition in an organic solvent (hereafter, frequently referred to as "component (S)").

The component (S) may be any organic solvent which can dissolve the respective components to give a uniform solution, and any one or more kinds of organic solvents can be appropriately selected from those which have been conventionally known as solvents for a chemically amplified resist.

Examples thereof include lactones such as γ-butyrolactone; ketones such as acetone, methyl ethyl ketone, cyclohexanone, methyl-n-pentyl ketone, methyl isopentyl ketone, and 2-heptanone; polyhydric alcohols, such as ethylene glycol, diethylene glycol, propylene glycol and dipropylene glycol; compounds having an ester bond, such as ethylene glycol monoacetate, diethylene glycol monoacetate, propylene glycol monoacetate, and dipropylene glycol monoacetate; polyhydric alcohol derivatives including compounds having an ether bond, such as a monoalkylether (e.g., monomethylether, monoethylether, monopropylether or monobutylether) or monophenylether of any of these polyhydric alcohols or compounds having an ester bond (among these, propylene glycol monomethyl ether acetate (PGMEA) and propylene glycol monomethyl ether (PGME) are preferable); cyclic ethers such as dioxane; esters such as methyl lactate, ethyl lactate (EL), methyl acetate, ethyl acetate, butyl acetate, methyl pyruvate, ethyl pyruvate, methyl methoxypropionate, and ethyl ethoxypropionate; aromatic organic solvents such as anisole, ethylbenzylether, cresylmethylether, diphenylether, dibenzylether, phenetole, butylphenylether, ethylbenzene, diethylbenzene, pentylbenzene, isopropylbenzene, toluene, xylene, cymene and mesitylene; and dimethyl sulfoxide (DMSO).

These organic solvents may be used individually, or as a mixed solvent containing two or more different solvents.

Among these, propylene glycol monomethyl ether acetate (PGMEA), propylene glycol monomethyl ether (PGME) and ethyl lactate (EL) are preferable.

Further, among the mixed solvents, a mixed solvent obtained by mixing PGMEA or PGME with a polar solvent is preferable. The mixing ratio (weight ratio) of the mixed solvent can be appropriately determined, taking into consideration the compatibility of the PGMEA or PGME with the polar solvent, but is preferably in a range from 1:9 to 9:1, and more preferably from 2:8 to 8:2.

Specifically, when EL is mixed as the polar solvent, the PGMEA:EL weight ratio is preferably from 1:9 to 9:1, and more preferably from 2:8 to 8:2. Alternatively, when PGME is mixed as the polar solvent, the PGMEA:PGME weight ratio is preferably from 1:9 to 9:1, more preferably from 2:8 to 8:2, and still more preferably 3:7 to 7:3.

Further, as the component (S), a mixed solvent of at least one of PGMEA and EL with γ-butyrolactone is also preferable. The mixing ratio (former:latter) of such a mixed solvent is preferably from 70:30 to 95:5.

Further, a mixed solvent of PGME with dimethyl sulfoxide is also preferable. In this case, the mixing ratio (former:latter) of such a mixed solvent is preferably from 9:1 to 1:9, more preferably from 8:2 to 2:8, and most preferably from 7:3 to 5:5.

The amount of the component (S) is not particularly limited, and is adjusted appropriately to a concentration that enables application of a coating solution to a substrate in accordance with the thickness of the coating film. In general, the component (S) is used in an amount that yields a solid content for the resist composition that is within a range from 2 to 20% by weight, and preferably from 3 to 15% by weight.

Dissolving of the materials for a resist composition in the component (S) can be conducted by simply mixing and stirring each of the above components together using conventional methods, and where required, the composition may also be mixed and dispersed using a dispersion device such as a dissolver, a homogenizer, or a triple roll mill. Furthermore, following mixing, the composition may also be filtered using a mesh, a membrane filter, or the like.

The resist composition of the present invention is a novel resist composition containing the component (B1); i.e., a novel acid generator which was conventionally unknown.

Moreover, in the present invention, the level of defects can also be reduced. The term "defects" refers to general abnormalities within a resist film that are detected when observed from directly above the developed resist film using, for example, a surface defect detection apparatus (product name: "KLA") manufactured by KLA-TENCOR Corporation. Examples of these abnormalities include post-developing scum, foam, dust, bridges (structures that bridge different portions of the resist pattern), color irregularities, foreign deposits, and residues.

As the miniaturization of resist patterns progress, in the formation of a resist pattern using the conventional techniques, problems have arisen, including formation of T-top shapes in line and space patterns and occurrence of "Not Open" defects in contact hole patterns. In particular, the occurrence of "Not Open" defects in contact hole patterns has become a serious problem. However, these problems can be ameliorated by the use of the resist composition of the present invention which contains the component (B1).

The reason that this effect is obtained is not entirely clear, but is thought to be due to the fact that because a fluorinated alkyl group having a low surface free energy is introduced to the cation moiety of the component (B1), when a resist film is formed using the resist composition of the present invention, uneven distribution of the component (B1) near the resist film surface is observed. That is, it is presumed that due to uneven distribution of the component (B1) that includes a fluorinated alkyl group with high water repellency in the resist film surface, generation of acid and its diffusion efficiency during exposure and post exposure baking (PEB) are enhanced, and as a result, solubility of the component (A) in an alkali developing solution can be increased or reduced efficiently (which results in, for example, promotion of the deprotection of the acid dissociable, dissolution inhibiting group when using a positive resist composition), thereby improving the shape of the resist pattern and ameliorating "Not Open" defects.

Furthermore, the resist composition of the present invention also exhibits favorable levels of lithographic properties such as sensitivity, depth of focus (DOF), and in-plane uniformity (CDU) of the dimensions (CD) of the formed resist patterns. Excellent levels of CDU are achieved especially when a resist pattern is formed in a narrow pitch. For example, in the formation of a hole pattern within a narrow pitch, a hole pattern having an excellent shape can be formed without causing the connection of hole edges or exhibiting poor removability (namely, poor resolution).

Further, the resist composition of the present invention has the properties required of a resist composition used in immersion lithography, namely, favorable lithographic properties and favorable properties (particularly hydrophobicity) for use within an immersion exposure process, and can therefore be used very favorably for immersion exposure.

That is, by including the component (B1) composed of the compound (b-11) of the present invention, a resist film formed using the resist composition of the present invention has a high level of hydrophobicity. In other words, since the component (B1) includes a substituent containing a fluorine atom in the cation moiety thereof, a resist film formed using the resist composition of the present invention has a higher level of hydrophobicity than a resist film that does not include the component (B1).

Such a resist film with improved hydrophobicity exhibits an extremely favorable water tracking ability, which is required when the immersion exposure is performed using a scanning-type immersion exposure apparatus.

The hydrophobicity of a resist film can be evaluated by measuring the contact angle thereof against water, for example, the static contact angle (the contact angle between the surface of a water droplet on the resist film in a horizontal state and the resist film surface), the dynamic contact angle (the contact angle at which a water droplet starts to slide when the resist film is inclined (sliding angle), the contact angle at the front-end point of the water droplet in the sliding direction (advancing angle) and the contact angle at the rear-end point of the water droplet in the sliding direction (receding angle)). For example, the higher the hydrophobicity of a resist film, the higher the static angle, advancing angle and receding angle, and smaller the sliding angle.

As shown in FIG. 1, when a flat surface 2 with a liquid droplet 1 placed thereon is gradually inclined, the advancing angle describes the angle $\theta 1$ between the surface of the liquid droplet at the bottom edge $1a$ of the liquid droplet 1 and the flat surface 2 when the liquid droplet 1 starts to move (slide) down the flat surface 2. Further, at this point (the point when the liquid droplet 1 starts to move (slide) down the flat surface 2), the angle $\theta 2$ between the surface of the liquid droplet at the top edge $1b$ of the liquid droplet 1 and the flat surface 2 is the receding angle, and the inclination angle $\theta 3$ of the flat surface 2 is the sliding angle.

In the present description, the advancing angle, the receding angle, and the sliding angle are measured in the following manner.

First, a resist composition solution is spin-coated onto a silicon substrate, and is then heated at a temperature of 110° C. for 60 seconds to form a resist film. Subsequently, the contact angles for the resist film can be measured using a commercially available measurement apparatus such as a DROP MASTER-700 (product name, manufactured by Kyowa Interface Science Co. Ltd.), AUTO SLIDING ANGLE: SA-30DM (product name, manufactured by Kyowa Interface Science Co. Ltd.), or AUTO DISPENSER: AD-31 (product name, manufactured by Kyowa Interface Science Co. Ltd.).

With respect to the resist film obtained using the resist composition of the present invention, the static contact angle measured prior to exposure and developing is preferably 70 degrees or more, more preferably from 70 to 100 degrees, and most preferably from 75 to 100 degrees. When the static contact angle is at least as large as 70 degrees, the suppression effect on substance elution during the immersion exposure is enhanced. The reason for this has not been elucidated yet, but it is presumed that one of the main reasons is related to the hydrophobicity of the resist film. More specifically, it is presumed that since an aqueous substance such as water is used as the immersion medium, higher hydrophobicity has an influence on the swift removal of the immersion medium from the surface of the resist film after the immersion exposure. On the other hand, when the receding angle is no higher than 100 degrees, the lithography properties become satisfactory.

For similar reasons, with respect to the resist film obtained using the resist composition of the present invention, the receding angle measured prior to exposure and developing is preferably 50 degrees or more, more preferably from 50 to 150 degrees, still more preferably 50 to 130 degrees, and most preferably from 53 to 100 degrees.

Furthermore, with respect to the resist film obtained using the resist composition of the present invention, the sliding angle measured prior to exposure and developing is preferably no more than 30 degrees, more preferably from 5 to 30 degrees, still more preferably from 5 to 25 degrees, and most preferably from 5 to 23 degrees. When the sliding angle is no higher than 30 degrees, the suppression effect on substance elution during the immersion exposure is enhanced. On the other hand, when the sliding angle is at least as large as 5 degrees, the lithography properties become satisfactory.

The magnitude of the various angles described above (the dynamic contact angles (advancing angle, receding angle, and sliding angle) and the static contact angle) can be adjusted by adjusting the formulation for the resist composition (for example, by varying the amount of the component (B1), varying the formulation (namely, the type and proportion of structural units) of the component (A), and adding a fluorine-containing additive). For example, by increasing the amount of the component (B1), the hydrophobicity of the obtained resist composition can be enhanced, and the advancing angle, the receding angle and the static contact angle becomes large, whereas the sliding angle becomes small.

Further, by using the resist composition of the present invention, elution of a substance from the resist film during immersion exposure can be suppressed.

That is, as described later in detail, immersion exposure is a method in which exposure (immersion exposure) is conducted in a state where the region between the lens and the resist layer formed on a wafer (which is conventionally filled with air or an inert gas such as nitrogen) is filled with a solvent (an immersion medium) that has a larger refractive index than the refractive index of air. In immersion exposure, when the resist film comes into contact with the immersion medium, elution of substances within the resist film (component (B), component (D), and the like) into the immersion medium occurs. This elution of a substance causes phenomenon such as degeneration of the resist film and change in the refractive index of the immersion medium, thereby adversely affecting the lithographic properties. The amount of the eluted substance is affected by the properties of the resist film surface (e.g., hydrophilicity, hydrophobicity, and the like). For example, by enhancing the hydrophobicity of the resist film surface, it is presumed that the degree of substance elution can be reduced.

As a resist film formed using the resist composition of the present invention includes the component (B1), the resist film exhibits a higher level of hydrophobicity than a resist film that does not include the component (B1). Therefore, according to the resist composition of the present invention, elution of a substance during immersion exposure can be suppressed.

Because it enables suppression of substance elution, using the resist composition of the present invention also enables suppression of degeneration of the resist film and variation in the refractive index of the immersion solvent during immersion exposure. By suppressing fluctuation in the refractive index of the immersion solvent, a resist pattern having an excellent shape can be formed. Further, staining of the lens of the exposure apparatus can also be reduced. As a result, protective measures for preventing such staining need not be performed, which contributes to a simplification of both the process and the exposure apparatus.

Furthermore, a resist film formed using the resist composition of the present invention is resistant to swelling in water. Therefore, a very fine resist pattern can be formed with a high level of precision.

Also, the resist composition of the present invention also exhibits favorable lithographic properties such as sensitivity, resolution and etching resistance, and when used as a resist in an actual immersion exposure, is capable of forming a favorable resist pattern without any practical difficulties. For example, by using the resist composition of the present invention, a very fine resist pattern with dimensions of, for example, not more than 120 nm can be formed.

<<Method of Forming a Resist Pattern>>

The method of forming a resist pattern according to the present invention includes: forming a resist film on a substrate using the resist composition according to the first aspect of the present invention, subjecting the resist film to immersion exposure, and subjecting the resist film to alkali developing to form a resist pattern.

A preferred example of the method of forming a resist pattern according to the present invention is described below, where a resist film is exposed by the immersion exposure. However, the present invention is not limited to the above example, and the exposure of the resist film can be performed through a general exposure (dry exposure) which is conducted in air or in an inert gas such as nitrogen.

Firstly, a resist composition of the present invention is applied onto a substrate using a spinner or the like, and a prebake (post applied bake (PAB)) is conducted to form a resist film.

The substrate is not specifically limited and a conventionally known substrate can be used. For example, the substrate can be exemplified by substrates for electronic components, and such substrates having wiring patterns formed thereon. Specific examples thereof include a silicon wafer, a substrate made of metals such as copper, chromium, iron and aluminum, and a glass substrate. Suitable materials for the wiring pattern include copper, aluminum, nickel, and gold. Further, as the substrate, any one of the above-exemplified substrates provided with an inorganic and/or organic film on the surface thereof may also be used. As the inorganic film, an inorganic antireflection film (inorganic BARC) can be used. As the organic film, an organic antireflection film (organic BARC) and an organic film such as a lower-layer organic film used in a multilayer resist method can be used.

Here, a "multilayer resist method" is a method in which at least one layer of an organic film (lower-layer organic film) and at least one layer of a resist film (upper resist film) are provided on a substrate, and a resist pattern formed on the upper resist film is used as a mask to conduct patterning of the lower-layer organic film. This method is considered as being capable of forming a pattern with a high aspect ratio. More specifically, in the multilayer resist method, a desired thickness can be ensured by the lower-layer organic film, and as a result, the thickness of the resist film can be reduced, and an extremely fine pattern with a high aspect ratio can be formed.

The multilayer resist method can be broadly classified into a method in which a double-layer structure consisting of an upper-layer resist film and a lower-layer organic film is formed (a double-layer resist method), and a method in which a multilayer structure having at least three layers consisting of an upper-layer resist film, a lower-layer organic film and at least one intermediate layer (thin metal film or the like) provided between the upper-layer resist film and the lower-layer organic film is formed (a three-layer resist method).

After formation of a resist film, an organic antireflection film may be provided on the resist film, thereby forming a triple layer laminate consisting of the substrate, the resist film and the antireflection film. The antireflection film provided on top of the resist film is preferably soluble in an alkali developing solution.

The steps up until this point can be conducted by using conventional techniques. The operating conditions and the like are preferably selected appropriately in accordance with the formulation and the characteristics of the resist composition being used.

Subsequently, the obtained resist film is subjected to selective immersion exposure (liquid immersion lithography) through a desired mask pattern. At this time, the region between the resist film and the lens at the lowermost point of the exposure apparatus is pre-filled with a solvent (immersion medium) that has a larger refractive index than the refractive index of air, and the exposure (immersion exposure) is conducted in this state.

There are no particular limitations on the wavelength used for the exposure, and an ArF excimer laser, a KrF excimer laser, an $F_2$ laser, or the like can be used. The resist composition according to the present invention is effective for KrF and ArF excimer lasers, and is particularly effective for an ArF excimer laser.

The immersion medium preferably exhibits a refractive index larger than the refractive index of air but smaller than the refractive index of the resist film formed from the resist composition of the present invention. The refractive index of the immersion medium is not particularly limited as long as it satisfies the above-mentioned requirements.

Examples of this immersion medium that exhibits a refractive index that is larger than the refractive index of air but smaller than the refractive index of the resist film include water, fluorine-based inert liquids, silicon-based solvents and hydrocarbon-based solvents.

Specific examples of the fluorine-based inert liquids include liquids containing a fluorine-based compound such as $C_3HCl_2F_5$, $C_4F_9OCH_3$, $C_4F_9OC_2H_5$ and $C_5H_3F_7$ as the main component, which have a boiling point within a range from 70 to 180° C. and preferably from 80 to 160° C. A fluorine-based inert liquid having a boiling point within the above-mentioned range is advantageous in that the removal of the immersion medium after the exposure can be conducted by a simple method.

As a fluorine-based inert liquid, a perfluoroalkyl compound in which all of the hydrogen atoms of the alkyl group are substituted with fluorine atoms is particularly desirable. Examples of these perfluoroalkyl compounds include perfluoroalkylether compounds and perfluoroalkylamine compounds.

Specifically, one example of a suitable perfluoroalkylether compound is perfluoro(2-butyl-tetrahydrofuran) (boiling point 102° C.), and an example of a suitable perfluoroalkylamine compound is perfluorotributylamine (boiling point 174° C.).

A resist composition of the present invention is particularly resistant to any adverse effects caused by water, and because the resulting lithographic properties such as the sensitivity and shape of the resist pattern profile are excellent, water is preferably used as the immersion medium in the present invention. Furthermore, water is also preferred in terms of cost, safety, environmental friendliness, and versatility.

Subsequently, following completion of the immersion exposure step, post exposure baking (PEB) is conducted. A PEB treatment is typically conducted under temperature conditions of 80 to 150° C. for 40 to 120 seconds, preferably 60 to 90 seconds.

Subsequently, developing is conducted using an alkali developing solution composed of an aqueous alkali solution such as a 0.1 to 10% by weight aqueous solution of tetramethylammonium hydroxide (TMAH).

Thereafter, a water rinse is preferably conducted with pure water. This water rinse can be conducted, for example, by dripping or spraying water onto the surface of the substrate while rotating the substrate, and washes away the developing solution and those portions of the resist composition that have been dissolved by the developing solution.

By subsequently drying the resist, a resist pattern is obtained in which the resist film (the coating of the resist composition) has been patterned into a shape faithful to the mask pattern.

<<Compound>>

A compound according to the third aspect of the present invention is a compound represented by the aforementioned general formula (b1-11) (hereafter, referred to as "compound (b1-11)").

The compound (b1-11) is the same as the component (B1) in the resist composition according to the first aspect of the present invention.

The compound (b1-11) is a novel compound that has been unknown until now. Further, the compound (b1-11) is useful as an acid generator of a resist composition.

The compound (b1-11) can be produced by using normal methods.

More specifically, for example, when $R^{7''}$ in the aforementioned general formula (b-11) is an aryl group having one group represented by the aforementioned formula (I), the compound (hereafter, referred to as "compound (b1-11-1)") can be produced as follows.

First, a compound represented by general formula (b1-01) shown below is added to an organic solvent (for example, acetone, dichloromethane, tetrahydrofuran or the like) and cooled, and a compound represented by general formula (b1-02) shown below are added thereto, and reacted. The resultant is subjected to liquid separation and washing with water, to thereby obtain a compound represented by general formula (b1-03) shown below from the organic phase.

The compound represented by general formula (b1-03) shown below and a compound represented by general formula (b1-04) shown below are added to a solution of an organic acid $H^+B^-$ (wherein $B^-$ represents an anion moiety of an organic acid, such as methanesulfonic acid ion), and reacted. Then, pure water and an organic solvent (for example, t-butyl methyl ether (TBME), dichloromethane, tetrahydrofuran or the like) are added thereto, and the organic phase is collected, to thereby obtain a compound represented by general formula (b1-05) shown below from the organic phase.

Subsequently, the compound represented by general formula (b1-05) shown below is dissolved in a mixed solvent of an organic solvent (for example, dichloromethane, tetrahydrofuran or the like) and water. Then, an alkali metal salt $L^+X^-$ (wherein $L^+$ represents an alkali metal cation such as a lithium ion or potassium ion) having a desired anion $X^-$ is added thereto, and reacted. The resultant is subjected to liquid separation and washing with water, to thereby obtain a compound represented by general formula (b1-11-1) shown below (namely, the compound (b1-11-1)) from the organic phase.

[Chemical Formula 59]

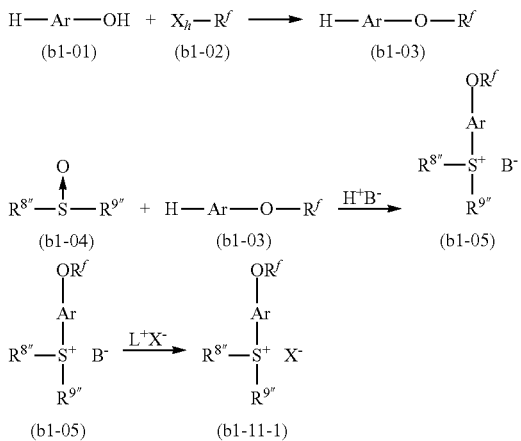

In formulas in the production example of the compound (b1-11-1), $R^{8'''}$ to $R^{9'''}$ and $X^-$ are the same as $R^{8'''}$ to $R^{9'''}$ and $X^-$ in general formula (b1-11) above; $R^f$ is the same as $R^f$ in general formula (I) above; Ar represents an arylene group; $B^-$ represents an anion moiety of an organic acid; $L^+$ represents an alkali metal cation; and $X_h$ represents a halogen atom.

Examples of the arylene group for Ar include a group which is the aryl group exemplified above for $R^{7'''}$ to $R^{9'''}$ in the aforementioned general formula (b1-11) having one hydrogen atom removed therefrom.

As the halogen atom for $X_h$, a bromine atom or a chlorine atom is preferable.

The structure of the obtained compound can be confirmed by a general organic analysis method such as $^1$H-nuclear magnetic resonance (NMR) spectrometry, $^{13}$C-NMR spectrometry, $^{19}$F-NMR spectrometry, infrared absorption (IR) spectrometry, mass spectrometry (MS), elementary analysis and X-ray diffraction analysis.

<<Acid Generator>>

An acid generator according to the fourth aspect of the present invention is an acid generator including the compound according to the third aspect of the present invention.

The acid generator is added to a resist composition for use. The resist composition to which the acid generator is added can be used for both dry exposure and immersion exposure, and is especially suited for immersion exposure.

There are no particular limitations on the resist composition to which the acid generator is added, although a chemically amplified resist composition including a base component that exhibits changed solubility in an alkali developing solution under the action of acid, and an acid generator component that generates acid upon exposure is ideal.

EXAMPLES

As follows is a more detailed description of the present invention based on a series of examples, although the scope of the present invention is in no way limited by these examples.

In the NMR analysis, tetramethylsilane (TMS) was used as an internal standard in $^1$H-NMR spectrometry, and hexafluorobenzene was used as an internal standard in $^{19}$F-NMR spectrometry (the peak of hexafluorobenzene was regarded as −160 ppm).

Synthesis Example 1

150 g of methyl fluorosulfonyl(difluoro)acetate and 375 g of pure water were kept at 10° C. or lower in an ice bath, and 343.6 g of a 30% aqueous solution of sodium hydroxide was dropwise added thereto. Following completion of the dropwise addition, the resultant was refluxed at 100° C. for 3 hours, followed by cooling and neutralizing with concentrated hydrochloric acid. The resulting solution was dropwise added to 8,888 g of acetone, and the precipitate was collected by filtration and dried, thereby obtaining 184.5 g of a compound (1-1), represented by a structural formula shown below, in the form of a white solid (purity: 88.9%, yield: 95.5%).

[Chemical Formula 60]

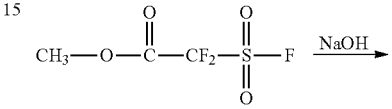

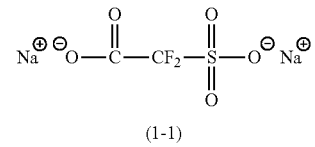

(1-1)

56.2 g of the above-mentioned compound (1-1) and 562.2 g of acetonitrile were prepared, and 77.4 g of p-toluenesulfonic acid monohydrate was added thereto. The resultant was refluxed at 110° C. for 3 hours. Then, the reaction liquid was filtered, and the filtrate was concentrated and dried to obtain a solid. 900 g of t-butyl methyl ether was added to the obtained solid and stirred. Thereafter, the resultant was filtered, and the residue was dried, thereby obtaining 22.2 g of a compound (1-2), represented by a structural formula shown below, in the form of a white solid (purity: 91.0%, yield: 44.9%).

[Chemical Formula 61]

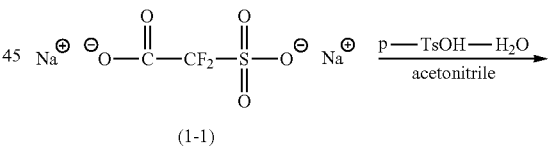

(1-1)

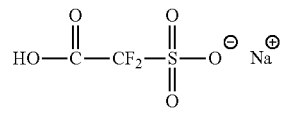

(1-2)

4.34 g of the above-mentioned compound (1-2) (purity: 94.1%), 3.14 g of 2-benzyloxyethanol and 43.4 g of toluene were prepared, and 0.47 g of p-toluenesulfonic acid monohydrate was added thereto. The resultant was refluxed at 105° C. for 20 hours. Then, the reaction liquid was filtered, and 20 g of hexane was added to the residue and stirred. Thereafter, the resultant was filtered, and the residue was dried, thereby obtaining 1.41 g of a compound (1-3) represented by a structural formula shown below (yield: 43.1%).

[Chemical Formula 62]

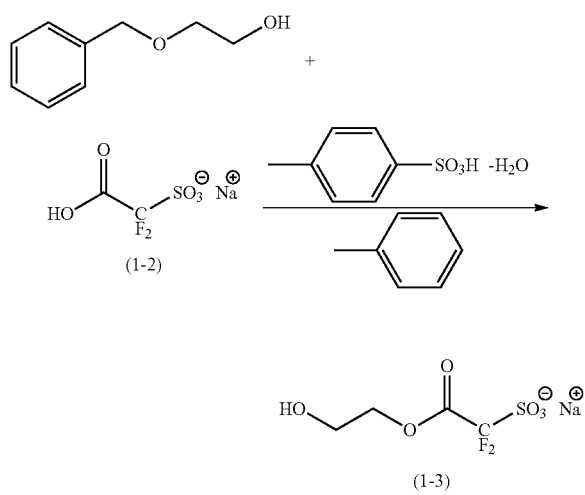

1.00 g of the above-mentioned compound (1-3) and 3.00 g of acetonitrile were prepared, and 0.82 g of 1-adamantanecarbonyl chloride and 0.397 g of triethylamine were dropwise added thereto while cooling with ice. Following completion of the dropwise addition, the resultant was stirred at room temperature for 20 hours and was then filtered. The obtained filtrate was concentrated and solidified, and was then dissolved in 30 g of dichloromethane, followed by washing with water three times. Thereafter, the resulting organic layer was concentrated and dried, thereby obtaining 0.82 g of a compound (1-4) represented by a structural formula shown below (yield: 41%).

[Chemical Formula 63]

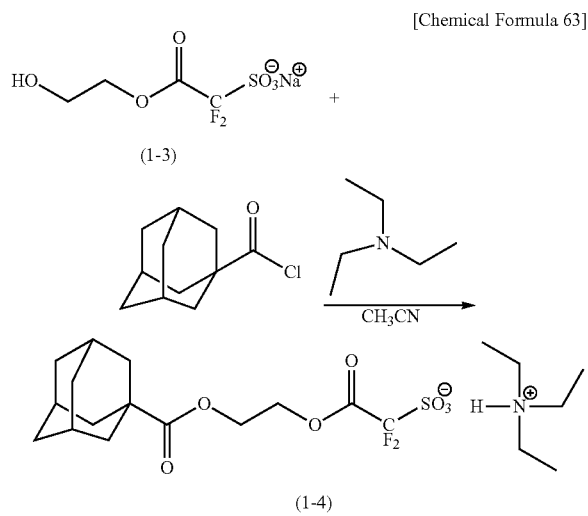

The obtained compound (1-4) was analyzed by NMR.

$^1$H-NMR (DMSO-d6, 400 MHz): δ (ppm)=8.81 (s, 1H, H$^c$), 4.37-4.44 (t, 2H, H$^d$), 4.17-4.26 (t, 2H, H$^e$), 3.03-3.15 (q, 6H, H$^b$), 1.61-1.98 (m, 15H, Adamantine), 1.10-1.24 (t, 9H, H$^a$).

$^{19}$F-NMR (DMSO-d6, 376 MHz): δ (ppm)=−106.6.

From the results above, it was confirmed that the compound (1-4) had a structure shown below.

[Chemical Formula 64]

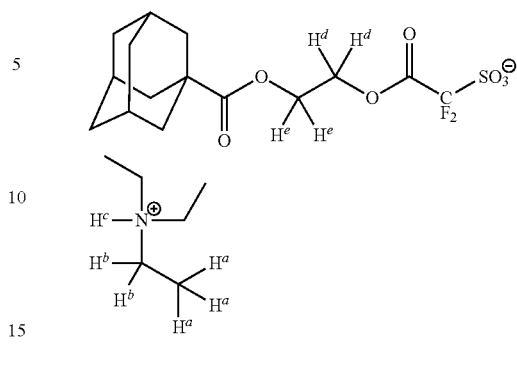

Synthesis Example 2

3.63 g of 2,6-dimethylphenol and 72.65 g of acetone were charged into a three-necked flask, and 12.34 g of potassium carbonate was then added thereto. The resultant was stirred for 30 minutes, and 23.22 g of 4,4,5,5,6,6,7,7,7-nonafluorobutyl iodide was then added thereto, and a reaction was effected at 40° C. for 19 hours. The reaction solution was cooled to room temperature and was filtered, and the resulting filtrate was solidified. 11.37 g of t-butyl methyl ether (TBME) was then added to the obtained solid, and the resultant was washed four times with 11.37 g of pure water. The resultant was then subjected to liquid separation to collect the organic phase, and the obtained organic phase was concentrated, and was then purified by distillation, thereby obtaining 8.88 g of a compound (2-1).

The compound (2-1) was analyzed by NMR.

$^1$H-NMR (DMSO-d6, 400 MHz): δ (ppm)=2.03-2.10 (m, 2H, H$^b$), 2.23 (m, 6H, H$^d$), 2.43-2.55 (m, 2H, H$^a$), 3.85 (t, 2H, H$^c$), 6.91-7.03 (m, 3H, H$^e$).

$^{19}$F-NMR (DMSO-d6, 376 MHz): δ (ppm)=−123.5, −121.8, −111.6, −78.3.

From the results shown above, it was confirmed that the compound (2-1) had a structure shown below.

[Chemical Formula 65]

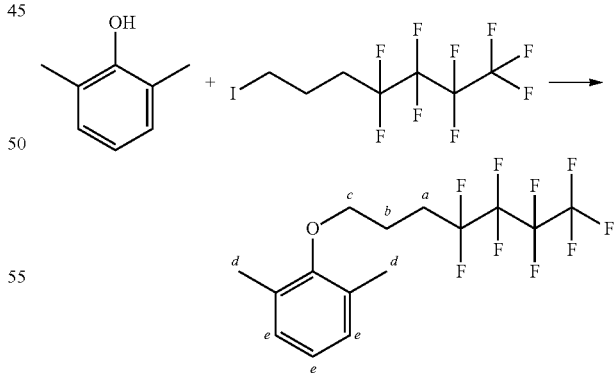

Subsequently, 2.64 g of diphosphorus pentaoxide was added to 38.4 g of methanesulfonic acid while stirring, and 8.55 g of the compound (2-1) represented by the above structural formula and 1.88 g of diphenylsulfoxide were then added gradually thereto while being cooled with ice. Thereafter, the resultant was stirred for 24 hours at room temperature, and the obtained reaction solution was then gradually added dropwise to a mixed solvent of 91.3 g of pure water and 152.1 g of TBME. Then, liquid separation was conducted to obtain a water phase. The obtained water phase was washed twice with 91.3 g of TBME, and was then extracted twice with 91.3 g of dichloromethane, and the obtained dichloromethane phase was concentrated to thereby obtain 7.4 g of a compound (2-2) in the form of a viscous solid.

The compound (2-2) was analyzed by NMR.

$^1$H-NMR (DMSO-d6, 400 MHz): δ (ppm)=2.03-2.56 (m, 13H, $H^a$+$H^b$+$H^d$+$H^e$), 3.97 (t, 2H, $H^c$), 7.62 (s, 2H, Ar), 7.75-7.87 (m, 10H, Ar).

$^{19}$F-NMR (DMSO-d6, 376 MHz): δ (ppm)=−123.5, −121.8, −111.6, −78.3.

From the results shown above, it was confirmed that the compound (2-2) had the structure shown below.

[Chemical Formula 66]

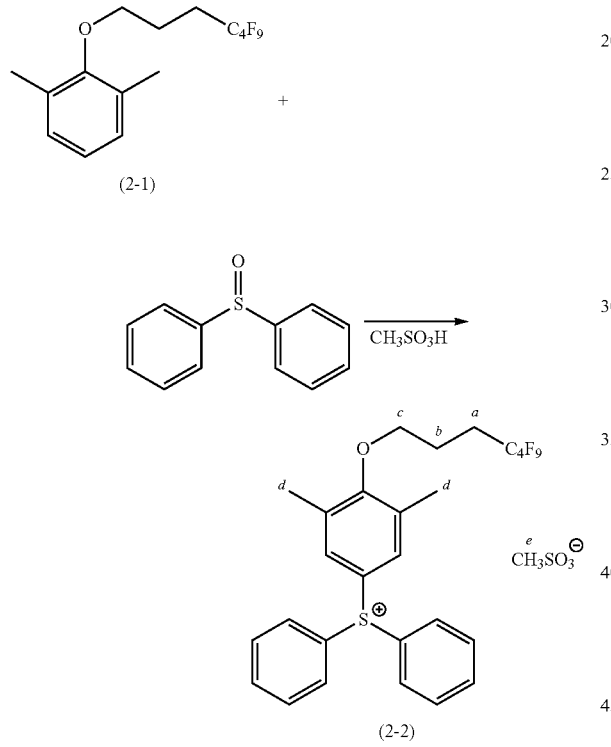

Synthesis Example 3

8.82 g of pure water and 8.82 g of dichloromethane were added to 2.09 g of the compound (2-2) having the above-mentioned structure, and 1.27 g of a compound (1-4) represented by a structural formula shown below was then added thereto, and the resultant was stirred at room temperature for 3 hours. Thereafter, the resultant was subjected to liquid separation to collect a dichloromethane phase, and the obtained dichloromethane phase was washed twice with 8.82 g of diluted hydrochloric acid, and was then washed four times with 8.82 g of pure water. The resulting dichloromethane phase was concentrated and solidified, thereby obtaining 2.02 g of a compound (3-1) in the form of a white solid.

The compound (3-1) was analyzed by NMR.

$^1$H-NMR (DMSO-d6, 400 MHz): δ (ppm)=1.60-1.91 (m, 15H, adamantane), 2.03-2.56 (m, 10H, $H^a$+$H^b$+$H^d$), 3.97 (t, 2H, $H^c$), 4.20 (t, 2H, $H^e$), 4.41 (t, 2H, $H^f$), 7.59 (s, 2H, Ar), 7.71-7.89 (m, 10H, Ar).

$^{19}$F-NMR (DMSO-d6, 376 MHz): δ (ppm)=−123.1, −121.4, −111.0, −106.7, −77.9.

From the results shown above, it was confirmed that the compound (3-1) had a structure shown below.

[Chemical Formula 67]

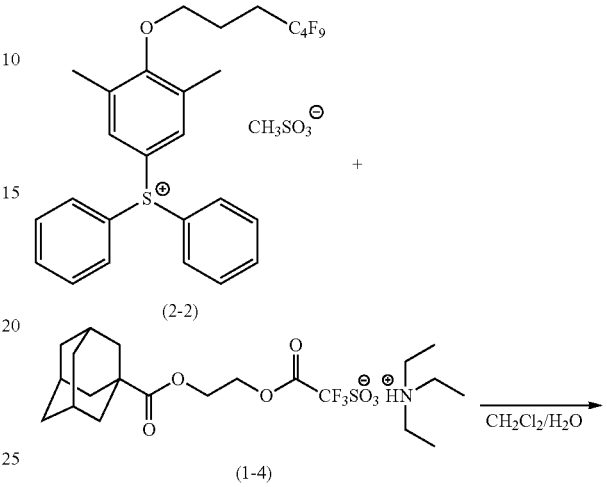

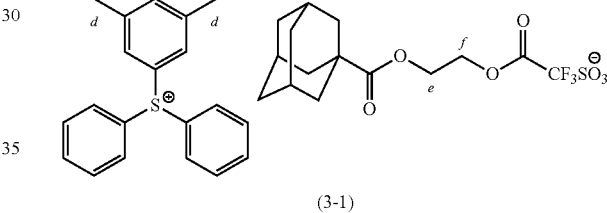

Synthesis Example 4

0.384 g of the compound (4-1) represented by a structural formula shown below was dissolved in 3.84 g of dichloromethane and 3.84 g of water, and 0.40 g of the compound (1-4) represented by a structural formula shown below was then added to the resulting solution. The resultant was stirred for 1 hour, and was then subjected to liquid separation to collect an organic phase. The obtained organic phase was washed three times with 3.84 g of water. Thereafter, the resulting organic phase was concentrated and solidified, thereby obtaining 0.44 g of a compound (4-2) (yield: 81.5%).

[Chemical Formula 68]

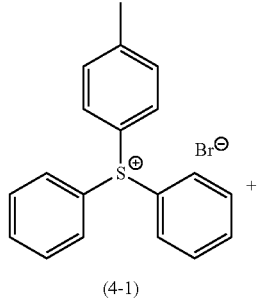

-continued

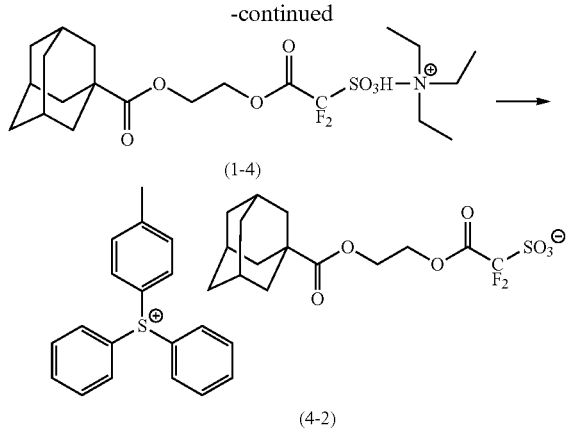

The obtained compound (4-2) was analyzed by NMR.
$^1$H-NMR (DMSO-d6, 400 MHz): δ (ppm)=7.57-7.87 (m, 14H, Phenyl), 4.40-4.42 (t, 2H, H$^b$), 4.15-4.22 (t, 2H, H$^a$), 2.43 (s, 3H$^c$), 1.60-1.93 (m, 15H, Adamantane).
$^{19}$F-NMR (DMSO-d6, 376 MHz): δ (ppm)=−106.7.
From the results shown above, it was confirmed that the compound (4-2) had the structure shown below.

[Chemical Formula 69]

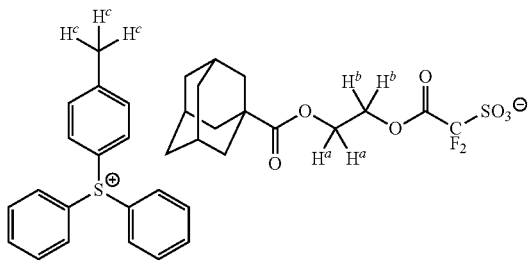

Synthesis Example 5

Synthesis of [Compound 3] (Monomer)

(i)
37.6 g (494 mmol) of glycolic acid, 700 mL of dimethylformamide (DMF), 86.5 g (626 mmol) of potassium carbonate, and 28.3 g (170 mmol) of potassium iodide were charged into a 2 L three-necked flask equipped with a thermometer, a cooling pipe, and a stirrer, followed by being stirring at room temperature for 30 minutes. Then, 300 mL of a dimethylformamide solution containing 100 g (412 mmol) of 2-methyl-2-adamantyl chloroacetate was gradually added thereto. The resultant was heated to 40° C., and was then stirred for 4 hours. Following the completion of the reaction, 2,000 mL of diethyl ether was added to the reaction mixture, followed by filtration. The resulting solution was washed three times with 500 mL of distilled water, followed by crystallization using a mixed solution containing 300 mL of toluene and 200 mL of heptane, thereby obtaining 78 g of an objective compound (namely, 2-(2-(2-methyl-2-adamantyloxy)-2-oxoethoxy)-2-oxoethanol) in the form of a colorless solid (yield: 67%, GC purity: 99%).
The results of instrumental analysis of the obtained compound were as follows.
$^1$H-NMR: 1.59 (d, 2H, J=12.5 Hz), 1.64 (s, 3H), 1.71-1.99 (m, 10H), 2.29 (m, 2H), 2.63 (t, 1H, J=5.2 Hz), 4.29 (d, 2H, J=5.2 Hz), 4.67 (s, 2H).
$^{13}$C-NMR: 22.35, 26.56, 27.26, 32.97, 34.54, 36.29, 38.05, 60.54, 61.50, 89.87, 165.97, 172.81.
GC-MS: 282 (M$^+$, 0.02%), 165 (0.09%), 149 (40%), 148 (100%), 133 (22%), 117 (2.57%), 89 (0.40%).
From the results shown above, it was confirmed that the obtained compound was 2-(2-(2-methyl-2-adamantyloxy)-2-oxoethoxy)-2-oxoethanol.

(ii)
165 g (584 mmol) of 2-(2-(2-methyl-2-adamantyloxy)-2-oxoethoxy)-2-oxoethanol, 2,000 mL of tetrahydrofuran (THF), 105 mL (754 mmol) of triethylamine, and 0.165 g (1,000 ppm) of p-methoxyphenol were added to and dissolved in a 2 L three-necked flask equipped with a thermometer, a cooling pipe, and a stirrer. Following the completion of the dissolution, 62.7 mL (648 mmol) of methacryloyl chloride was gradually added thereto while cooling in an ice bath. The temperature of the resultant was elevated to room temperature, and the resultant was stirred for 3 hours. Following the completion of the reaction, 1,000 mL of diethyl ether was added thereto, followed by washing with 200 mL of distilled water 5 times. Thereafter, the extraction liquid was concentrated, thereby obtaining 198 g of an objective compound [compound 3] in the form of a colorless liquid (yield: 97%, GC purity: 99%).
The results of instrumental analysis of the obtained [compound 3] were as follows.
$^1$H-NMR: 1.58 (d, J=12.5 Hz, 2H), 1.63 (s, 3H), 1.71-1.89 (m, 8H), 1.98 (s, 3H), 2.00 (m, 2H), 2.30 (m, 2H), 4.62 (s, 2H), 4.80 (s, 2H), 5.66 (m, 1H), 6.23 (m, 1H).
$^{13}$C-NMR: 18.04, 22.15, 26.42, 27.14, 32.82, 34.38, 36.11, 37.92, 60.44, 61.28, 89.42, 126.79, 135.18, 165.61, 166.30, 167.20.
GC-MS: 350 (M$^+$, 1.4%), 206 (0.13%), 149 (47%), 148 (100%), 133 (20%), 69 (37%).

Synthesis Example 6

Synthesis of Polymer Compound (1)

5.10 g (30 mmol) of a [compound 1] represented by a structural formula shown below, 17.38 g (70 mmol) of a [compound 2] represented by a structural formula shown below, 7.00 g (20 mmol) of a [compound 3] represented by a structural formula shown below, and 5.67 g (24 mmol) of a [compound 4] represented by a structural formula shown below were charged into to a 500 mL beaker, and were dissolved in 55.13 g of methyl ethyl ketone. Then, 4.0 mmol of dimethyl azobisisobutyrate (V-601) as a polymerization initiator was added to and dissolved in the resulting solution. The reaction solution was dropwise added to 30.62 g of methyl ethyl ketone heated to 75° C. in a separable flask over 6 hours in a nitrogen atmosphere. Following completion of the dropwise addition, the reaction solution was heated for 1 hour while stirring, and was then cooled to room temperature. The resulting polymerization solution was concentrated under reduced pressure, and was dropwise added to an excess amount of a mixed solution containing methanol and water so as to precipitate a reaction product (copolymer). The precipitated reaction product was separated by filtration, followed by washing and drying, thereby obtaining 15 g of a polymer compound (1) as an objective compound.
With respect to the polymer compound (1), the weight average molecular weight (Mw) and the dispersity (Mw/Mn) were determined by the polystyrene equivalent value as measured by gel permeation chromatography (GPC). As a result, it was found that the weight average molecular weight was 7,000, and the dispersity was 2.0.
Further, the polymer compound (1) was analyzed by carbon 13 nuclear magnetic resonance spectroscopy (600 MHz, $^{13}$C-NMR). As a result, it was found that the composition of the copolymer (ratio (molar ratio) of the respective structural units within the structural formula shown below) was l/m/n/o=25.3/35.3/14.8/24.6.

[Chemical Formula 70]

Compound 1
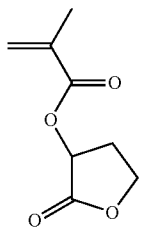

Compound 2
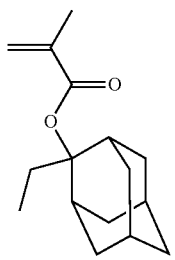

Compound 3
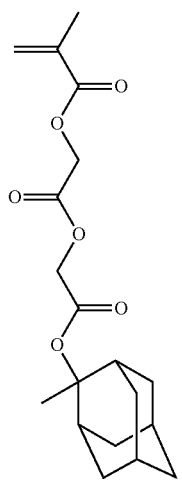

Compound 4
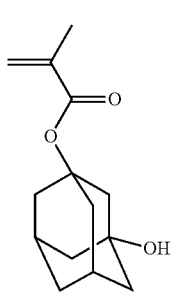

[Chemical Formula 71]

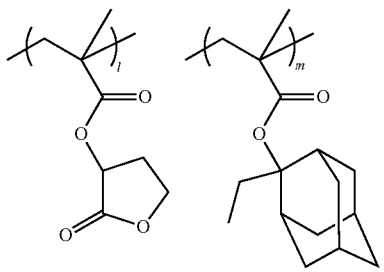
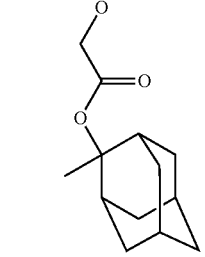
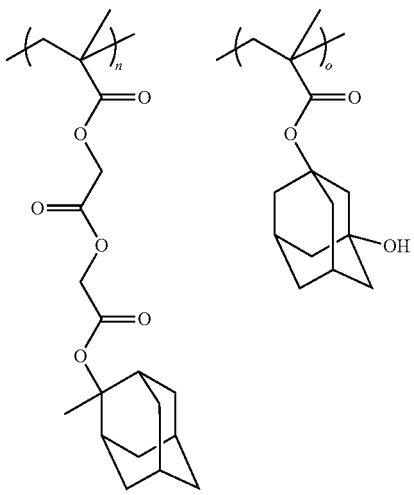

Polymer Compound (1)

Examples 1 to 2, Comparative Example 1

The components shown in Table 1 below were mixed together and dissolved to obtain positive resist composition solutions.

TABLE 1

| | Component (A) | Component (B) | | Component (D) | Component (S) |
|---|---|---|---|---|---|
| Example 1 | (A)-1 [100] | (B)-1 [3.96] | (B)-2 [8.25] | (D)-1 [0.23] | (S)-1 [2,500] |
| Example 2 | (A)-1 [100] | (B)-1 [16.00] | — | (D)-1 [0.23] | (S)-1 [2,500] |
| Comparative Example 1 | (A)-1 [100] | — | (B)-2 [11.00] | (D)-1 [0.23] | (S)-1 [2,500] |

The meanings of the abbreviations used in Table 1 are as shown below. The numerical values within the brackets [ ] represent blend quantities (parts by weight).
(A)-1: the aforementioned polymer compound (1).
(B)-1: the aforementioned compound (3-1).
(B)-2: the aforementioned compound (4-2).
(D)-1: diethanolamine.
(S)-1: a mixed solvent of PGMEA/PGME = 6/4 (weight ratio).

<Formation of a Resist Pattern by Immersion Exposure>

An organic anti-reflection film composition (product name: ARC29A, manufactured by Brewer Science Ltd.) was applied onto a 12-inch silicon wafer using a spinner, and the composition was then baked and dried on a hotplate at 205° C. for 60 seconds, thereby forming an organic anti-reflection film having a film thickness of 85 nm.

Then, each of the resist composition solutions obtained above was applied onto the anti-reflection film using a spinner, and was then prebaked (PAB) on a hotplate at 100° C. for 60 seconds, thereby forming a resist film having a film thickness of 120 nm.

Subsequently, the resist film was selectively irradiated with an ArF excimer laser (193 nm) through a mask pattern (6% half tone mask), using an ArF exposure apparatus NSR-S308F (manufactured by Nikon Corporation, NA (numerical aperture)=0.92).

Thereafter, a post exposure bake (PEB) treatment was conducted at 95° C. for 60 seconds, followed by development for 30 seconds at 23° C. in a 2.38% by weight aqueous solution of tetramethylammonium hydroxide (TMAH). Then, the resist film was washed for 30 seconds with pure water, followed by drying by shaking.

As a result, in each of the examples, a contact hole pattern (hereafter, referred to as "CH pattern") in which holes with a hole diameter of 110 nm were positioned with equal spacing (pitch: 240 nm) was formed on the resist film.

Each of the formed CH patterns was observed from above using a scanning electron microscope (SEM). As a result, in the CH pattern formed using the resist composition of Comparative Example 1, the presence of numerous holes having diameters smaller than the target size (i.e., 110 nm) was observed. On the other hand, in the CH patterns formed using the resist compositions of Examples 1 and 2, the diameter of each hole was, on the whole, uniform.

<Evaluation of Defects>

Subsequently, a surface defect inspection device KLA2371 (a product name) manufactured by KLA Tencor Corporation was used to observe the surface of the above-mentioned resist pattern, thereby measuring the number of "Not Open" defects thereon. As a result, it was found that the number of "Not Open" defects in the resist pattern of Comparative Example 1 was 508. On the other hand, the number of "Not Open" defects in the resist pattern of Example 1 was 118, and the number of "Not Open" defects in the resist pattern of Example 2 was 48. Thus, the number of "Not Open" defects in these examples was considerably less than that in Comparative Example 1.

From the results shown above, it was confirmed that the compound according to the present invention is useful as an acid generator to be used in a resist composition. Further, the resist composition containing the compound of the present invention as an acid generator was capable of forming an excellent resist pattern with minimal defects in immersion exposure.

Synthesis Example 7

Synthesis of Compound A 3.63 g of 2,6-dimethylphenol and 72.65 g of acetone were charged into a three-necked flask, and 12.34 g of potassium carbonate was then added thereto. The resultant was stirred for 30 minutes, and 23.22 g of 4,4,5,5,6,6,7,7,7-nonafluoroheptyl iodide was then added thereto, and a reaction was effected at 40° C. for 19 hours. The reaction solution was cooled to room temperature and was filtered, and the resulting filtrate was solidified. 11.37 g of TBME was then added to the obtained solid, and the resultant was washed four times with 11.37 g of pure water. The resultant was then subjected to liquid separation to collect the organic phase, and the obtained organic phase was concentrated, and was then purified by distillation, thereby obtaining 8.88 g of a compound A.

The compound A was analyzed by NMR.

$^1$H-NMR (DMSO-d6, 400 MHz): δ (ppm)=2.03-2.10 (m, 2H, H$^b$), 2.23 (m, 6H, H$^d$), 2.43-2.55 (m, 2H, H$^a$), 3.85 (t, 2H, H$^c$), 6.91-7.03 (m, 3H, H$^e$).

$^{19}$F-NMR (DMSO-d6, 376 MHz): δ (ppm)=−123.5, −121.8, −111.6, −78.3.

From the results shown above, it was confirmed that the compound A had a structure shown below.

[Chemical Formula 72]

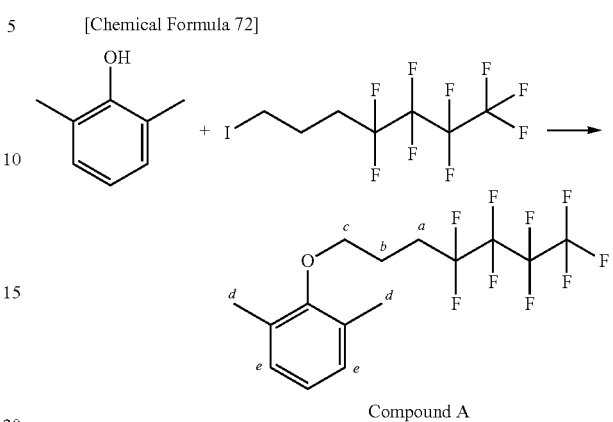

Compound A

Synthesis Example 8

Synthesis of Compound B 2.64 g of diphosphorus pentaoxide was added to 38.4 g of methanesulfonic acid while stirring, and 8.55 g of the compound A represented by the above structural formula and 1.88 g of diphenylsulfoxide were then added gradually thereto while cooling with ice. Thereafter, the resultant was stirred for 24 hours at room temperature, and the obtained reaction solution was then gradually added dropwise to a mixed solvent of 91.3 g of pure water and 152.1 g of TBME. Then, liquid separation was conducted to obtain a water phase. The obtained water phase was washed twice with 91.3 g of TBME, and was then extracted twice with 91.3 g of dichloromethane, and the obtained dichloromethane phase was concentrated to thereby obtain 7.4 g of a compound B in the form of a viscous solid.

The compound B was analyzed by NMR.

$^1$H-NMR (DMSO-d6, 400 MHz): δ (ppm)=2.03-2.56 (m, 13H, H$^a$+H$^b$+H$^d$+H$^e$), 3.97 (t, 2H, H$^c$), 7.62 (s, 2H, Ar), 7.75-7.87 (m, 10H, Ar).

$^{19}$F-NMR (DMSO-d6, 376 MHz): δ (ppm)=−123.5, −121.8, −111.6, −78.3.

From the results shown above, it was confirmed that the compound B had the structure shown below.

[Chemical Formula 73]

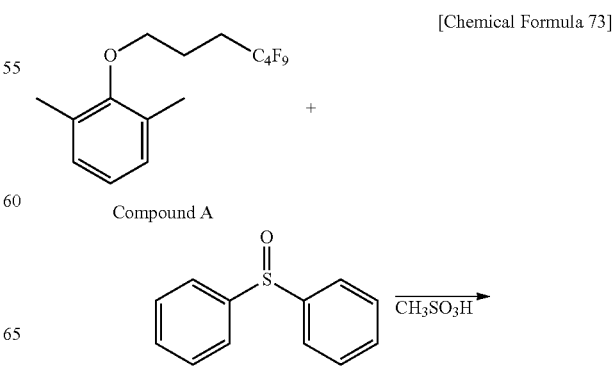

Compound A

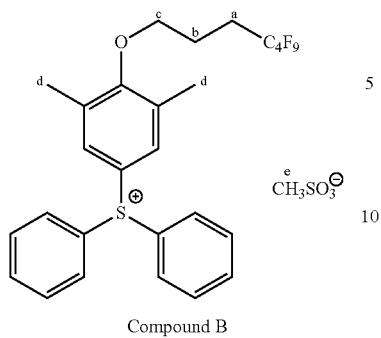

Compound B

Synthesis Example 9

Synthesis of Compound C 20.2 g of pure water and 20.2 g of dichloromethane were added to 5.00 g of the compound B having the above-mentioned structure, and 4.30 g of a compound (9-1) was then added thereto, and the resultant was stirred at room temperature for 3 hours. Thereafter, the resultant was subjected to liquid separation to collect a dichloromethane phase, and the obtained dichloromethane phase was washed twice with 20.2 g of diluted hydrochloric acid, and was then washed four times with 20.2 g of pure water. The resulting dichloromethane phase was concentrated and solidified, thereby obtaining 5.68 g of a compound C in the form of a white solid.

The compound C was analyzed by NMR.

$^1$H-NMR (DMSO-d6, 400 MHz): δ (ppm)=1.60-1.91 (m, 15H, adamantane), 2.03-2.56 (m, 10H, $H^a$+$H^b$+$H^d$), 3.97 (t, 2H, $H^c$), 4.59 (t, 2H, $H^e$), 7.60 (s, 2H, Ar), 7.75-7.84 (m, 10H, Ar).

$^{19}$F-NMR (DMSO-d6, 376 MHz): δ (ppm)=−123.5, −121.8, −111.6, −111.2, −78.3.

From the results shown above, it was confirmed that the compound C had the structure shown below.

[Chemical Formula 74]

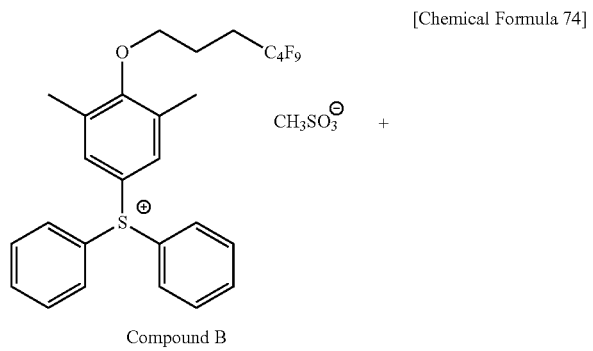

Synthesis Example 10

Synthesis of Compound D 8.82 g of pure water and 8.82 g of dichloromethane were added to 2.09 g of the compound B represented by a structural formula shown below, and 1.27 g of a compound (10-1) represented by a structural formula shown below was then added thereto, and the resultant was stirred at room temperature for 3 hours. Thereafter, the resultant was subjected to liquid separation to collect a dichloromethane phase, and the obtained dichloromethane phase was washed twice with 8.82 g of diluted hydrochloric acid, and was then washed four times with 8.82 g of pure water. The resulting dichloromethane phase was concentrated and solidified, thereby obtaining 2.02 g of a compound D in the form of a white solid.

The compound D was analyzed by NMR.

$^1$H-NMR (DMSO-d6, 400 MHz): δ (ppm)=1.60-1.91 (m, 15H, adamantane), 2.03-2.56 (m, 10H, $H^a$+$H^b$+$H^d$), 3.97 (t, 2H, $H^c$), 4.20 (t, 2H, $H^e$), 4.41 (t, 2H, $H^f$), 7.59 (s, 2H, Ar), 7.71-7.89 (m, 10H, Ar).

$^{19}$F-NMR (DMSO-d6, 376 MHz): δ (ppm)=−123.1, −121.4, −111.0, −106.7, −77.9.

From the results shown above, it was confirmed that the compound D had the structure shown below.

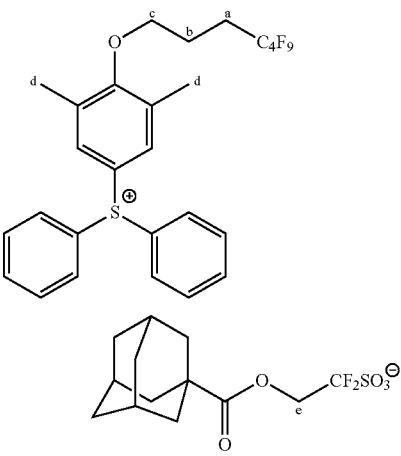

Compound C

[Chemical Formula 75]

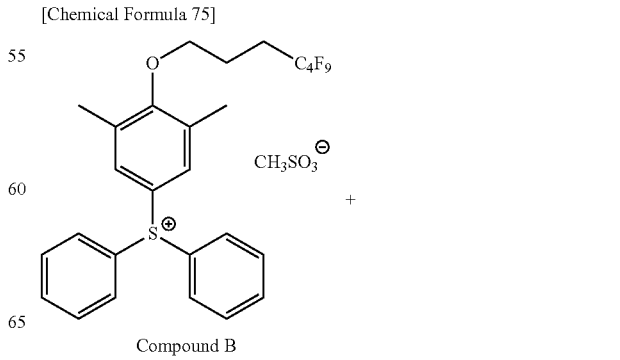

Compound B

-continued

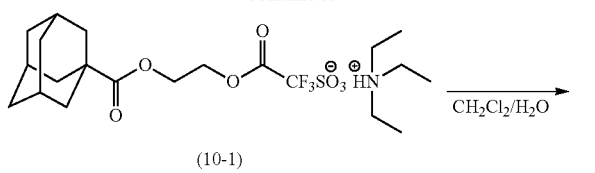

(10-1)

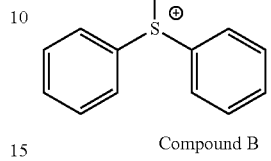

Compound B

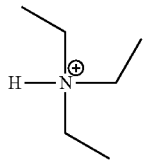

Compound D

Synthesis Example 11

Synthesis of Compound E 2 g of the compound B represented by a structural formula shown below was added to 20 g of dichloromethane and 20 g of water, and the resultant was stirred. Then, 1.83 g of a compound ($M^+X^-$) shown below was added thereto, and the resultant was stirred for 1 hour. The reaction solution was subjected to liquid separation to collect an organic solvent phase, and the obtained organic solvent phase was washed four times with 20 g of water, and was then concentrated and solidified, thereby obtaining 2.0 g of a compound E.

The compound E was analyzed by NMR.

$^1$H-NMR (DMSO-d6, 400 MHz): δ (ppm)=0.79-2.89 (m, 31H, $H^a$+$H^b$+$H^d$+Undecanoyl), 3.97 (t, 2H, $H^c$), 4.23 (t, 2H, CH$_2$), 4.41 (t, 2H, CH$_2$), 7.59 (s, 2H, Ar), 7.71-7.89 (m, 10H, Ar).

$^{19}$F-NMR (DMSO-d6, 376 MHz): δ (ppm)=−123.1, −121.4, −111.0, −106.8, −77.9.

From the results shown above, it was confirmed that the compound E had the structure shown below.

[Chemical Formula 76]

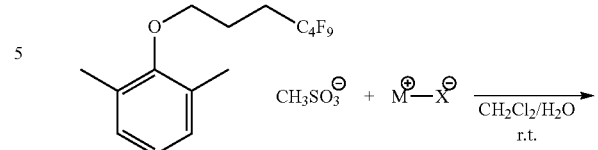

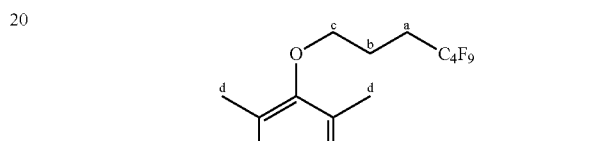

Compound E $M^+X^-$ =

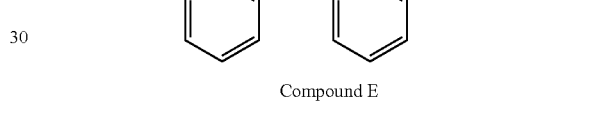

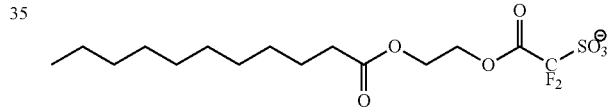

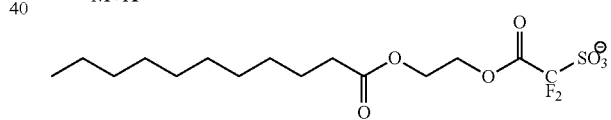

Synthesis Examples 12 to 29

Synthesis of Compounds F to W

Products (namely, compounds F to W) composed of anions and cations shown in Tables 2 to 6 were obtained by conducting the same operations as those described in the above Synthesis Example 11 except that the compound ($M^+X^-$) was changed to those shown in the following Tables 2 to 6 (shown in molar equivalent amounts). Each of the compounds was analyzed by NMR. The results are shown in Tables 2 to 6. In Tables 2 to 6, the symbol "↑" indicates that the cation in the compounds G to W is the same as the cation in the compound F.

TABLE 2

| Compound | Compound M⁺X⁻ | NMR | Product Cation | Product Anion |
|---|---|---|---|---|
| F | [structure: pentafluorophenoxy ethyl ester of sulfonate, Na⁺] | ¹H - NMR (DMSO-d6, 400 MHz): δ (ppm) = 2.03-2.56 (m, 10H, Ha + Hb + Hd), 3.97 (t, 2H, Hc), 4.40-4.50 (m, 4H, CH2), 7.59 (s, 2H, Ar), 7.71-7.89 (m, 10H, Ar) ¹⁹F - NMR (DMSO-d6, 376 MHz): δ (ppm) = −161.5, −160.0, −154.0, −123.1, −121.4, −111.0, −106.7, −77.9 | [structure: C4F9-substituted phenoxy-alkyl triphenylsulfonium cation with labels a, b, c, d] | [structure: pentafluorophenoxy ethyl ester of sulfonate anion] |
| G | [structure: norbornane sultone ester of sulfonate, Na⁺] | ¹H - NMR (DMSO-d6, 400 MHz): δ (ppm) = 1.73-2.56 (m, 14H, Ha + Hb + Hd + CH2), 2.49 (m, 1H, CH), 3.34 (m, 1H, CH), 3.88 (t, 1H, CH), 3.97 (t, 2H, Hc), 4.66 (t, 1H, CH), 4.78 (m, 1H, CH), 7.59 (s, 2H, Ar), 7.71-7.89 (m, 10H, Ar) ¹⁹F - NMR (DMSO-d6, 376 MHz): δ (ppm) = −123.1, −121.4, −111.0, −107.7, −77.9 | ← | [structure: norbornane sultone ester anion] |
| H | [structure: pyridine-4-carboxylate ethyl ester of sulfonate, triethylammonium] | ¹H - NMR (DMSO-d6, 400 MHz): δ (ppm) = 2.03-2.56 (m, 10H, Ha + Hb + Hd), 3.97 (t, 2H, Hc), 4.54-4.61 (m, 4H, CH2CH2), 7.59 (s, 2H, Ar), 7.71-7.89 (m, 12H, Ar + Py-H), 8.74-8.82 (m, 2H, Py-H) ¹⁹F - NMR (DMSO-d6, 376 MHz): δ (ppm) = −123.1, −121.4, −111.0, −106.5, −77.9 | ← | [structure: isonicotinate ethyl ester anion] |

TABLE 3
| Compound | NMR | Compound M⁺X⁻ | Product Cation | Product Anion |
|---|---|---|---|---|
| I | ¹H - NMR (DMSO-d6, 400 MHz): δ (ppm) = 2.03-2.56 (m, 12H, Ha + Hb + Hd + ONL), 2.69-2.73 (m, 1H, ONL), 3.97 (t, 2H, Hc), 4.57 (d, 1H, ONL), 4.71 (d, 1H, ONL), 4.97 (s, 1H, ONL), 5.46 (t, 1H, ONL), 7.59 (s, 2H, Ar), 7.71-7.89 (m, 10H, Ar) ¹⁹F - NMR (DMSO-d6, 376 MHz): δ (ppm) = −123.1, −121.4, −111.0, −107.1, −77.9 | 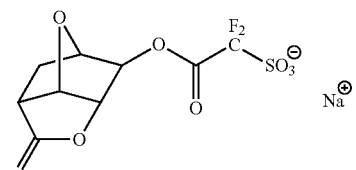 | ↑ | 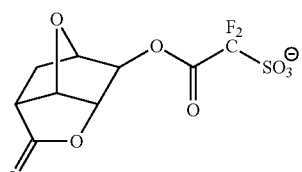 |
| J | ¹H - NMR (DMSO-d6, 400 MHz): δ (ppm) = 1.53-1.95 (m, 15H, adamantane), 2.03-2.56 (m, 12H, Ha + Hb + Hd + CH2), 3.97 (t, 2H, Hc), 4.20 (t, 2H, CH2), 4.40 (t, 2H, CH2), 7.59 (s, 2H, Ar), 7.71-7.89 (m, 10H, Ar) ¹⁹F - NMR (DMSO-d6, 376 MHz): δ (ppm) = −123.1, −121.4, −111.2, −111.0, −77.9 | 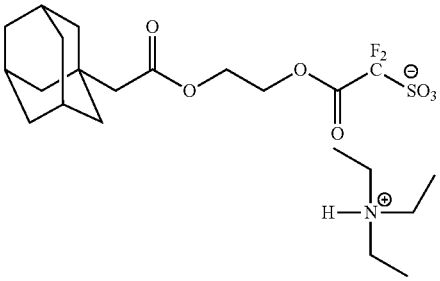 | ↑ | 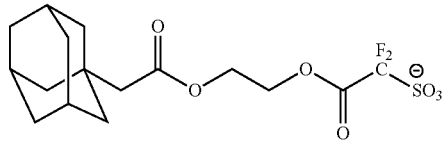 |

TABLE 3-continued

| Compound | NMR | Compound M+ X− | Product Cation | Product Anion |
|---|---|---|---|---|
| K | ¹H - NMR (DMSO-d6, 400 MHz): δ (ppm) = 1.07-1.33 (m, 5H, Cyclohexyl), 1.56-1.59 (m, 1H, Cyclohexyl), 1.73-1.75 (m, 2H, Cyclohexyl), 2.03-2.56 (m, 12H, Ha + Hb + Hd + Cyclohexyl), 2.77-2.81 (m, 1H, Cyclohexyl), 3.97 (t, 2H, Hc), 7.59 (s, 2H, Ar), 7.71-7.89 (m, 10H, Ar) ¹⁹F- NMR (DMSO-d6, 376 MHz): δ (ppm) = −123.1, −121.4, −111.2, −111.0, −77.9, −74.7 | 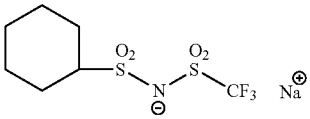 [SMILES: O=S(=O)([N-]S(=O)(=O)C(F)(F)F)C1CCCCC1 ; [Na+]] | ↑ | 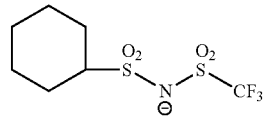 |

TABLE 4

| Compound | NMR | Compound M+ X− | Product Cation | Product Anion |
|---|---|---|---|---|
| L | ¹H - NMR (DMSO-d6, 400 MHz): δ (ppm) = 1.55-1.88 (m, 15H, adamantane), 2.03-2.56 (m, 10H, Ha + Hb + Hd), 3.97 (t, 2H, Hc), 7.59 (s, 2H, Ar), 7.71-7.89 (m, 10H, Ar) ¹⁹F - NMR (DMSO-d6, 376 MHz): δ (ppm) = −123.1, −121.4, −111.2, −111.0, −77.9, −74.5 | 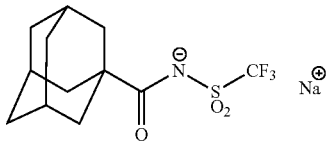 [SMILES: O=C([N-]S(=O)(=O)C(F)(F)F)C12CC3CC(CC(C3)C1)C2 ; [Na+]] | ↑ | 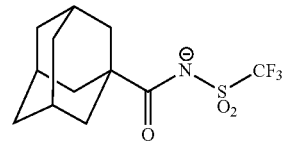 [SMILES: O=C([N-]S(=O)(=O)C(F)(F)F)C12CC3CC(CC(C3)C1)C2] |
| M | ¹H - NMR (DMSO-d6, 400 MHz): δ (ppm) = 1.59 (s, 6H, adamantane), 1.99 (m, 6H, adamantane), 2.03-2.56 (m, 13H, Ha + Hb + Hd + adamantane), 3.97 (t, 2H, Hc), 7.59 (s, 2H, Ar), 7.71-7.89 (m, 10H, Ar) ¹⁹F - NMR (DMSO-d6, 376 MHz): δ (ppm) = −123.1, −121.4, −112.9, −111.0, −77.9, −76.0, −69.2 | 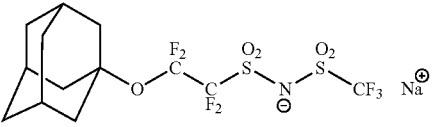 [SMILES: O=S(=O)([N-]S(=O)(=O)C(F)(F)C(F)(F)OC12CC3CC(CC(C3)C1)C2)C(F)(F)F ; [Na+]] | ↑ | 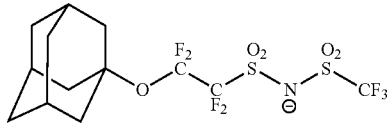 [SMILES: O=S(=O)([N-]S(=O)(=O)C(F)(F)C(F)(F)OC12CC3CC(CC(C3)C1)C2)C(F)(F)F] |

TABLE 4-continued

| Compound | NMR | Compound M⁺ X⁻ | Product Cation | Product Anion |
|---|---|---|---|---|
| N | ¹H - NMR (DMSO-d6, 400 MHz): δ (ppm) = 2.03-2.56 (m, 10H, Ha + Hb + Hd), 3.97 (t, 2H, Hc), 5.20 (s, 2H, CH2), 7.51-7.96 (m, 19H, Ar+ Naph) ¹⁹F - NMR (DMSO-d6, 376 MHz): δ (ppm) = −123.1, −121.4, −113.7, −111.0, −80.5, −77.9 | Naphthyl-CH2-O-CF2-CF2-SO3⁻ Li⁺ | ↑ | Naphthyl-CH2-O-CF2-CF2-SO3⁻ |
| O | ¹H - NMR (DMSO-d6, 400 MHz): δ (ppm) = 1.56 (s, 6H, adamantane), 1.96 (s, 6H, adamantane), 2.03-2.56 (m, 13H, Ha + Hb + Hd + adamantane), 3.97 (t, 2H, Hc), 7.59 (s, 2H, Ar), 7.71-7.89 (m, 10H, Ar) ¹⁹F - NMR (DMSO-d6, 376 MHz): δ (ppm) = −123.1, −121.4, −113.36, −111.0, −77.9, −70.13 | Adamantyl-O-CF2-CF2-SO3⁻ Li⁺ | ↑ | Adamantyl-O-CF2-CF2-SO3⁻ |

TABLE 5

| Compound | NMR | Compound M⁺ X⁻ | Product Cation | Product Anion |
|---|---|---|---|---|
| P | ¹H - NMR (DMSO-d6, 400 MHz): δ (ppm) = 2.03-2.56 (m, 10H, Ha + Hb + Hd), 3.97 (t, 2H, Hc), 7.59 (s, 2H, Ar), 7.71-7.89 (m, 10H, Ar) ¹⁹F - NMR (DMSO-d6, 376 MHz): δ (ppm) = −123.1, −121.4, −111.2, −111.0, −77.9, −73.68 | (F3C-SO2)(F3C-O2S)C⁻(SO2-CF3) H⁺ | ↑ | (F3C-SO2)(F3C-O2S)C⁻(SO2-CF3) |
| Q | ¹H - NMR (DMSO-d6, 400 MHz): δ (ppm) = 2.03-2.56 (m, 10H, Ha + Hb + Hd), 3.97 (t, 2H, Hc), 7.59 (s, 2H, Ar), 7.71-7.89 (m, 10H, Ar) ¹⁹F - NMR (DMSO-d6, 376 MHz): δ (ppm) = −161.1, −149.7, −131.6, −123.1, −121.4, −111.0, −77.9, −76.2 | Pentafluorophenyl-C⁻(SO2-CF3)2, H⁺ | ↑ | Pentafluorophenyl-C⁻(SO2-CF3)2 |
| R | ¹H - NMR (DMSO-d6, 400MHz): δ (ppm) = 0.71 (s, 3H, CH3), 1.03 (s, 3H, CH3), 1.22-1.29 (m, 2H, CH2), 1.74-1.89 (m, 2H, CH2), 1.90 (t, 1H, CH), 2.03-2.56 (m, 12H, Ha + Hb + Hd + CH), 2.66-2.74 (m, 1H, CH), 2.88 (d, 1H, CH), 3.97 (t, 2H, Hc), 7.59 (s, 2H, Ar), 7.71-7.89 (m, 10H, Ar) ¹⁹F - NMR (DMSO-d6, 376 MHz): δ (ppm) = −123.1, −121.4, −111.0, −77.9 | Camphorsulfonate Na⁺ | ↑ | Camphorsulfonate |

TABLE 5-continued

| Compound | NMR | Compound M+ X− | Product Cation | Product Anion |
|---|---|---|---|---|
| S | $^1$H - NMR (DMSO-d6, 400 MHz): δ (ppm) = 2.03-2.56 (m, 10H, Ha + Hb + Hd), 3.97 (t, 2H, Hc), 7.59 (s, 2H, Ar), 7.71-7.89 (m, 10H, Ar) $^{19}$F - NMR (DMSO-d6, 376 MHz): δ (ppm) = −123.1, −121.4, −111.0, −77.9, −75.0 | CF$_3$SO$_3^\ominus$ K$^\oplus$ | ↑ | CF$_3$SO$_3^\ominus$ |

TABLE 6

| Compound | NMR | Compound M+ X− | Product Cation | Product Anion |
|---|---|---|---|---|
| T | $^1$H - NMR (DMSO-d6, 400 MHz): δ (ppm) = 2.03-2.56 (m, 10H, Ha + Hb + Hd), 3.97 (t, 2H, Hc), 7.59 (s, 2H, Ar), 7.71-7.89 (m, 10H, Ar) $^{19}$F - NMR (DMSO-d6, 376 MHz): δ (ppm) = −123.1, −121.7, −121.4, −112.5, −111.0, −77.9, −77.3 | C$_3$F$_7$SO$_3^\ominus$ K$^\oplus$ | ↑ | C$_3$F$_7$SO$_3^\ominus$ |
| U | $^1$H - NMR (DMSO-d6, 400 MHz): δ (ppm) = 2.03-2.56 (m, 10H, Ha + Hb + Hd), 3.97 (t, 2H, Hc), 7.59 (s, 2H, Ar), 7.71-7.89 (m, 10H, Ar) $^{19}$F - NMR (DMSO-d6, 376 MHz): δ (ppm) = −123.1, −123.0, −121.4, −116.9, −111.0, −77.9 | (cyclic sulfonylimide anion) K$^\oplus$ | ↑ | (cyclic sulfonylimide anion) |
| V | $^1$H - NMR (DMSO-d6, 400 MHz): δ (ppm) = 2.03-2.56 (m, 10H, Ha + Hb + Hd), 3.97 (t, 2H, Hc), 7.59 (s, 2H, Ar), 7.71-7.89 (m, 10H, Ar) $^{19}$F - NMR (DMSO-d6, 376 MHz): δ (ppm) = −123.1, −121.4, −114.7, −111.0, −77.9, −76.0, −75.9 | F$_3$CF$_2$C−S(O$_2$)−N$^\ominus$−S(O$_2$)−CF$_3$ K$^\oplus$ | ↑ | F$_3$CF$_2$C−S(O$_2$)−N$^\ominus$−S(O$_2$)−CF$_3$ |
| W | $^1$H - NMR (DMSO-d6, 400 MHz): δ (ppm) = 2.03-2.56 (m, 10H, Ha + Hb + Hd), 3.97 (t, 2H, Hc), 4.45 (s, 2H, anion CH2), 5.21 (dd, 1H, anion CH), 5.41 (dd, 1H, anion CH), 5.83-5.92 (m, 1H, anion CH), 7.59 (s, 2H, Ar), 7.71-7.89 (m, 10H, Ar) $^{19}$F - NMR (DMSO-d6, 376 MHz): δ (ppm) = −123.1, −121.4, −113.0, −111.0, −80.0, −77.9 | allyl-O-CF$_2$-CF$_2$-SO$_3^\ominus$ Li$^\oplus$ | ↑ | allyl-O-CF$_2$-CF$_2$-SO$_3^\ominus$ |

Synthesis Example 30

Synthesis of [Compound 5] (Monomer)

(i)
78.1 g (500 mmol) of 5,6-dihydroxy-7-oxanorbornane-2-carboxylic acid γ-lactone, 43.5 g (550 mmol) of pyridine, and 250 g of tetrahydrofuran (THF) were charged into a reaction vessel, and 79.1 g (700 mmol) of chloroacetyl chloride was then dropwise added thereto at 30° C. or less using a dropping funnel. The resulting reaction solution was stirred at 25° C. for 18 hours, and ethyl acetate was then added thereto. Subsequently, the resultant was neutralized by adding 10% by weight aqueous solution of potassium carbonate thereto, and the precipitated crystals were collected by filtration, followed by washing with water. The obtained crystals were dried, thereby obtaining 85.8 g (369 mmol) of 5-chloroacetoxy-6-hydroxy-7-oxanorbornane-2-carboxylic acid γ-lactone (compound (30-1)) (yield: 73.8%).

The obtained compound (30-1) was analyzed by $^1$H-NMR. The results are shown below.

$^1$H-NMR (270 MHz, CDCl$_3$, ppm, TMS) δ: 5.39 (1H, t, J=5.0 Hz), 4.82 (1H, s), 4.75 (1H, d, J=5.5 Hz), 4.69 (1H, d, J=5.0 Hz), 4.12 (2H, s), 2.77 (1H, d, J=1.8, 4.8, 5.5 Hz), 2.30 (1H, m), 2.10 (1H, m).

From the results shown above, it was confirmed that the obtained compound (30-1) had the structure shown below.

[Chemical Formula 77]

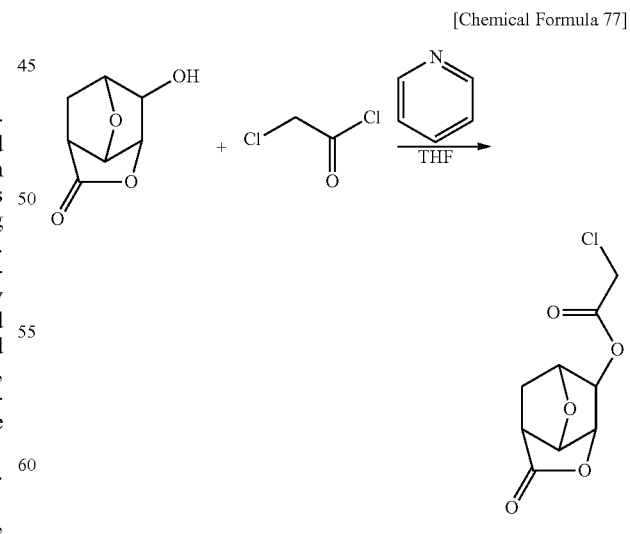

(30-1)

(ii)
Then, 40.7 g (472.9 mmol) of methacrylic acid, 89.1 g (644.9 mmol) of potassium carbonate, and 400 g of dimethylformamide (DMF) were charged into a 5 L four-necked flask equipped with a dropping funnel, a thermometer, and a stirrer. Subsequently, a solution formed of 100.0 g (429.9 mmol) of the compound (30-1) having the above-mentioned structure and 650 g DMF was dropwise added thereto at room temperature using the dropping funnel. 28.6 g (172.0 mmol) of potassium iodide was added to the reaction liquid, and the resultant was then stirred at room temperature for 5 hours. Thereafter, ethyl acetate and water were added to a flask (namely, the reaction vessel), and the resulting reaction mixture was then transferred to a separatory funnel and the obtained water phase was discarded. The obtained organic phase was washed with water, and was then dried and concentrated using magnesium sulfate, thereby obtaining 99.9 g (353.8 mmol) of 5-(2'-methacyloyloxyacetoxy-6-hydroxy-7-oxanorbornane-2-carboxylic acid γ-lactone ([compound 5]) (yield: 82.3%).

The obtained [compound 5] was analyzed by $^1$H-NMR. The results are shown below.

$^1$H-NMR (270 MHz, CDCl$_3$, ppm, TMS) δ: 6.23 (1H, s), 5.69 (1H, s), 5.39 (1H, t, J=5.0 Hz), 4.82 (1H, s), 4.75 (1H, d, J=5.5 Hz), 4.69 (1H, d, J=5.0 Hz), 4.12 (2H, s), 2.77 (1H, d, J=1.8, 4.8, 5.5 Hz), 2.30 (1H, m), 2.10 (1H, m), 1.90 (3H, s).

From the results shown above, it was confirmed that the obtained [compound 5] had a structure shown below.

[Chemical Formula 78]

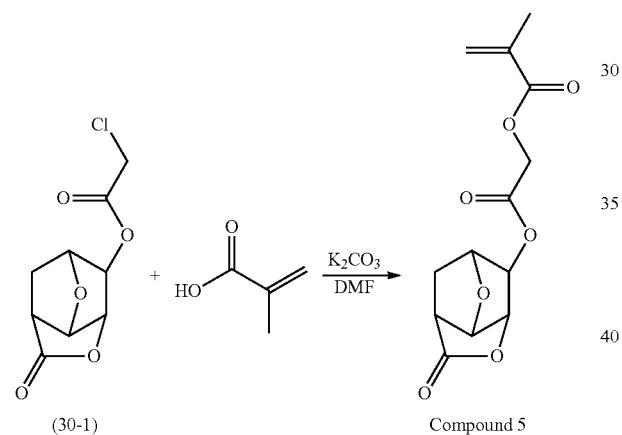

(30-1)  Compound 5

Synthesis Example 31

Synthesis of Polymer Compound (2)

The [compound 5] having the above-mentioned structure, and the [compound 1], [compound 6], [compound 7] and [compound 4] having the following structures were added to and dissolved in dimethylformamide (DMF) in amounts based on the proportions of each of the structural units within an objective polymer compound. Then, dimethyl azobisisobutyrate as a polymerization initiator was added to and dissolved in the resulting solution. The obtained reaction solution was stirred while being heated at 80° C. for 6 hours in a nitrogen atmosphere, and was then cooled to room temperature. Thereafter, the resulting polymerization solution was dropwise added to an excess amount of mixed solution of methanol/water to thereby precipitate a polymer. Then, the precipitated polymer compound was separated by filtration, followed by washing and drying, thereby obtaining a polymer compound (2) as an objective compound.

The obtained polymer compound (2) was subjected to GPC measurement. As a result, it was found that the weight average molecular weight (Mw) was 7,000, and the dispersity (Mw/Mn) was 1.7. Further, the polymer compound (2) was analyzed by carbon 13 nuclear magnetic resonance spectroscopy (600 MHz, $^{13}$C-NMR). As a result, it was found that the polymer composition thereof (namely, ratio (molar ratio) of the respective structural units within the structural formula shown below) was a1/a2/a3/a4/a5=28/35.5/15/13.5/8.

[Chemical Formula 79]

Compound 1

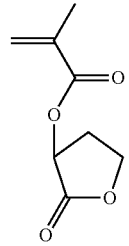

Compound 6

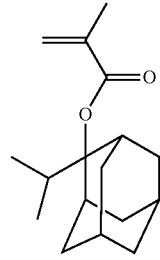

Compound 7

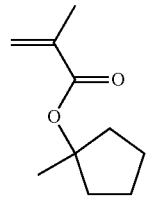

Compound 4

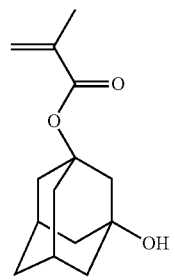

Polymer Compound (2)

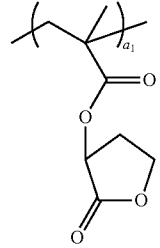

-continued

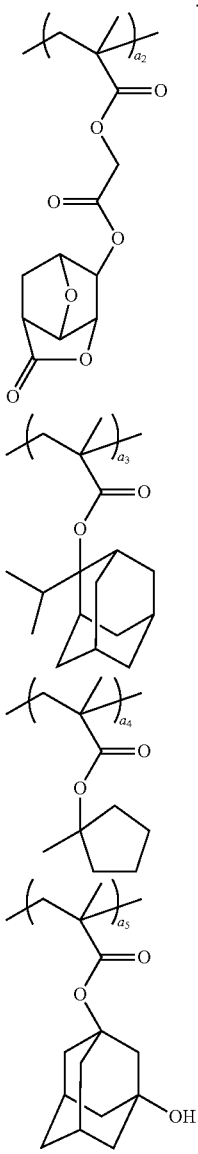

Example 3, Comparative Example 2

The components shown in Table 7 below were mixed together and dissolved to obtain positive resist composition solutions.

TABLE 7

| | Component (A) | Component (B) | | Component (D) | Component (S) |
|---|---|---|---|---|---|
| Example 3 | (A)-2 [100] | (B)-3 [7.5] | (B)-4 [2.5] | (D)-2 [0.4] | (S)-1 [2,700] |
| Comparative Example 2 | (A)-2 [100] | (B)-3 [9.8] | — | (D)-2 [0.4] | (S)-1 [2,700] |

The meanings of the abbreviations used in Table 7 are as shown below. The numerical values within the brackets [ ] represent blend quantities (parts by weight).
(A)-2: the aforementioned polymer compound (2).
(B)-3: a compound represented by chemical formula (B)-3 shown below.
(B)-4: a compound represented by chemical formula (B)-4 shown below (the aforementioned compound C).
(D)-2: tri-n-pentylamine.
(S)-1: a mixed solvent of PGMEA/PGME=6/4 (weight ratio).

(Chemical Formula 80]

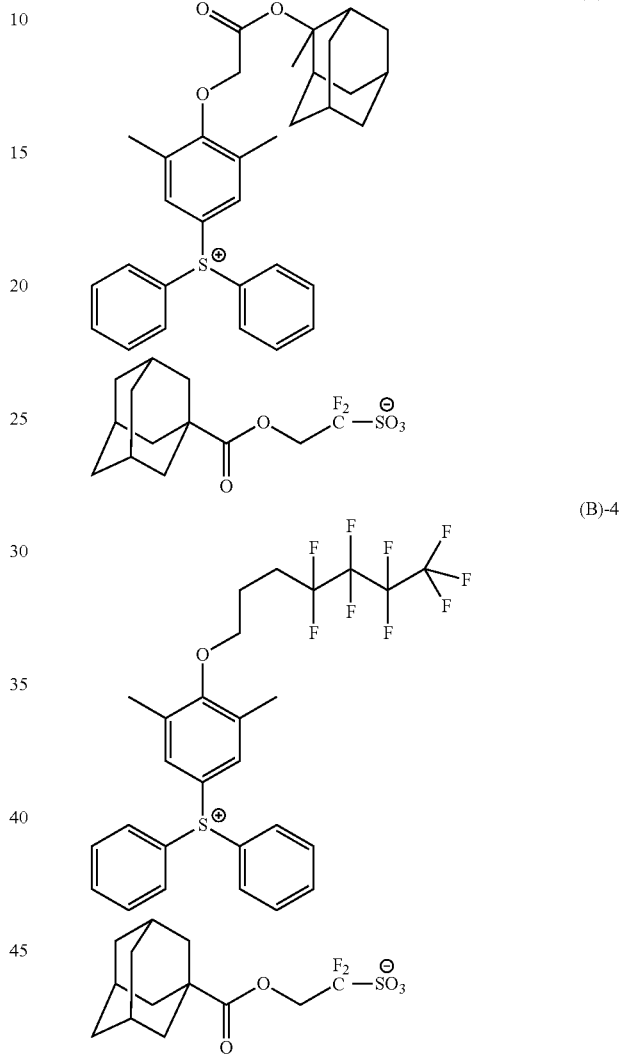

<Evaluation of Lithographic Properties>
By using the obtained resist compositions, resist patterns were formed in the following manner, and lithographic properties thereof were evaluated.
[Formation of a Resist Pattern]
An organic anti-reflection film composition (product name: ARC29A, manufactured by Brewer Science Ltd.) was applied onto an 12-inch silicon wafer using a spinner, and the composition was then baked and dried on a hotplate at 205° C. for 60 seconds, thereby forming an organic anti-reflection film having a film thickness of 89 nm. Then, each of the resist composition solutions obtained above was applied onto the anti-reflection film using a spinner, and was then prebaked (PAB) on a hotplate at 90° C. for 60 seconds and dried, thereby forming a resist film having a film thickness of 100 nm.
Subsequently, a coating solution for forming a protection film (product name: TILC-057; manufactured by Tokyo Ohka Kogyo Co., Ltd.) was applied onto the resist film using a spinner, and then heated at 90° C. for 60 seconds, thereby forming a top coat with a film thickness of 35 nm.

Thereafter, using an ArF exposure apparatus for immersion lithography (product name: NSR-S609B, manufactured by Nikon Corporation, NA (numerical aperture)=1.07, σ Conventional (0.97) w/o POLANO), the resist film having a top coat formed thereon was selectively irradiated with an ArF excimer laser (193 nm) through a mask pattern.

Next, a post exposure bake (PEB) treatment was conducted at 85° C. for 60 seconds, followed by development for 35 seconds at 23° C. in a 2.38% by weight aqueous solution of tetramethylammonium hydroxide (TMAH solution manufactured by Tokyo Ohka Kogyo Co., Ltd.). Then, the resist film was rinsed for 15 seconds with pure water, followed by drying by shaking.

As a result, in each of the examples, a dense, contact hole pattern (hereafter, referred to as "CH pattern") with a hole diameter of 90 nm and a pitch of 140 nm was formed on the resist film.

Further, the sensitivity during formation of the above CH pattern was used as the optimum exposure dose (Eop, mJ/cm$^2$) value.

Eop values for each of the positive resist compositions are shown in Table 8.

Furthermore, with the above-mentioned Eop, formation of a sparse (isolated) CH pattern with a hole diameter of 90 nm and a pitch of 540 nm was also conducted.

[Evaluation of Depth of Focus (DOF)]

With the above-mentioned Eop, by shifting the focus up and down where appropriate, the depth of focus (DOF; unit: μm) was determined within the range where each of the above-mentioned isolated/dense CH patterns was formed with a successful resolution. The results are shown in Table 8.

[Evaluation of in-Plane Uniformity (CDU)]

With respect to each of the formed dense/isolated CH patterns, the contact-hole diameter (CD) was measured for 25 holes within the same wafer, and from the results, the value of 3 times the standard deviation σ (i.e., 3σ) was calculated as a yardstick of CD uniformity (CDU). The smaller this 3σ value is, the higher the level of CDU (i.e., the in-plane uniformity of contact-hole diameter) of the holes formed in the resist film. The results are shown in Table 8.

TABLE 8

| | | DOF (nm) | | CDU (3σ) | |
|---|---|---|---|---|---|
| | Eop (mJ/cm$^2$) | Dense CH | Isolated CH | Dense CH | Isolated CH |
| Example 3 | 34.2 | 360 | 300 | 4.55 | 5.33 |
| Comparative Example 2 | 44.4 | 360 | 240 | 6.19 | 5.40 |

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

INDUSTRIAL APPLICABILITY

The present invention is able to provide a novel compound useful as an acid generator for a resist composition, an acid generator including the compound, a resist composition containing the acid generator, and a method of forming a resist pattern that uses the resist composition, and the invention is therefore extremely useful industrially.

What is claimed is:

1. A resist composition comprising:
a base component (A) which exhibits changed solubility in an alkali developing solution under action of acid; and
an acid-generator component (B) which generates acid upon exposure, wherein said acid-generator component (B) comprises an acid generator (B1) including a compound represented by general formula (b1-11) shown below:

 (b1-11)

wherein $R^{7'''}$ to $R^{9'''}$ each independently represent an aryl group or an alkyl group, wherein two of $R^{7'''}$ to $R^{9'''}$ may be bonded to each other to form a ring with the sulfur atom, and at least one of $R^{7'''}$ to $R^{9'''}$ represents a substituted aryl group having a group represented by general formula (I) shown below as a substituent; and X$^-$ represents an anion:

 (I)

wherein R$^f$ represents a group represented by general formula (I-1) shown below:

 (I-1)

wherein $R^{10'''}$ represents a linear alkylene group, and $R^{11'''}$ represents a linear or branched perfluoroalkyl group.

2. The resist composition according to claim 1, wherein X$^-$ in general formula (b1-11) above is an anion represented by general formula (x-1) shown below:

 (x-1)

wherein $R^{4'''}$ represents an alkyl group, a halogenated alkyl group, an aryl group or an alkenyl group which may have a substituent.

3. The resist composition according to claim 1, wherein X$^-$ in general formula (b1-11) above is an anion represented by general formula (x-11) shown below:

 (x-11)

wherein Q$^1$ represents a divalent linking group containing an oxygen atom; Z represents a hydrocarbon group of 3 to 30 carbon atoms which may have a substituent; and Y$^1$ represents an alkylene group of 1 to 4 carbon atoms which may have a substituent, or a fluorinated alkylene group of 1 to 4 carbon atoms which may have a substituent.

4. The resist composition according to claim 1, which is a positive resist composition.

5. The resist composition according to claim 4, wherein said base component (A) is a resin component (A1) which exhibits increased solubility in an alkali developing solution under action of acid.

6. The resist composition according to claim 5, wherein said resin component (A1) further comprises a structural unit (a1) derived from an acrylate ester having an acid dissociable, dissolution inhibiting group.

7. The resist composition according to claim 6, wherein said resin component (A1) further comprises a structural unit (a2) derived from an acrylate ester containing a lactone-containing cyclic group.

8. The resist composition according to claim 6,
wherein said resin component (A1) further comprises a structural unit (a3) derived from an acrylate ester containing a polar group-containing aliphatic hydrocarbon group.

9. The resist composition according to claim 7,
wherein said resin component (A1) further comprises a structural unit (a3) derived from an acrylate ester containing a polar group-containing aliphatic hydrocarbon group.

10. The resist composition according to claim 1, which further comprises a nitrogen-containing organic compound (D).

11. A method of forming a resist pattern, comprising:
applying a resist composition of claim 1 to a substrate to form a resist film on the substrate;
subjecting said resist film to irradiation exposure with any form of radiation; and
subjecting said resist film to alkali developing to form a resist pattern.

12. A compound represented by general formula (b1-11) shown below:

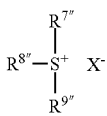
(b1-11)

wherein $R^{7''}$ to $R^{9''}$ each independently represent an aryl group or an alkyl group, wherein two of $R^{7''}$ to $R^{9''}$ may be bonded to each other to form a ring with the sulfur atom, and at least one of $R^{7''}$ to $R^{9''}$ represents a substituted aryl group having a group represented by general formula (I) shown below as a substituent; and $X^-$ represents an anion:

(I)

wherein $R^f$ represents a group represented by general formula (I-1) shown below:

(I-1)

wherein $R^{10''}$ represents a linear alkylene group, and $R^{11''}$ represents a linear or branched perfluoroalkyl group.

13. The compound according to claim 12,
wherein $X^-$ in general formula (b1-11) above is an anion represented by general formula (x-1) shown below:

(x-1)

wherein $R^{4''}$ represents an alkyl group, a halogenated alkyl group, an aryl group or an alkenyl group which may have a substituent.

14. The compound according to claim 12,
wherein $X^-$ in general formula (b1-11) above is an anion represented by general formula (x-11) shown below:

(x-11)

wherein $Q^1$ represents a divalent linking group containing an oxygen atom; Z represents a hydrocarbon group of 3 to 30 carbon atoms which may have a substituent; and $Y^1$ represents an alkylene group of 1 to 4 carbon atoms which may have a substituent, or a fluorinated alkylene group of 1 to 4 carbon atoms which may have a substituent.

15. An acid generator comprising a compound of claim 12.

* * * * *

UNITED STATES PATENT AND TRADEMARK OFFICE
CERTIFICATE OF CORRECTION

PATENT NO. : 8,367,299 B2
APPLICATION NO. : 13/233832
DATED : February 5, 2013
INVENTOR(S) : Akiya Kawaue et al.

It is certified that error appears in the above-identified patent and that said Letters Patent is hereby corrected as shown below:

In the Specification:

At Column 6, Line 3, Change "(A 1)" to --(A1)--.

At Column 6, Line 19, Change "(A 1)" to --(A1)--.

At Column 57, Line 60, Change "norbonyl" to --norbornyl--.

At Column 57, Line 63, Change "2-norbonyl" to --2-norbornyl--.

At Column 57, Line 63, Change "3-norbonyl" to --3-norbornyl--.

At Column 57, Line 66, Change "norbonyl" to --norbornyl--.

At Column 59, Line 59, Change "(a-4-1) to (a-4-5)," to --(a4-1) to (a4-5),--.

At Column 60, Line 16, Change "(A 1)" to --(A1)--.

At Column 60, Line 36, Change "(A 1)." to --(A1).--.

At Column 67, Line 14, Change "H ere," to --Here,--.

At Column 79, Line 39, Change "(b-4-1) to (b-4-8)" to --(b4-1) to (b4-8)--.

At Column 80, Line 45, Change "(b-4-1) to (b-4-4)" to --(b4-1) to (b4-4)--.

At Column 93, Line 29, Change "tris {" to --tris{--.

At Column 103, Line 62, Change "Adamantine)," to --Adamantane),--.

Signed and Sealed this
Twenty-seventh Day of August, 2013

Teresa Stanek Rea
*Acting Director of the United States Patent and Trademark Office*

At Column 104, Line 62, Change "pentaoxide" to --pentoxide--.

At Column 107, Line 22, Change "(s, 3H$^c$)," to --(s, 3H, H$^c$),--.

At Column 112, Line 29, Change "pentaoxide" to --pentoxide--.